(12) United States Patent
Su et al.

(10) Patent No.: US 8,349,859 B2
(45) Date of Patent: Jan. 8, 2013

(54) PYRIMIDINE DERIVATIVES

(75) Inventors: Wei-Guo Su, Shanghai (CN); Hong Jia, Shanghai (CN); Weihan Zhang, Shanghai (CN); Yumin Cui, Shanghai (CN); Xiaoqiang Yan, Shanghai (CN); Yongxin Ren, Shanghai (CN); Jifeng Duan, Shanghai (CN); Yang Sai, Shanghai (CN)

(73) Assignee: Hutchison Medipharma Enterprises Limited, Nassau (BS)

( * ) Notice: Subject to any disclaimer, the term of this patent is extended or adjusted under 35 U.S.C. 154(b) by 1302 days.

(21) Appl. No.: 12/103,876

(22) Filed: Apr. 16, 2008

(65) Prior Publication Data

US 2008/0255172 A1   Oct. 16, 2008

Related U.S. Application Data

(60) Provisional application No. 60/911,921, filed on Apr. 16, 2007.

(51) Int. Cl.
- A01N 43/54 (2006.01)
- A61K 31/505 (2006.01)
- C07D 401/00 (2006.01)
- C07D 403/00 (2006.01)
- C07D 405/00 (2006.01)
- C07D 409/00 (2006.01)
- C07D 411/00 (2006.01)
- C07D 413/00 (2006.01)
- C07D 417/00 (2006.01)
- C07D 419/00 (2006.01)

(52) U.S. Cl. ......... 514/269; 514/275; 544/310; 544/331
(58) Field of Classification Search ........................ None
See application file for complete search history.

(56) References Cited

U.S. PATENT DOCUMENTS

| 5,457,105 | A  | 10/1995 | Barker |
| 6,235,741 | B1 | 5/2001  | Bilodeau et al. |
| 6,723,726 | B1 | 4/2004  | Cockerill et al. |
| 2003/0149041 | A1 | 8/2003 | Erickson et al. |
| 2004/0092750 | A1 | 5/2004 | Hasegawa et al. |
| 2005/0261315 | A1 | 11/2005 | Mehta et al. |
| 2006/0247262 | A1 | 11/2006 | Baenteli et al. |
| 2006/0247263 | A1 | 11/2006 | Siegmund |
| 2006/0270694 | A1 | 11/2006 | Wong |

FOREIGN PATENT DOCUMENTS

| DE | 10 2004044556 A1 | 3/2006 |
| EP | 1154774 | 6/2005 |
| NZ | 535109 | 5/2006 |
| WO | WO 00/78731 A1 | 12/2000 |
| WO | WO 01/29009 A1 | 4/2001 |
| WO | 03/063794 | 8/2003 |
| WO | 2004/014382 | 2/2004 |
| WO | 2005/009978 | 2/2005 |
| WO | 2005/026158 | 3/2005 |
| WO | WO 2005/026130 A1 | 3/2005 |
| WO | 2005/063739 | 7/2005 |
| WO | WO 2006/053109 A1 | 5/2006 |
| WO | WO 2006/060194 A1 | 6/2006 |
| WO | 2006/071017 | 7/2006 |
| WO | 2006/071079 | 7/2006 |
| WO | 2006/138304 | 12/2006 |

OTHER PUBLICATIONS

Sisko et al., "Potent 2-(pyrimidin-4-yl)amine}-1,3-thiazole-5-carbonitrile-based inhibitors of VEGFR-2 (KDR) kinase," *Bioorganic & Medicinal Chemistry Letters*, 16: 1146-1150 (2006).

Bamborough et al., "N-4-Pyrimidinyl-IH-indazol-4-amine inhibitors of Lck: Indazoles as phenol isosteres with improved pharmacokinetics," *Bioorganic & Medicinal Chemistry Letters*, 17: 4363-4368 (2007).

Supplementary European Search Report dated Apr. 21, 2010 for European Application No. 08 745 881.6.

Verma et al. "Substituted Aminobenzimidazole Pyrimidines as Cyclin-Dependent Kinase Inhibitors" Bioorganic & medicinal Chemistry Letters 15 92005) 1973-1977, 5 pages.

Zhang et al. "Discovery of EGFR Selective 4,6-Disubstituted Pyrimidines from a Combinatorial Kinase-Directed Heterocycle Library," J.A.M. Chem. Soc. 2006, 128, 2182-2183.

International Search Report and Written Opinion for PCT Application No. PCT/US2008/60366 dated Jul. 17, 2008, 10 pages.

*Primary Examiner* — Jeffrey Murray

(74) *Attorney, Agent, or Firm* — Finnegan, Henderson, Farabow, Garrett & Dunner, LLP

(57) ABSTRACT

A compound of the following formula:

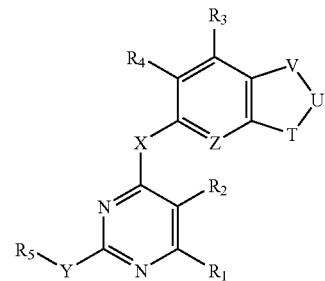

wherein $R_1$, $R_2$, $R_3$, R4, R5, T, U, V, X, Y, Z, G, and Z are defined herein. It also discloses a method of treating an angiogenesis-related disorder, e.g., cancer or age-related macular degeneration, with such a compound.

12 Claims, No Drawings

PYRIMIDINE DERIVATIVES

CROSS REFERENCE TO RELATED APPLICATIONS

This application claims priority to U.S. Provisional Application Ser. No. 60/911,921, filed Apr. 16, 2007. The contents of the prior application are hereby incorporated by reference in their entireties.

BACKGROUND

Angiogenesis is a physiological process of growing new blood vessels from pre-existing vessels. It takes place in a healthy subject to heal wounds, i.e., restoring blood flow to tissues after injury or insult.

Excessive blood vessel growth may be triggered by certain pathological conditions such as cancer, age-related macular degeneration, rheumatoid arthritis, and psoriasis. As a result, new blood vessels feed diseased tissues and destroy normal tissues. In cancer, new blood vessels also allow tumor cells to escape into the circulation and lodge in other organs.

Vascular endothelial growth factor (VEGF), a homodimeric glycoprotein, and its receptors, e.g., kinase insert domain receptor (KDR), constitute an important angiogenic pathway. Studies have shown that inhibition of KDR resulted in endothelial cell apoptosis and, thus, suppression of angiogenesis. See Rubin M. Tuder, *Chest*, 2000; 117: 281. KDR inhibitors are therefore potential candidates for treating angiogenesis-related diseases.

SUMMARY

This invention is based on the discovery that a number of pyrimidine compounds inhibit the activity of KDR.

One aspect of this invention features pyrimidine compounds of the following formula (I):

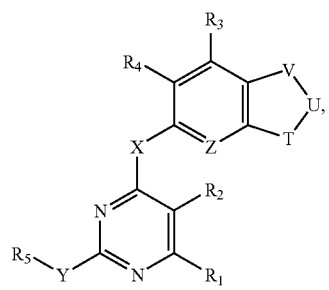

(I)

in which each of X and Y, independently, is O, S, or NR, wherein R is H, alkyl, alkenyl, alkynyl, aryl, cycloalkyl, heterocycloalkyl, heteroaryl, alkylcarbonyl, alkoxycarbonyl, aminocarbonyl, or aminosulfonyl; Z is CR' or N, wherein R' is H, halo, nitro, cyano, hydroxyl, alkoxy, aryloxy, alkyl, alkenyl, alkynyl, aryl, cycloalkyl, or heterocycloalkyl; V, U, and T together represent

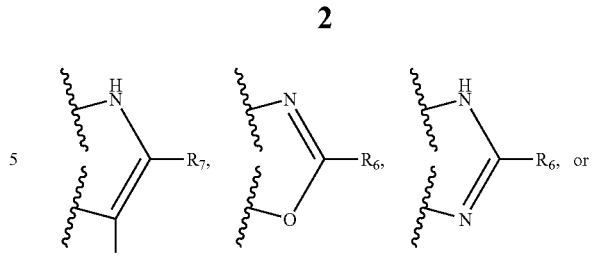

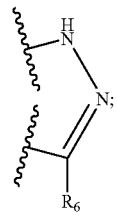

each of $R_1$, $R_2$, $R_3$, $R_4$, and $R_6$, independently, is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl; $R_5$ is alkyl, cycloalkyl, heterocycloalkyl, aryl or heteroaryl; and $R_7$ is alkyl.

Referring to formula (I), one subset of the compounds features that $R_1$, $R_2$, $R_3$, and $R_4$ is H and $R_5$ is aryl or heteroaryl, optionally substituted with halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, sulfonyl, carbonylamino, sulfonylamino, aminocarbonyl, or aminosulfonyl. Another subset features that X is O or NH; Y is NH; V, U, and T together represent

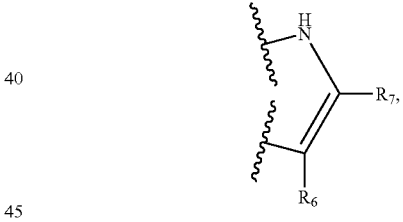

in which $R_6$ can be H and $R_7$ can be methyl; or Z is CR', in which R' is H, halo, or alkyl.

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocycloalkyl" refers to a nonaromatic 5-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl. Heterocycloalkyl can be a saccharide ring, e.g., glucosyl.

Alkyl, cycloalkyl, heterocycloalkyl, aryl, heteroaryl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, heterocycloalkyl, in which alkyl, alkenyl, alkynyl, alkyloxy, aryl, heteroaryl cycloalkyl, and heterocycloalkyl may further substituted.

The pyrimidine compounds described above include their pharmaceutically acceptable salts, hydrate and prodrug, if applicable.

Another aspect of this invention features a method of treating an angiogenesis-related disorder (e.g., cancer or age-related macula degeneration). The method includes administering to a subject having such an disorder an effective amount of one or more of the above-described pyrimidine compounds.

Still another aspect of this invention features a method of inhibiting the activity of kinase insert domain receptor by contacting the receptor with an effective amount of a pyrimidine compound of formula (II):

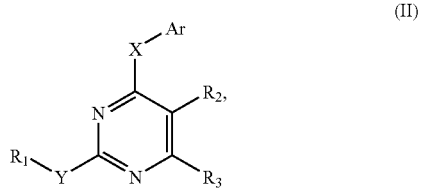

(II)

in which $R_1$ is H, alkyl, alkenyl, alkynyl, aryl, cycloalkyl, heterocycloalkyl, or heteroaryl; each of $R_2$ and $R_3$, independently, is H, halogen, nitro, amino, CN, hydroxy, alkyl, alkenyl, alkynyl, aryl, cycloalkyl, heterocycloalkyl, heteroaryl, alkoxy, alkylcarbonyl, carboxy, or alkoxycarbonyl; each of X and Y, independently, is O, S, or $NR_4$, wherein $R_4$ is H, alkyl, alkenyl, alkynyl, aryl, cycloalkyl, heterocycloalkyl, heteroaryl, alkylcarbonyl, alkoxycarbonyl, aminocarbonyl, or aminosulfonyl; and Ar is aryl or heteroaryl.

Referring to formula (II), one subset of the compounds features that Ar is indolyl, indazolyl, benzoimidazolyl, or benzoxazolyl; X is O or NH and Y is NH; or $R_1$ is aryl or heteroaryl, optionally substituted with halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, sulfonyl, carbonylamino, sulfonylamino, aminocarbonyl, or aminosulfonyl.

Exemplary compounds 1-317 are shown in the Detailed Description section below.

Yet another aspect of this invention features a method of inhibiting angiogenesis, or treating age-related macular degeneration, by administrating to a subject in need thereof an effective amount of a pyrimidine compound of formula (II) as described above.

Also within the scope of this invention are (1) a composition containing one or more of the pyrimidine compounds described above and a pharmaceutically acceptable carrier for use in treating an angiogenesis-related disorder (e.g., such cancer or age-related macular degeneration) and (2) use of one or more of the pyrimidine compounds for the manufacture of a medicament for treating the disorder.

The details of one or more embodiments of the invention are set forth in the description below. Other features, objects and advantages of the invention will be apparent from the description and from the claims.

DETAILED DESCRIPTION

The compounds described above can be synthesized from commercially available starting materials by methods well known in the art. As an example, one can replace leaving groups (e.g., chloride, p-TsO, MeS, or $MeSO_2$) at the active N2, N4-positions of a suitable pyrimidine compound with nucleophilic groups such as amino or hydroxyl via, e.g., Buchwald-Hartwig coupling reaction. The replacement can be first effected either at the N2 position or the N4 position.

The compounds thus obtained can be further modified at their peripheral positions to provide the desired compounds.

Synthetic chemistry transformations useful in synthesizing desirable pyrimidine compounds are described, for example, in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the compounds can be purified by column chromatography, high performance liquid chromatography, crystallization, or other suitable methods.

The pyrimidine compounds described above, when contacting with KDR, inhibit this receptor's activity. An effective amount of one or more of these compounds can be therefore used to inhibit angiogenesis and treat a subject having an angiogenesis-related disorder.

The term "an effective amount" refers to the amount of a pyrimidine compound that is required to confer the intended effect in the subject. Effective amounts may vary, as recognized by those skilled in the art, depending on route of administration, excipient usage, and the possibility of co-usage with other agents. The term "treating" refers to administering one or more of the above-described pyrimidine compounds to a subject that has an angiogenesis-related disorder, or has a symptom of the disorder, or has a predisposition toward the disorder, with the purpose to cure, heal, alleviate, relieve, alter, remedy, ameliorate, improve, or affect the disorder, the symptoms of the disorder, or the predisposition toward the disorder.

To practice this method, a composition having one or more of the pyrimidine compounds of this invention can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond and about 70% by weight white soft paraffin.

A carrier in a pharmaceutical composition must be "acceptable" in the sense that it is compatible with active ingredients of the formulation (and preferably, capable of stabilizing it) and not deleterious to the subject to be treated. For example, solubilizing agents, such as cyclodextrins (which form specific, more soluble complexes with one or more of active pyrimidine compounds of the extract), can be utilized as pharmaceutical excipients for delivery of the active ingredients. Examples of other carriers include colloidal silicon dioxide, magnesium stearate, cellulose, sodium lauryl sulfate, and D&C Yellow #10.

Suitable in vitro assays can be used to preliminarily evaluate the efficacy of the above-described pyrimidine compounds in inhibiting the activity of KDR or inhibiting the activity of VEGF. The compounds can further be examined for its efficacy in treating an angiogenesis-related disorder by in vivo assays. For example, the compounds can be administered to an animal (e.g., a mouse model) having cancer and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever.

Example 1

Synthesis of N4-(2-methyl-1H-indol-5-yl)-N2-phenylpyrimidine-2,4-diamine (Compound 1)

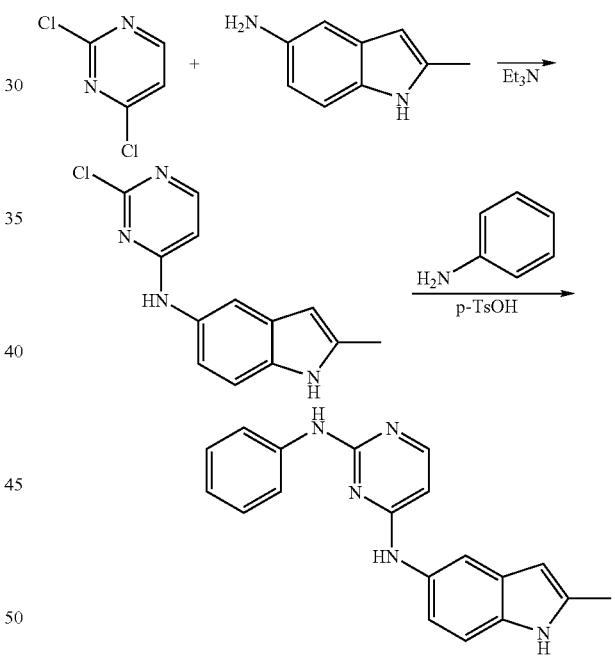

Compound 1

Et$_3$N (1 mmol) was added to a solution of 2,4-dichloropyrimidine (1 mmol) and 5-amino-2-methylindole (1 mmol) in 5 ml EtOH. The reaction mixture was refluxed for 5 hours. After removal of the solvent in vacuo and addition of H$_2$O, the mixture was extracted with EtOAc. The organic layers were combined, washed with saturated NaCl solution, dried over anhydrous Na$_2$SO$_4$, and concentrated in vacuo. The resulting residue was purified by column chromatography to give N-(2-chloropyrimidin-4-yl)-2-methyl-1H-indol-5-amine in a yield of 80%.

N-(2-chloropyrimidin-4-yl)-2-methyl-1H-indol-5-amine (0.1 mmol) and aniline (0.1 mmol) were dissolved in 0.5 ml DMF. To this was added p-TsOH monohydrate (0.2 mmol).

The reaction mixture was stirred at 60° C. for 5 hours, diluted with water, and extracted with ethyl acetate. The organic layer was washed with water and brine sequentially, dried over anhydrous Na$_2$SO$_4$, and concentrated. The resulting residue was purified by column chromatography to provide the title product in a yield of 85%.

$^1$H NMR (CD$_3$OD, 400 MHz): δ 7.831 (d, J=6.0 Hz, 1H), 7.633 (t, J=8.0-7.6 Hz, 3H), 7.262 (t, J=8.4-7.6 Hz, 3H), 7.064 (d, J=6.8 Hz, 1H), 6.995 ((t, J=7.6-7.2 Hz, 1H), 6.133 (t, J=6.4-2.0 Hz, 2H), 2.439 (s, 3H); MS (m/e): 384.2 (M+1).

Example 2-283

Synthesis of Compounds 2-283

Compounds 2-283 were each synthesized in a manner similar to that described in Example 1.

| Compound | Name/Structure | $^1$H NMR (400 MHz, δ ppm)/MS |
|---|---|---|
| 2 | N2-(3-ethynylphenyl)-N4-(2-methyl-1H-indol-5-yl)pyrimidine-2,4-diamine | (CD$_3$OD): 7.848 (d, J = 6.8 Hz, 1 H), 7.730 (s, 1 H), 7.704 (d, J = 8.0 Hz, 1 H), 7.507 (s, 1 H), 7.275 (d, J = 8.0 Hz, 1 H), 7.200 (t, J = 8.0 Hz, 1 H), 7.093-7.036 (m, 2 H), 6.639 (m, 2 H), 2.425 (s, 3 H); MS (m/e): 340.4 (M + 1) |
| 3 | N2-(3-bromophenyl)-N4-(2-methyl-1H-indol-5-yl)pyrimidine-2,4-diamine | (CD$_3$OD): 7.879 (s, 1 H), 7.784 (d, J = 6.0 Hz, 1 H), 7.437 (br, 1 H), 7.373 (s, 1 H), 7.255 (d, J = 8.8 Hz, 1 H), 7.079 (br, 2 H), 6.968 (d, J = 8.4 Hz, 1 H), 6.133 (s, 1 H), 6.041 (d, J = 6.4 Hz, 1 H), 2.400 (s, 3 H); MS (m/e): 394.3 (M) |
| 4 | N2-(3-fluorophenyl)-N4-(2-methyl-1H-indol-5-yl)pyrimidine-2,4-diamine | (CD$_3$OD): 7.923 (s, 1 H), 7.759 (d, J = 6.0 Hz, 1 H), 7.641 (d, J = 8.0 Hz, 1 H), 7.397 (s, 1 H), 7.247 (d, J = 8.4 Hz, 1 H), 7.179-7.053 (m, 1 H), 6.963 (d, J = 8.4 Hz, 1 H), 6.575 (t, J = 8.0 Hz, 1 H), 6.125 (s, 1 H), 6.044 (d, J = 6.0 Hz, 1 H), 2.395 (s, 3 H); MS (m/e): 334.2 (M + 1) |
| 5 | N2-(3-chlorophenyl)-N4-(2-methyl-1H-indol-5-yl)pyrimidine-2,4-diamine | (CD$_3$OD): 7.838 (d, J = 6.8 Hz, 1 H), 7.746 (s, 1 H), 7.526 (br, 2 H), 7.298 (d, J = 8.4 Hz, 1 H), 7.212 (t, J = 8,0 Hz, 1 H), 7.102 (d, J = 8.4 Hz, 1 H), 7.001 (d, J = 8.0 Hz, 1 H), 6.217 (d, J = 6.0 Hz, 1 H), 6.133 (s, 1 H), 2.436 (s, 3 H); MS (m/e): 350.2 (M + 1) |

| Compound | Name/Structure | $^1$H NMR (400 MHz, δ ppm)/MS |
|---|---|---|
| 6 | N4-(2-methyl-1H-indol-5-yl)-N2-(3-(trifluoromethyl)phenyl) pyrimidine-2,4-diamine 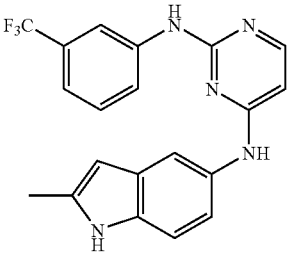 [SMILES: Cc1cc2cc(Nc3ccnc(Nc4cccc(C(F)(F)F)c4)n3)ccc2[nH]1] | (CD$_3$OD): 8.045 (d, J = 7.2 Hz, 1 H), 7.788 (d, J = 6.0 Hz, 2 H), 7.529 (s, 1 H), 7.366 (d, J = 6.8 Hz, 1 H), 7.276 (d, J = 8.4 Hz, 1 H), 7.228 (d, J = 7.2 Hz, 1 H), 7.083 (d, J = 1.2 Hz, 1 H), 6.190 ((d, J = 6.4 Hz, 1 H), 6.115 (s, 1 H), 2.440 (s, 3 H). MS (m/e): 384.2 (M + 1) |
| 7 | N4-(2-methyl-1H-indol-5-yl)-N2-(3-(methylsulfonyl)phenyl) pyrimidine-2,4-diamine 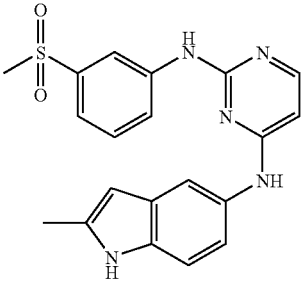 [SMILES: Cc1cc2cc(Nc3ccnc(Nc4cccc(S(C)(=O)=O)c4)n3)ccc2[nH]1] | (CD$_3$OD): 11.471 (s, 1 H), 9.461 (s, 1 H), 9.364 (s, 1 H), 8.441 (s, 1 H), 8.236 (s, 1 H), 7.988 (d, J = 5.6 Hz, 1 H), 7.396 (M,, 5 H), 7.303 (d, J = 8.4 Hz, 1 H), 6.255 (d, J = 5.6 Hz, 1 H), 3.111 (s, 3 H), 2.456 (s, 3 H). MS (m/e): 393.2 (M + 1) |
| 8 | N2-(3-methoxylphenyl)-N4-(2-methyl-1H-indol-5-yl)pyrimidine-2,4-diamine 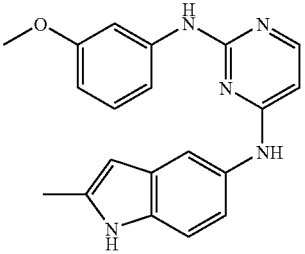 [SMILES: COc1cccc(Nc2nccc(Nc3ccc4[nH]c(C)cc4c3)n2)c1] | (CD$_3$OD): 8.050 (s, 1 H), 7.943 (d, J = 6.0 Hz, 1 H), 7.440-7.362 (m, 3 H), 7.293 (s, 1 H), 7.223 (t, J = 8.0 Hz, 2 H), 7.122 (d, J = 7.6 Hz, 1 H), 7.0211 (d, J = 6.8 Hz, 1 H), 6.808 (s, 1 H), 6.680 (d, J = 6.4 Hz, 1 H), 6.222 (s, 1 H), 6.068 (d, J = 5.6 Hz, 1 H), 3.790 (s, 3 H), 2.472 (s, 3 H); MS (m/e): 345.9 (M + 1) |
| 9 | ethyl 1-(3-(4-(2-methyl-1H-indol-5-ylamino)pyrimidin-2-ylamino)benzyl)piperidine-4-carboxylate 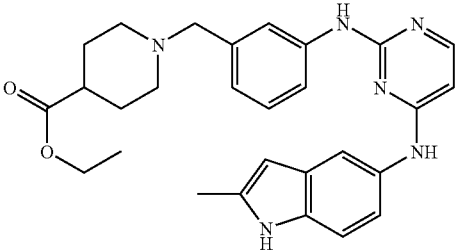 [SMILES: CCOC(=O)C1CCN(Cc2cccc(Nc3nccc(Nc4ccc5[nH]c(C)cc5c4)n3)c2)CC1] | (CD$_3$OD): 8.019 (s, 1 H), 7.889 (d, J = 5.6 Hz, 1 H), 7.554 (s, 1 H), 7.399 (d, J = 8.0 Hz, 1 H), 7.328 (d, J = 8.4 Hz, 1 H), 7.278 (t, J = 8.0 Hz, 1 H), 7.101 (d, J = 8.0 Hz, 1 H), 7.002 (d, J = 7.2 Hz, 1 H), 6.180 (d, J = 6.0 Hz, 1 H), 6.141 (s, 1 H), 4.166 (q, J = 7.2 Hz, 1 H), 3.586 (s, 2 H), 2.973-2.943 (m, 2 H), 2.462 (s, 3 H), 2.316 (br, 1 H), 2.089 (m, 2 H), 1.939-1.885 (m, 2 H), 1.741-1.653 (m, 2 H), 1.272 (t, J = 7.2 Hz, 2 H); MS (m/e): 485.4 (M + 1) |

| Compound | Name/Structure | $^1$H NMR (400 MHz, δ ppm)/MS |
|---|---|---|
| 10 | N2,N4-bis(2-methyl-1H-indol-5-yl)pyrimidine-2,4-diamine 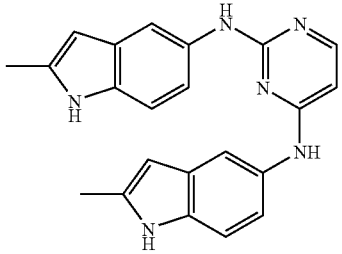 [SMILES: Cc1cc2cc(Nc3ccnc(Nc4ccc5[nH]c(C)cc5c4)n3)ccc2[nH]1] | (CD$_3$OD): 7.675 (d, J = 6.4 Hz, 1 H), 7.625 (s, 1 H), 7.577 (br, 1 H), 7.266-7.219 (m, 2 H), 7.068-7.051 (m, 1 H), 6.116 (d, J = 6.0 Hz, 1 H), 6.072 (s, 1 H), 6.014 (s, 1 H), 2.435 (s, 3 H), 2.425 (s, 3 H); MS (m/e): 369.3 (M + 1) |
| 11 | N2-(1H-indazol-5-yl)-N4-(2-methyl-1H-indol-5-yl)pyrimidine-2,4-diamine 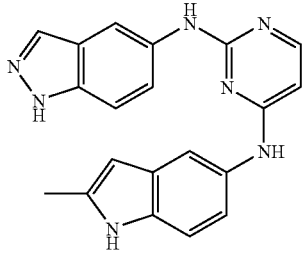 [SMILES: Cc1cc2cc(Nc3ccnc(Nc4ccc5[nH]ncc5c4)n3)ccc2[nH]1] | (CD$_3$OD): 12.385 (s, 1 H), 10.928 (s, 1 H), 9.120 (s, 1 H), 9.003 (s, 1 H), 8.259 (s, 1 H), 7.920 (d, J = 6.0 Hz, 1 H), 7.758 (s, 1 H), 7.667 (s, 1 H), 7.541 (d, J = 8.8 Hz, 2 H), 7.399 (d, J = 8.8 Hz, 1 H), 7.242 (d, J = 8.8 Hz, 1 H), 7.151 (d, J = 8.8 Hz, 1 H), 6.142 (d, J = 6.0 Hz, 1 H), 6.017 (s, 1 H), 2.389 (s, 3 H). MS (m/e): 356.3 (M + 1) |
| 12 | N2-(1H-benzo[d]imidazol-5-yl)-N4-(2-methyl-1H-indol-5-yl)pyrimidine-2,4-diamine 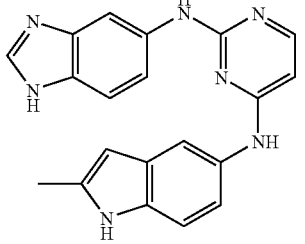 | (CD$_3$OD): 10.853 (s, 1 H), 9.033 (s, 1 H), 8.956 (s, 1 H), 8.077 (br, 2 H), 7.925 (d, J = 6.0 Hz, 1 H), 7.736 (s, 1 H), 7.533 (d, J = 8.0 Hz, 1 H), 7.444 (d, J = 8.8 Hz, 1 H), 7.214-7.144 (m, 2 H), 6.131 (d, J = 6.0 Hz, 1 H), 6.020 (s, 1 H), 2.372 (s, 3 H); MS (m/e): 356.3 (M + 1) |
| 13 | N2-(2-methoxyphenyl)-N4-(2-methyl-1H-indol-5-yl)pyrimidine-2,4-diamine 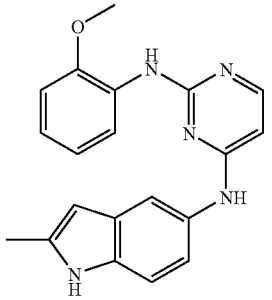 [SMILES: COc1ccccc1Nc1nccc(Nc2ccc3[nH]c(C)cc3c2)n1] | (CD$_3$OD): 8.496 (s, 1 H), 8.002 (d, J = 6.0 Hz, 2 H), 7.446 (s, 1 H), 7.047 (dd, J = 8.8 Hz, J = 2.4 Hz, 1 H), 6.981-6.957 (m, 2 H), 6.913-6.771 (m, 1 H), 6.889 (s, 1 H), 6.243 (s, 1 H), 6.083 (d, J = 6.0 Hz, 1 H), 3.910 (s, 3 H), 2.490 (s, 3 H). MS (m/e): 346.2 (M + 1) |

-continued

| Compound | Name/Structure | $^1$H NMR (400 MHz, δ ppm)/MS |
|---|---|---|
| 14 | N2-(2-chlorophenyl)-N4-(2-methyl-1H-indol-5-yl)pyrimidine-2,4-diamine | (CD$_3$OD): 8.385 (d, J = 6.0 Hz, 1 H), 7.914 (s, 1 H), 7.849 (s, 1 H), 7.325 (d, J = 7.6 Hz, 1 H), 7.237 (d, J = 8.4 Hz, 1 H), 7.182 (t, J = 7.6 Hz, 1 H), 6.945-6.870 (m, 2 H), 6.119 (s, 1 H), 6.070 (d, J = 6.0 Hz, 1 H), 2.397 (s, 3 H); MS (m/e): 350.1 (M + 1) |
| 15 | N2-(2-bromophenyl)-N4-(2-methyl-1H-indol-5-yl)pyrimidine-2,4-diamine | (CD$_3$OD): 10.860 (s, 1 H), 9.204 (s, 1 H), 8.140 (d, J = 8.4 Hz, 1 H), 7.916 (d, J = 5.6 Hz, 2 H), 7.651 (d, J = 7.6 Hz, 2 H), 7.334 (t, J = 7.6 Hz, 1 H), 7.184 (d, J = 8.8 Hz, 1 H), 7.038 (br, 2 H), 6.192 (d, J = 6.0 Hz, 1 H), 6.012 (s, 1 H), 2.369 (s, 3 H); MS (m/e): 394.3 (M) |
| 16 | N2-(4-fluorophenyl)-N4-(2-methyl-1H-indol-5-yl)pyrimidine-2,4-diamine | (CD$_3$OD): 10.889 (s, 1 H), 9.256 (s, 1 H), 9.245 (s, 1 H), 7.966 (d, J = 5.6 Hz, 1 H), 7.752 (m, J = 8.4-3.6Hz, 2 H), 7.236 (d, J = 5.4 Hz 1 H), 7.133 (m, J = 8.4-3.6 Hz, 3 H), 6.086 (d, J = 5.6 Hz, 1 H), 6.050 (s, 1 H), 2.402 (s, 3 H); MS (m/e): 334.2 (M + 1) |
| 17 | methyl 2-(4-(4-(2-methyl-1H-indol-5-ylamino)pyrimidin-2-ylamino)phenyl)acetate | (CD$_3$OD): 10.907 (s, 1 H), 9.132 (s, 1 H), 9.015 (s, 1 H), 7.914 (s, 1 H), 7.713 (d, J = 6 Hz, 1 H), 7.498 (d, J = 6.8 Hz, 1 H), 7.217 (d, J = 7.2 Hz, 1 H), 7.127 (m, 4 H), 6.149 (d, J = 6 Hz, 1 H), 6.067 (s, 1 H), 2.384 (s, 3 H), 2.272 (s, 3 H), 1.288 (s, 2 H). MS (m/e): 387.2 (M + 1) |

-continued

| Compound | Name/Structure | ¹H NMR (400 MHz, δ ppm)/MS |
|---|---|---|
| 18 | N4-(2-methyl-1H-indol-5-yl)-N2-(4-phenoxyphenyl)pyrimidine-2,4-diamine 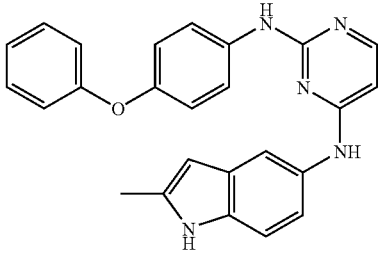 [SMILES: Cc1cc2cc(Nc3ccnc(Nc4ccc(Oc5ccccc5)cc4)n3)ccc2[nH]1] | (CD$_3$OD): 10.855 (s, 1 H), 9.098 (s, 1 H), 9.065 (s, 1 H), 7.909 (d, J = 5.6 Hz, 1 H), 7.786 (d, J = 8 Hz, 2 H), 7.365 (t, J = 7.6 Hz, 2 H), 7.346 (s, 1 H), 7.201 (d, J = 8.8 Hz, 1 H), 7.086 (m, 2 H), 6.962 (d, 8 Hz, 2 H), 6.895 (d, J = 8 Hz, 2 H), 6.137 (d, J = 5.6 Hz, 1 H), 6.021 (s, 1 H), 2.331 (s, 3 H). MS (m/e): 407.5 (M + 1) |
| 19 | N2-(4-methoxyphenyl)-N4-(2-methyl-1H-indol-5-yl)pyrimidine-2,4-diamine 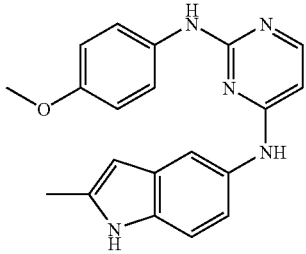 [SMILES: COc1ccc(Nc2nccc(Nc3ccc4[nH]c(C)cc4c3)n2)cc1] | (CD$_3$OD): 11.097 (s, 1 H), 9.479 (s, 1 H), 9.243 (s, 1 H), 8.090 (d, J = 6 Hz, 1 H), 7.923 (s, 1 H), 7.822 (m, 2 H), 7.420 (d, 8.8 Hz, 1 H), 7.307 (s, 1 H), 7.025 (d, J = 8.8 Hz, 2 H), 6.340 (m, 1 H), 6.265 (s, 1 H), 3.941 (s, 3 H), 2.591 (s, 3 H); MS (m/e): 345.4 (M + 1) |
| 20 | N4-(2-methyl-1H-indol-5-yl)-N2-(4-(2-morpholinoethoxy)phenyl) pyrimidine-2,4-diamine 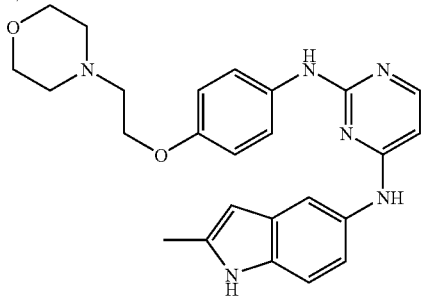 | (CD$_3$OD): 10.899 (s, 1 H), 9.074 (s, 1 H), 8.823 (s, 1 H), 7.869 (d, J = 6 Hz, 1 H), 7.713 (s, 1 H), 7.621 (d, J = 8.8 Hz, 2 H), 7.200 (d, J = 8.4 Hz, 1 H), 7.080 (s, 1 H), 6.784 (m, 2 H), 6.101 (d, J = 5.6 Hz, 1 H), 6.025 (s, 1 H), 4.034 (t, J = 5.6 Hz, 2 H), 3.585 (t, J = 4.8 Hz, 4 H), 2.679 (t, J = 5.6 Hz, 2 H), 2.475 (t, J = 6.4 Hz, 4 H), 2.375 (s, 3 H); MS: 444.5 (M + 1) |
| 21 | N2-(3, 4-difluorophenyl)-N4-(2-methyl-1H-indol-5-yl)pyrimidine-2,4-diamine 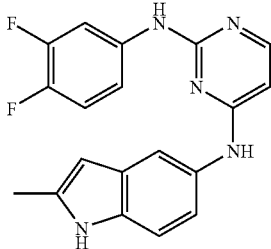 [SMILES: Cc1cc2cc(Nc3ccnc(Nc4ccc(F)c(F)c4)n3)ccc2[nH]1] | (CD$_3$OD): 11.234 (s, 1 H), 9.886 (s, 1 H), 9.754 (s, 1 H), 7.966 (d, J = 5.6 Hz, 2 H), 7.752 (s, 1 H), 7.393 (m, J = 8.4-3.6 Hz, 3 H), 7.133 (d, J = 5.6 Hz, 1 H), 6.251 (d, J = 4.5 Hz, 1 H), 6.1.9 (s, 1 H), 2.402 (s, 3 H); MS (m/e): 352.2 (M + 1) |

-continued

| Compound | Name/Structure | $^1$H NMR (400 MHz, δ ppm)/MS |
|---|---|---|
| 22 | N2-(3,5-dimethylphenyl)-N4-(2-methyl-1H-indol-5-yl)pyrimidine-2,4-diamine | (CD$_3$OD): 10.863 (s, 1 H), 9.051 (s, 1 H), 8.841 (s, 1 H), 7.905 (d, J = 6 Hz, 1 H), 7.633 (s, 1 H), 7.367 (s, 1 H), 7.207 (m, 2 H), 6.507 (s, 1 H), 6.118 (d, J = 5.6 Hz, 1 H), 6.032 (s, 2 H), 2.370 (s, 3 H), 2.171 (s, 6 H); MS (m/e): 343.4 (M + 1). |
| 23 | 2-(4-(2-methyl-1H-indol-5-ylamino)pyrimidin-2-ylamino)ethanol | (CD$_3$OD): 7.939 (d, J = 8.0 Hz, 1 H), 6.923 (d, J = 6.8 Hz, 2 H), 6.437 (s, 1 H), 6.328 (d, J = 7.6 Hz, 2 H), 6.218 (s, 1 H), 6.231 (d, J = 5.6 Hz, 1 H), 5.726 (d, J = 7.2 Hz, 1 H), 3.735 (t, J = 7.2-6.4 Hz, 3 H), 3.225 (t, J = 6.8-5.6 Hz, 3 H), 2.247 (s, 3 H); MS (m/e): 384.1 (M + 1) |
| 24 | N4-(2-methyl-1H-indol-5-yl)-N2-(2-morpholinoethyl)pyrimidine-2,4-diamine | (CD$_3$OD): 7.796 (d, J = 6.0 Hz, 1 H), 7.497 (s, 1 H), 7.246 (d, J = 8.8 Hz, 1 H), 7.076 (d, J = 2.8 Hz, 1 H), 6.148 (s, 1 H), 5.625 (d, J = 4.8 Hz, 1 H), 3.760 (m, J = 3.2-2.8 Hz, 4 H), 3.165 (t, J = 3.2-2.4, 2 H), 2.619 (t, J = 2.0-0.8 Hz, 2 H), 2.447 (m, J = 2.0-1.2 Hz, 4 H), 2.317 (s, 3 H). MS (m/e): 353.2 (M + 1) |
| 25 | N-cyclopropyl-2-(3-(4-(2-methyl-1H-indol-5-ylamino)pyrimidin-2-ylamino)phenyl)acetamide | (DMSO-d$_6$,): 7.920 (d, J = 5.6 Hz, 1 H), 7.700 (m, 2 H), 7.546 (s, 1 H), 7.220 (d, J = 8.0 Hz, 1 H), 7.120 (m, 2 H), 6.778 (d, J = 8.0 Hz, 1 H), 6.200 (d, J = 6.0 Hz, 1 H), 6.066 (s, 1 H), 3.027 (s, 2 H), 2.593 (m, 1 H), 2.380 (s, 3 H), 0.608 (m, 2 H), 0.404 (m, 2H). MS (m/e): 413.5 (M + 1). |
| 26 | N2-(3-(2-(dimethylamino)ethylsulfonyl)phenyl)-N4-(2-methyl-1H-indol-5-yl)pyrimidine-2,4-diamine | (CD$_3$OD): 8.237 (s, 1 H), 8.042 (d, J = 6.8 Hz 1 H), 7.867 (d, J = 6.0 Hz, 1 H), 7.477 (s, 1 H), 7.465 (br, 2 H), 7.253 (d, J = 8.8 Hz, 1 H), 7.028 (d, J = 8.0 Hz 1 H), 6.141 (d, J = 5.6 Hz 1 H), 6.088 (s, 1 H), 3.230 (t, J = 7.6 Hz, 2 H), 2.666 (t, J = 7.2 Hz, 2 H), 2.409 (s, 3 H) , 2.165 (s, 6 H); MS: 451.4 (M + 1). |
| 27 | N4-(2-methyl-1H-indol-5-yl)-N2-(3-(1-(methylsulfonyl)piperidin-4-yloxy)phenyl)pyrimidine-2,4-diamine | (DMSO-d6): 10.976 (s, 1 H), 9.240 (s, 1 H), 9.036 (s, 1 H), 7.054-8.014 (m, 7H), 6.401-6.564 (m, 1 H), 6.114-6.278 (m, 1 H), 6.012-6.073 (m, 1 H), 4.224-4.383 (m, 1 H), 3.110-3.209 (m, 2 H), 2.770-2.886 (m, 2 H), 2.370(s, 3 H), 1.806-1.970 (m, 2 H), 1.578-1.712 (m, 1 H); MS (m/e): 493.5 (M + 1) |

| Compound | Name/Structure | ¹H NMR (400 MHz, δ ppm)/MS |
|---|---|---|
| 28 | N-(3-(4-(2-methyl-1H-indol-5-ylamino)pyrimidin-2-ylamino)phenyl)methanesulfonamide 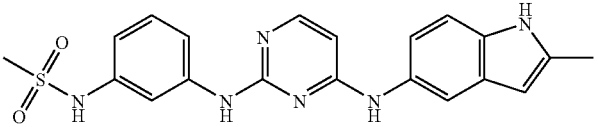 | (CD$_3$OD): 7.856 (d, J = 6.0 Hz, 1 H), 7.652 (s, 1 H), 7.543 (s, 1 H), 7.432 (dd, J = 8.4 Hz, 1 H), 7.271 (d, J = 8.4 Hz, 1 H), 7.196 (t, J = 8.0 Hz, 1 H), 6.882 (dd, J = 8.0 Hz, 2 H), 6.130 (d, J = 6.0 Hz, 2 H), 2.440 (s, 3 H), 2.172 (s, 3 H); MS (m/e): 409.3 (M + 1) |
| 29 | N4-(2-methyl-1H-indol-5-yl)-N2-(3-(2-morpholinoethoxy) phenyl) pyrimidine-2,4-diamine 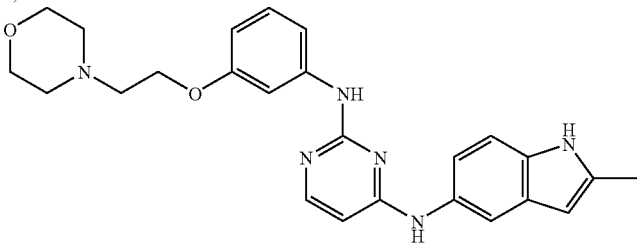 | (DMSO-d$_6$): δ10.825 (s, 1 H), 9.023 (s, 1 H), 8.986 (s, 1 H), 7.927 (d, J = 5.6 Hz, 1 H), 7.703 (s, 1 H), 7.429 (s, 1 H), 7.351 (d, J = 2.4 Hz, 1 H), 7.208 (d, J = 8.8 Hz, 1 H), 7.076 (m, J = 8 Hz, 2 H), 6.469 (dd, J = 8, 2.4 Hz, 1 H), 6.118 (d, J = 2 Hz, 1 H), 6.057 (s, 1 H), 3.933 (t, J = 5.6 Hz, 2 H), 3.551 (t, J = 4.8 Hz, 4 H), 2.591 (t, J = 5.6 Hz, 2 H), 2.401 (t, J = 4.8 Hz, 4 H), 2.379 (s, 3 H); MS (m/e): 444.5 (M + 1). |
| 30 | N2-(3-(3-(dimethylamino)propoxy)phenyl)-N4-(2-methyl-1H-indol-5-yl)pyrimidine-2,4-diamine 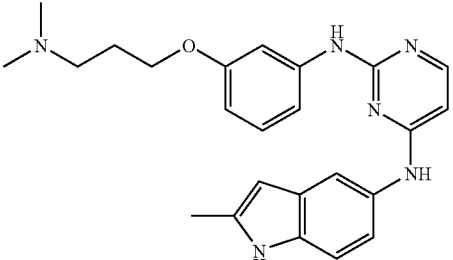 | (CD$_3$OD): 10.836 (s, 1 H), 9.021 (s, 1 H), 8.983 (s, 1 H), 7.926 (d, J = 6 Hz, 1 H), 7.691 (s, 1 H), 7.419 (s, 1 H), 7.345 (d, J = 8.4 Hz, 1 H), 7.212 (d, J = 8.4 Hz, 1 H), 7.079 (m, 2 H), 6.444 (dd, J = 8, 2.4 Hz, 1 H), 6.118 (d, J = 6 Hz, 1 H), 6.062 (s, 1 H), 3.835 (t, J = 6 Hz, 2 H), 2.317 (s, 3 H), 2.318 (t, J = 7.2 Hz, 2 H), 2.154 (s, 6 H), 1.767 (t, J = 7.2 Hz, 2 H); MS (m/e): 416.5 (M + 1). |
| 31 | 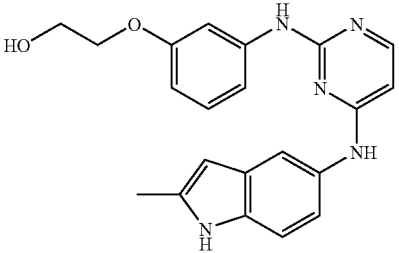 [SMILES: Cc1cc2cc(Nc3ccnc(Nc4cccc(OCCO)c4)n3)ccc2[nH]1] 2-(3-(4-(2-methyl-1H-indol-5-ylamino)pyrimidin-2-ylamino) phenoxy)ethanol | (CD$_3$OD): 10.902 (s, 1 H), 9.087 (s, 1 H), 8.986 (s, 1 H), 7.917 (d, J = 4 Hz, 1 H), 7.683 (s, 1 H), 7.405 (m, 2 H), 7.227 (m, 1 H), 7.104 (m, 1 H), 6.458 (d, J = 8 Hz, 1 H), 6.141 (s, 1 H), 6.050 (m, 2 H), 5.594 (m, 1 H), 3.873 (t, J = 5.6 Hz, 2 H), 3.653 (t, J = 6 Hz, 2 H), 2.376 (s, 3 H); MS (m/e): 375.4 (M + 1) |
| 32 | 2-(2-(4-(2-methyl-1H-indol-5-ylamino)pyrimidin-2-ylamino)phenoxy)ethanol 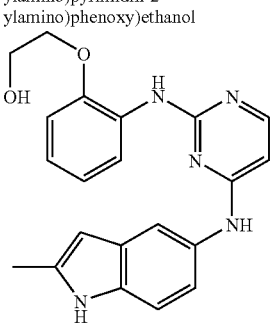 | (CD$_3$OD): 10.851 (s, 1 H), 9.117 (s, 1 H), 8.431 (d, J = 8.0 Hz 1 H), 7.938 (d, J = 6.0 Hz, 1 H), 7.869 (s, 1 H), 7.689 (br, 1 H), 7.228 (d, J = 8.8 Hz, 1 H), 6.983~7.053 (m, 2 H), 6.836-6.923 (m, 2 H), 6.147 (d, J = 6.0 Hz 1 H), 6.079 (s, 1 H), 5.137 (t, J = 5.6 Hz 1 H), 4.061 (q, J = 11.2 Hz, 1.2 Hz 2 H), 3.767 (q, J = 9.6 Hz, 5.6 Hz 2 H), 2.389 (s, 3 H); MS (m/e): 376.3 (M + 1). |

| Compound | Name/Structure | ¹H NMR (400 MHz, δ ppm)/MS |
|---|---|---|
| 33 | N4-(2-methyl-1H-indol-5-yl)-N2-(2-(2-morpholinoethoxy)phenyl) pyrimidine-2,4-diamine | (CD$_3$OD): 10.845 (s, 1 H), 9.112 (s, 1 H), 8.377 (d, J = 7.6 Hz 1 H), 7.935 (d, J = 6.0 Hz, 1 H), 7.823 (s, 1 H), 7.647 (br, 1 H), 7.219 (d, J = 8.8 Hz, 1 H), 7.061 (d, J = 8 Hz , 2 H), 6.889~6.950 (m, 2 H), 6.147 (d, J = 6.0 Hz 1 H), 6.074 (s, 1 H), 4.182 (t, J = 6.0 Hz 2 H), 3.592 (t, J = 4.8 Hz, 4 H), 2.692 (t, J = 5.2 Hz, 2 H), 2.471 (br, 4 H), 2.388 (s, 3 H); MS (m/e): 445.3 (M + 1). |
| 34 | N-methyl-3-(4-(2-methyl-1H-indol-5-ylamino)pyrimidin-2-ylamino)benzamide | (DMSO-d$_6$): δ 11.015 (s, 1 H), 10.776 (s, 1 H), 10.593 (s, 1 H), 8.493 (d, J = 4 Hz, 1 H), 7.938 (m, 2 H), 7.803 (d, J = 2 Hz, 1 H), 7.651 (m, 2 H), 7.374 (m, 1 H), 7.210 (m, 2 H), 6.467 (m 1 H), 6.046 (s, 1 H), 2.779 (d, 4.4 Hz, 3 H), 2.379 (s, 3 H); MS (m/e): 373.4 (M + 1). |
| 35 | 3-(4-(2-methyl-1H-indol-5-ylamino)pyrimidin-2-ylamino)-N-(2-(piperidin-1-yl)ethyl)benzamide | (CD$_3$OD): 10.832 (s, 1 H), 9.156 (s, 1 H), 9.056 (s, 1 H), 8.157 (s, 1 H), 8.054 (s, 1 H), 7.946 (m, 2 H), 7.700 (b, 1 H), 7.319 (m, 2 H), 7.199 (m, 2 H), 6.159 (s, 1 H), 6.052 (s, 1 H), 3.180 (t, J = 5.6 Hz, 2 H), 2.378 (s, 3 H), 1.480 (s, 6 H), 1.372 (s, 4 H), 1.229 (s, 2 H). MS (m/e): 469.6 (M + 1) |
| 36 | N-(2-(dimethylamino)ethyl)-3-(4-(2-methyl-1H-indol-5-ylamino)pyrimidin-2-ylamino)benzamide | (CD$_3$OD): 10.846 (s, 1 H), 9.149 (s, 1 H), 9.077 (s, 1 H), 8.181 (t, J = 5.6 Hz, 1 H), 8.036 (m, 2 H), 7.934 (m, 1 H), 7.706 (b, 1 H), 7.340 (m, 1 H), 7.270 (m, 1 H), 7.203 (m, 1 H), 7.137 (m, 1 H), 6.160 (d, J = 5.6 Hz, 1 H), 6.054 (s, 1 H), 3.313 (t, J = 6.4 Hz, 2 H), 3.175 (t, J = 5.6 Hz, 2 H), 2.376 (s, 3 H), 2.175 (s, 6 H). MS (m/e): 429.5 (M + 1) |

-continued

| Compound | Name/Structure | ¹H NMR (400 MHz, δ ppm)/MS |
|---|---|---|
| 37 | N2-(3-(4-methoxyphenyl)-1H-pyrazol-5-yl)-N4-(2-methyl-1H-indol-5-yl)pyrimidine-2,4-diamine | (DMSO-$d_6$): δ 12.354 (s, 1 H), 10.911 (s, 1 H), 8.985 (br, 2 H), 7.901 (s, 1 H), 7.599 (br, 2 H), 7.259 (d, J = 8.4 Hz, 1 H), 7.037 (s, 1 H), 6.941-6.913 (m, 2 H), 6.099 (br, 2 H), 3.787 (s, 3 H), 2.493 (s, 3 H); MS (m/e): 412.8 (M + 1). |
| 38 | N-(3-ethynylphenyl)-4-(2-methyl-1H-indol-5-yloxy)pyrimidin-2-amine | (CD$_3$OD): 8.190 (d, J = 6.0 Hz, 1 H), 8.098 (s, 1 H), 7.612 (s, 1 H), 7.489 (d, J = 8.0 Hz, 1 H), 7.339-7.284 (m, 2 H), 7.053 (t, J = 8.4 Hz, 1 H), 6.937 (dd, J = 8.4 Hz, 2.0 Hz, 2 H), 6.294 (d, J = 6.0 Hz, 2 H), 6.262 (s, 1 H), 2.495 (s, 3 H); MS (m/e): 341.1 (M + 1) |
| 39 | N-(4-methoxyphenyl)-4-(2-methyl-1H-indol-5-yloxy)pyrimidin-2-amine | (CD$_3$OD): 8.198 (d, J = 6.4 Hz, 1 H), 7.974 (s, 1 H), 7.363-7.283 (m, 2 H), 6.935 (m, 2 H), 6.742 (t, J = 8.4 Hz, 1 H), 6.260 (s, 1 H), 6.200 (d, J = 5.6 Hz, 1 H), 3.771 (s, 3 H), 2.493 (s, 3 H). MS (m/e): 347.2 (M + 1). |
| 41 | 4-(2-methyl-1H-indol-5-yloxy)-N-(4-phenoxyphenyl)pyrimidin-2-amine | (CD$_3$OD): 8.201 (d, J = 5.6 Hz, 1 H), 7.373 (m, J = 8.8-5.2 Hz, 4 H), 7.188 (d, J = 2.0 Hz, 1 H), 7.081 (t, J = 7.2-6.8 Hz, 1 H), 6.989 (d, J = 3.2 Hz, 2 H), 6.890 (d, J = 8.4 Hz, J = 2.0 Hz, 1 H), 6.644 (d, J = 9.2 Hz, 2 H), 6.323 (d, J = 6.4 Hz, 1 H), 6.137 (s, 1 H), 2.376 (s, 3 H). MS (m/e): 409.3 (M + 1). |
| 42 | N-(3-methoxyphenyl)-4-(2-methyl-1H-indol-5-yloxy)pyrimidin-2-amine | (CD$_3$OD): 8.236 (d, J = 5.2 Hz, 1 H), 7.983 (s, 1 H), 7.314-7.283 (m, 2 H), 7.239 (br, 1 H), 7.063 (t, J = 8.0 Hz, 1 H), 6.981 (d, J = 8.0 Hz, 1 H), 6.981 (dd, J = 8.8 Hz, 2.0 Hz, 1 H), 6.528 (d, J = 8.0 Hz, 1 H), 6.278-6.253 (m, 1 H), 3.571 (s, 1 H), 2.493 (s, 3 H). MS (m/e): 347.2 (M + 1). |

| Compound | Name/Structure | $^1$H NMR (400 MHz, δ ppm)/MS |
|---|---|---|
| 43 | 4-(2-methyl-1H-indol-5-yloxy)-N-(3-(3-(thiomorpholino-1',1'-dioxide)propoxy)phenyl)pyrimidin-2-amine 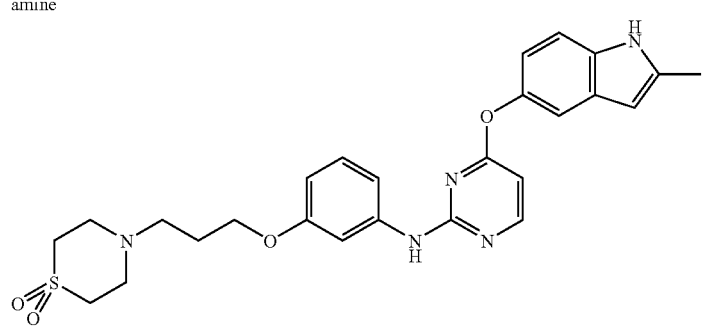 | (CD$_3$OD): 8.298 (s, 1 H), 7.996 (d, J = 5.6 Hz, 1 H), 7.385 (d, J = 8.4 Hz, 1 H), 7.197 (t, J = 8.0 Hz, 1 H), 7.094 (d, J = 8.4 Hz, 2 H), 6.791 (s, 1 H), 6.543 (d, J = 8.0 Hz, 1 H), 6.333 (s, 1 H), 5.995 (d, J = 6.0 Hz, 1 H), 5.321 (s, 1 H), 3.974 (t, J = 5.6 Hz, 1 H), 3.077 (m, 8 H), 2.699 (t, J = 6.8 Hz, 1 H), 2.468 (s, 3 H), 1.926 (t, J = 6.8 Hz, 2 H); |
| 44 | N-methyl-3-(4-(2-methyl-1H-indol-5-yloxy)pyrimidin-2-ylamino)benzamide 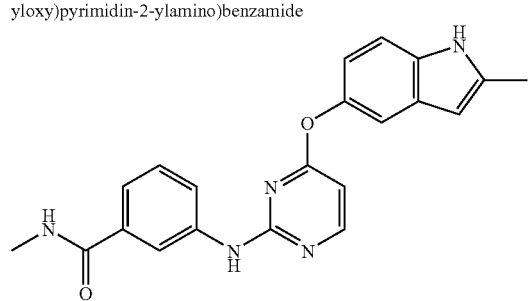 | (DMSO-d$_6$): 11.130 (s, 1 H), 9.631 (s, 1 H), 8.324 (d, J = 4.2 Hz, 1 H), 8.309 (s, 1 H), 7.994 (s, 1 H), 7.741 (s, 1 H), 7.308 (d, J = 9.2 Hz, 1 H), 7.219 (d, J = 1.6 Hz, 1 H), 7.052 (t, J = 2.0-0.8 Hz, 2 H), 6.932 (m, 1 H), 6.272 (d, J = 3.6 Hz, 1 H), 6.140 (d, J = 4.2 Hz, 1 H), 5.249 (s, 1 H), 2.801 (s, 3 H), 2.437 (s, 3 H), 2.401 (m, 2 H); MS (m/e): 374.3 (M + 1) |
| 45 | trifluoro-N-(4-(4-(2-methyl-1H-indol-5-yloxy)pyrimidin-2-ylamino)phenyl)methanesulfonamide 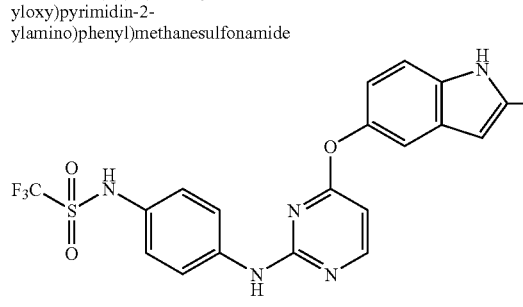 | (DMSO-d$_6$): 11.248 (s, 1 H), 9.304 (s, 1 H), 9.153 (s, 1 H), 7.960 (s, 1 H), 7.913 (d, J = 6.0 Hz, 1 H), 7.543 (d, J = 4.4 Hz, 2 H), 7.132 (d, J = 8.4 Hz 1 H), 7.063 (m, 1 H), 6.910 (t, J = 3.6 Hz, 2 H), 6.217 (s, 1 H), 6.106 (t, J = 1.6-2.4 Hz, 1 H), 2.411 (s, 3 H) MS (m/e): 464.4 (M + 1) |
| 46 | (S)-4-(2-methyl-1H-indol-5-yloxy)-N-(3-(pyrrolidin-3-yloxy)phenyl)pyrimidin-2-amine 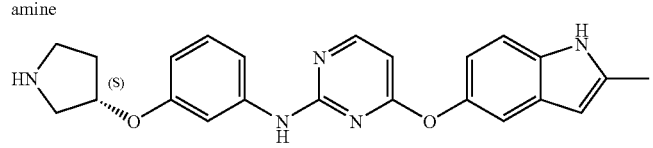 | (DMSO-d6): 11.122 (s, 1 H), 9.515 (s, 1 H), 8.306 (d, J = 5.6 Hz, 1 H), 7.156-7.332 (m, 4 H), 6.951 (t, J = 8.0 Hz, 1 H), 6.827 (dd, J = 8.4 Hz, 2.0 Hz, 1 H), 6.427 (dd, J = 8.4 Hz, 2.0 Hz, 1 H), 6.267 (d, J = 6.0 Hz, 1 H), 6.139 (s, 1 H), 6.639 (m, 2 H), 4.652-4.711 (m, 1 H), 2.964-3.154 (m, 4 H), 2.401 (s, 3 H), 1.958-1.993 (m, 1 H), 1.825-1.898 (m, 1 H); MS (m/e): 402.4 (M + 1) |
| 47 | 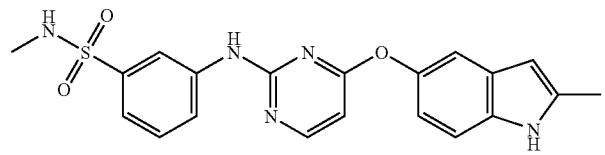 N-methyl-3-(4-(2-methyl-1H-indol-5-yloxy)pyrimidin-2-ylamino)benzenesulfonamide | (CDCl$_3$): 8.290 (d, 1 H), 8.115 (s, 1 H), 7.994 (s, 1 H), 7.504 (d, J = 8, 1 H), 7.409 (m, 2 H), 7.247 (d, J = 8, 1 H), 6.958 (m, J = 10.8), 6.403 (d, J = 5.6, 1 H), 6.254 (s, 1 H). 2.505 (s, 3 H), 2.478 (d, J = 5.6, 3 H). MS (m/e): 410.1 (M + 1) |

| Compound | Name/Structure | ¹H NMR (400 MHz, δ ppm)/MS |
|---|---|---|
| 48 | N-(4-(4-(2-methyl-1H-indol-5-yloxy)pyrimidin-2-ylamino)phenyl)methanesulfonamide | (CD₃OD): 11.204 (s, 1 H), 9.120 (s, 1 H), 8.837 (s, 1 H), 7.959 (d, J = 5.6 Hz, 1 H), 7.791 (d, J = 6.8 Hz, 2 H), 7.144 (s, 1 H), 7.026 (d, J = 7.6 Hz, 2 H), 6.922 (d, J = 7.2 Hz, 1 H), 6.210 (s, 1 H), 6.115 (s, 1 H), 4.007 (s, 3 H), 2.405 (s, 3 H); MS (m/e): 358.2 (M + 1). |
| 49 | 2-(3-(4-(2-methyl-1H-indol-5-yloxy)pyrimidin-2-ylamino)phenyl)-N-(2-morpholinoethyl)acetamide | (CD₃OD): 11.211 (s, 1 H), 8.935 (s, 1 H), 8.760 (s, 1 H), 7.959 (t, J = 8.8-5.6 Hz, 2 H), 7.376 (s, 1 H), 7.276 (d, J = 7.6 Hz, 1 H), 7.120 (t, J = 8.8-4.4 Hz, 1 H), 6.896 (t, J = 8.0 Hz, 2 H), 6.403 (t, J = 2.0-1.6 Hz, 1 H), 6.205 (s, 1 H), 6.004 (s, 1 H), 3.560 (s, 3 H), 2.405 (s, 3 H); MS (m/e): 364.2 (M + 1). |
| 50 | 4-(2-methyl-1H-indol-5-yloxy)-N-(3-(2-(methylsulfonyl)ethoxy)phenyl)pyrimidin-2-amine | (CD₃OD): 8.345 (s, 1 H), 8.049 (s, 1 H), 7.915 (d, J = 6.0 Hz, 1 H), 7.826 (s, 1 H), 7.58 (d, J = 8.8 Hz, 1 H), 7.535 (m, J = 7.2-6.8 Hz, 1 H), 7.433 (d, J = 7.6 Hz, 2 H), 7.103 (d, J = 7.6 Hz, 1 H), 6.241 (s, 1 H), 2.460 (s, 3 H); MS (m/e): 402.2 (M + 1). |
| 51 | N-methyl(3-(4-(2-methyl-1H-indol-5-yloxy)pyrimidin-2-ylamino)phenyl)methanesulfonamide | 11.217 (s, 1 H), 8.998 (s, 1 H), 8.789 (s, 1 H), 7.947 (d, J = 5.6 Hz, 1 H), 7.595 (m, J = 7.8-1.6 Hz, 2 H), 7.133 (d, J = 8.0 Hz, 2 H), 7.000,(s, 1 H), 6.721 (d, J = 2.8 Hz, 1 H), 6.211 (s, 1 H), 6.021 (s, 1 H), 2.403 (s, 3 H), 2.346 (s, 3 H); MS (m/e): 380.2 (M + 1). |
| 52 | N4-(4-fluoro-2-methyl-1H-indol-5-yl)-N2-(3-fluorophenyl) pyrimidine-2,4-diamine | (CD₃OD): 11.234 (s, 1 H), 9.256 (s, 1 H), 8.898 (s, 1 H), 7.966 (d, J = 5.6 Hz, 1 H), 7.752 (d, J = 8.4 Hz, 1 H), 7.393 (t, J = 8.4 Hz, 1 H), 7.133 (m, J = 8.4-3.6 Hz, 3 H), 6.612 (t, J = 7.6-1.2 Hz, 1 H), 6.239 (s, 1 H), 6.050 (s, 1 H), 2.402 (s, 3 H); MS (m/e): 352.2 (M + 1). |

-continued

| Compound | Name/Structure | ¹H NMR (400 MHz, δ ppm)/MS |
|---|---|---|
| 53 | N2-(3-chlorophenyl)-N4-(4-fluoro-2-methyl-1H-indol-5-yl)pyrimidine-2,4-diamine 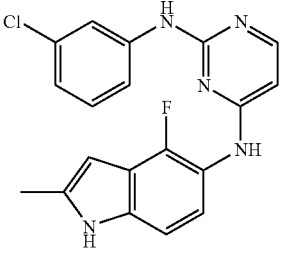 [SMILES: Cc1cc2c(F)c(Nc3ccnc(Nc4cccc(Cl)c4)n3)ccc2[nH]1] | (CD₃OD): 11.221 (s, 1 H), 8.965 (s, 1 H), 8.775 (s, 1 H), 7.927 (d, J = 6.0 Hz, 1 H), 7.619 (d, J = 8.0 Hz, 2 H), 7.128 (m, J = 8.0-7.6 Hz, 2 H), 6.958 (d, J = 7.8 Hz, 2 H), 6.210 (s, 1 H), 2.411 (s, 3 H); MS (m/e): 368.2 (m/e) (M + 1). |
| 54 | 2-(4-(4-fluoro-2-methyl-1H-indol-5-ylamino)pyrimidin-2-ylamino)benzonitrile 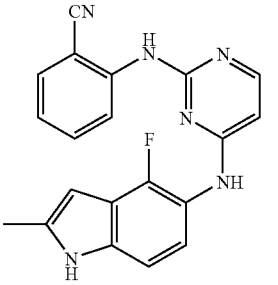 [SMILES: Cc1cc2c(F)c(Nc3ccnc(Nc4ccccc4C#N)n3)ccc2[nH]1] | (CD₃OD): 11.248 (s, 1 H), 9.412 (s, 1 H), 8.959 (s, 1 H), 8.208 (s, 1 H), 7.936 (d, J = 7.2 Hz, 1 H), 7.562 (d, J = 5.6 Hz, 1 H), 7.287 (s, 2 H), 7.164 (d, J = 8.4 Hz, 2 H), 6.233 (s, 1 H), 6.075 (s, 1 H), 2.399 (s, 3 H); MS (m/e): 359.2 (M + 1). |
| 55 | N2-(3,5-dimethylphenyl)-N4-(4-fluoro-2-methyl-1H-indol-5-yl)pyrimidine-2,4-diamine 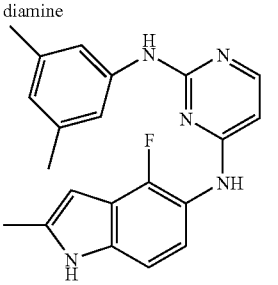 | (CD₃OD): 11.200 (s, 1 H), 8.806 (s, 1 H), 8.745 (s, 1 H), 7.911 (d, J = 6.0 Hz, 1 H), 7.216 (s, 2 H) 7.117 (t, J = 8.8-7.8 Hz, 2 H), 6.396 (s, 1 H), 6.181 (s, 1 H), 6.010 (s, 1 H), 2.381 (s, 3 H); 1.985 (s, 6 H); MS (m/e): 362.3 (M + 1). |
| 56 | N4-(4-fluoro-2-methyl-1H-indol-5-yl)-N2-(2-(trifluoromethyl)phenyl)pyrimidine-2,4-diamine 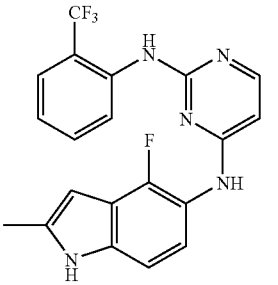 [SMILES: Cc1cc2c(F)c(Nc3ccnc(Nc4ccccc4C(F)(F)F)n3)ccc2[nH]1] | (CD₃OD): 11.211 (s, 1 H), 8.898 (s, 1 H), 8.209 (s, 1 H), 7.939 (t, J = 9.6-6.0 Hz, 2 H), 7.270 (t, J = 8.4-1.6 Hz, 1 H) 7.126 (s, 2 H), 6.998 (m, J = 2.0-1.2 Hz, 2 H), 6.225 (s, 1 H), 6.035 (s, 1 H), 2.402 (s, 3 H); MS (m/e): 402.2 (M + 1). |

-continued

| Compound | Name/Structure | $^1$H NMR (400 MHz, δ ppm)/MS |
|---|---|---|
| 57 | N2-(2-chlorophenyl)-N4-(4-fluoro-2-methyl-1H-indol-5-yl)pyrimidine-2,4-diamine<br />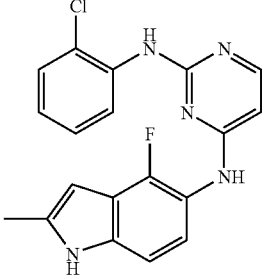 [SMILES: Cc1cc2c(F)c(Nc3ccnc(Nc4ccccc4Cl)n3)ccc2[nH]1] | (CD$_3$OD): 11.231 (s, 1 H), 8.922 (s, 1 H), 8.143 (d, J = 8.0 Hz ,1 H), 7.936 (s, J = 5.6 Hz, 1 H), 7.790 (s, 1 H), 7.424 (d, J = 8.4 Hz, 1 H), 7.101 (m, J = 8.4-7.2 Hz, 2 H), 6.993 (t, J = 8.8-7.2 Hz, 1 H), 6.216 (s, 1 H), 6.093 (m, J = 7.2-10.0 Hz, 1 H), 4.043 (s, J = 7.8 Hz, 1 H), 2.402 (s, 3 H); MS (m/e): 368.2 (M + 1). |
| 59 | N4-(4-fluoro-2-methyl-1H-indol-5-yl)-N2-(4-methoxyphenyl) pyrimidine-2,4-diamine<br />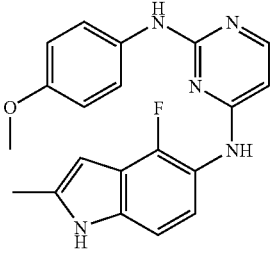 | 11.222 (s, 1 H), 8.796 (s, 1 H), 8.729 (s, 1 H), (CD$_3$OD): 7.959 (s, 1 H), 7.892 (d, J = 5.6 Hz, 1 H), 7.547 (d, J = 8.8 Hz, 2 H) 7.075 (s, 1 H), 6.646 (d, J = 7.6 Hz, 2 H), 6.222 (s, 1 H), 5.567 (s, 1 H), 3.658 (s, 3 H), 2.406 (s, 3 H); MS (m/e): 402.2 (M + 1). |
| 60 | N4-(4-fluoro-2-methyl-1H-indol-5-yl)-N2-(4-phenoxyphenyl) pyrimidine-2,4-diamine<br />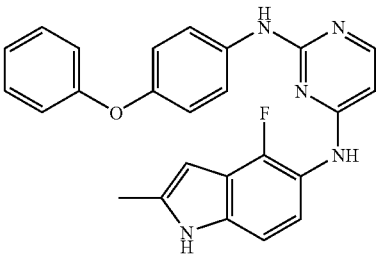 [SMILES: Cc1cc2c(F)c(Nc3ccnc(Nc4ccc(Oc5ccccc5)cc4)n3)ccc2[nH]1] | (CD$_3$OD): 11.190 (s, 1 H), 9.046 (s, 1 H), 8.801 (s, 1 H), 7.959 (s, 1 H), 7.931 (d, J = 6.0 Hz, 1 H), 7.681 (d, J = 7.2 Hz, 2 H), 7.361 (t, J = 8.0-7.6 Hz, 2 H), 7.114 (m, J = 8.4-7.2 Hz, 3 H), 6.903 (d, J = 8.0 Hz, 2 H), 6.755 (d, J = 7.2 Hz, 2 H), 6.179 (s, 1 H), 6.024 (s, 1 H), 2.338 (s, 3 H). MS (m/e): 426.2 (M + 1). |
| 61 | 2-(1-(3-(4-(4-fluoro-2-methyl-1H-indol-5-ylamino)pyrimidin-2-ylamino)benzyl)piperidin-4-yl)ethanol<br />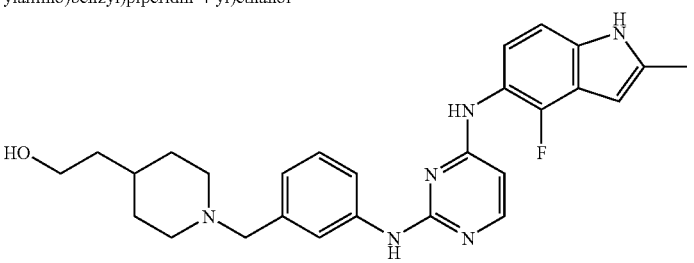 | (CD$_3$OD): 7.932 (s, 1 H), 7.885 (d, J = 5.6 Hz, 1 H), 7.331 (m, 1 H), 7.204 (m, 3 H), 7.103 (t, J = 7.2 Hz, 1 H), 6.958 (d, J = 7.6 Hz, 1 H), 6.251 (s, 1 H), 6.176 (m,1 H), 3.603-3.572 (m, 4 H), 3.068-3.041 (m, 2 H), 2.454 (s, 3 H), (m, 2 H), 2.197 (br, 2 H), 1.783-1.750 (m, 2 H), 1.563 (br, 2 H), 1.477 (m, 2 H), 1.311-1.275 (m, 2 H).<br />MS (m/e): 475.4 (M + 1) |
| 62 | N4-(4-fluoro-2-methyl-1H-indol-5-yl)-N2-(3-(3-(methylsulfonyl)propoxy)phenyl)pyrimidine-2,4-diamine<br />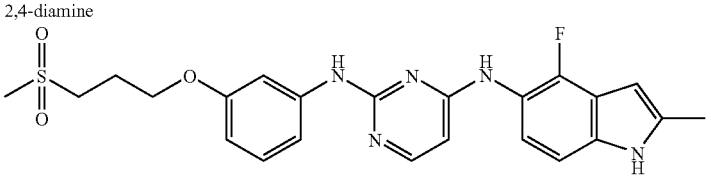 | (DMSO-d$_6$): 7.932 (d, J = 6.0 Hz, 1 H), 7.399 (s, 1 H), 7.393 (d, J = 6.8 Hz, 1 H), 7.099 (m, 2 H), 6.97 (m, 1 H), 6.416 (d, J = 8.0 Hz, 1 H), 6.207 (s, 1 H), 6.088 (s,lH), 3.84 (m, 2 H), 3.196 (m, 2 H), 3.010 (s, 3 H), 2.400 (s, 3 H), 2.014 (m, 2 H).<br />MS (m/e): 470.5 (M + 1) |

-continued

| Compound | Name/Structure | $^1$H NMR (400 MHz, δ ppm)/MS |
|---|---|---|
| 63 | 2-(3-(4-(4-fluoro-2-methyl-1H-indol-5-ylamino)pyrimidin-2-ylamino)phenoxy)ethanol 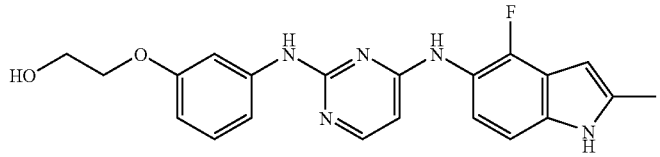 [SMILES: Cc1cc2c(F)c(Nc3ccnc(Nc4cccc(OCCO)c4)n3)ccc2[nH]1] | (DMSO-$d_6$): 7.938 (d, J = 6.0 Hz, 1 H), 7.347 (m, 2 H), 7.104 (m, 2 H), 6.950 (m, 1 H), 6.410 (d, J = 8.0 Hz, 1 H), 6.206 (s, 1 H), 6.088 (s, 1 H), 3.788 (m, 2 H), 3.630 (m, 2 H), 2.401 (s, 3 H). MS (m/e): 394.4 (M + 1). |
| 64 | N4-(4-fluoro-2-methyl-1H-indol-5-yl)-N2-(3-(piperidin-3-yloxy)phenyl)pyrimidine-2,4-diamine 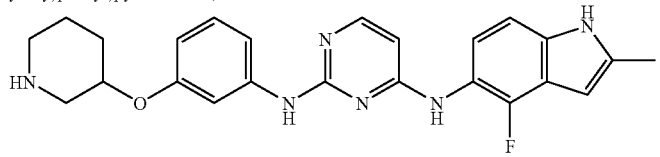 | (DMSO-$d_6$): 11.241 (s, 1 H), 8.966 (s, 1 H), 8.789 (s, 1 H), 7.929 (d, J = 5.6 Hz, 1 H), 7.378 (s, 1 H), 7.267 (d, J = 7.6 Hz, 1 H), 7.120-7.053 (m, 2 H), 6.964 (m, 1 H), 6.380 (d, J = 8.0 Hz, 1 H) 6.207 (s, 1 H) , 6.010 (s, 1 H), 4.010 (s, 1 H), 3.710 (m, 1 H); 3.554 (s, 2 H). 3.362 (m, 2 H) 2.506 (s, 3 H) 2.401 (m, 2 H) 1.234 (m, 2 H),MS (m/e): 433.2 (M + 1) |
| 65 | N4-(4-fluoro-2-methyl-1H-indol-5-yl)-N2-(3-((1-(methylsulfonyl)piperidin-4-yl)methoxy)phenyl)pyrimidine-2,4-diamine 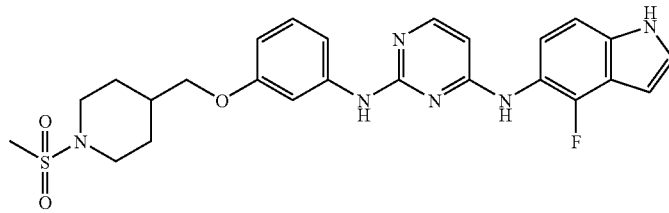 | (CD$_3$OD): 8.021 (d, J = 5.6 Hz, 1 H), 7.418 (s, 1 H), 7.220-7.051 (m, 3 H), 6.998 (m, 1 H), 6.612 (d, J = 7.4 Hz, 1 H) 6.267 (s, 1 H) , 5.800 (d, J = 5.6 Hz , 1 H), 3.960 (d, J = 5.2 Hz, 2 H), 3.810 (m, 2 H); 3.362 (m, 2 H).2.826 (s, 3 H), 2.506 (s, 3 H) 1.556 (m, 2 H), 1.452 (m 1 H) 1.234 (m, 2 H) |
| 66 | 1-(3-(4-(4-fluoro-2-methyl-1H-indol-5-yloxy)pyrimidin-2-ylamino)benzyl)piperidin-4-ol 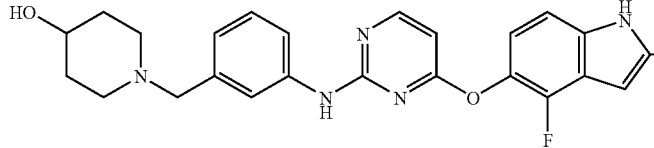 | (CD$_3$OD): 8.247 (d, J = 5.6 Hz, 1 H), 7.378 (s, 1 H), 7.160-7.108 (m, 2 H), 6.956 (t, J = 8.0 Hz, 1 H), 6.895-6.825 (m, 2 H), 6.450 (d, J = 5.6 Hz, 1 H), 6.247 (s, 1 H), 3.031 (s, 1 H), 2.690-2.663 (m, 2 H), 2.455 (s, 3 H), 2.069-2.042 (m, 2 H), 1.815-1.716 (m, 2 H), 1.562-1.483 (m, 2 H); MS (m/e): 448.5 (M + 1) |
| 67 | 4-(4-fluoro-2-methyl-1H-indol-5-yloxy)-N-(3-(methylsulfonyl)phenyl)pyrimidin-2-amine 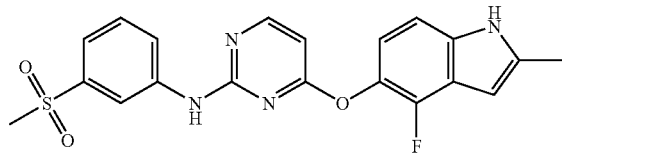 | (CD$_3$OD): 8.292 (d, J = 5.6 Hz, 1 H), 8.005 (s, 1 H), 7.69 1 (d, J = 7.2 Hz, 1 H), 7.34 1 (d, J = 7.2 Hz, 1 H), 7.102 (d, J = 8.8 Hz, 1 H), 7.013 (t, J = 7.2 Hz, 1 H), 6.849 (t, J = 8.0 Hz, 1 H), 6.482 (d, J = 5.6 Hz, 1 H), 6.221 (s, 1 H), 2.900 (s, 3 H), 2.432 (s, 3 H); MS (m/e): 413.4 (M + 1) |
| 68 | N-cyclopropyl-2-(3-(4-(4-fluoro-2-methyl-1H-indol-5-yloxy)pyrimidin-2-ylamino)phenyl)acetamide 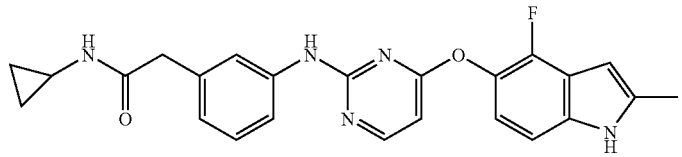 [SMILES: Cc1cc2c(F)c(Oc3ccnc(Nc4cccc(CC(=O)NC5CC5)c4)n3)ccc2[nH]1] | (DMSO-$d_6$): 7.947 (m, 2 H), 7.298 (m, 2 H), 7.154 (d, J = 8.4 Hz, 1 H), 6.947 (m, 1 H), 6.755 (m, 1 H), 6.775 (d, J = 8.0 Hz, 1 H), 6.441 (d, J = 5.6 Hz, 1 H), 6.240 (s, 1 H), 3.027 (s, 2 H), 2.593 (m, 1 H), 2.499 (s, 3 H), 0.596 (m, 2 H), 0.390 (m, 2 H). MS (m/e): 432.5 (M + 1) |

| Compound | Name/Structure | ¹H NMR (400 MHz, δ ppm)/MS |
|---|---|---|
| 69 | (E)-3-(3-(4-(4-fluoro-2-methyl-1H-indol-5-yloxy)pyrimidin-2-ylamino)phenyl)-N-methylacrylamide 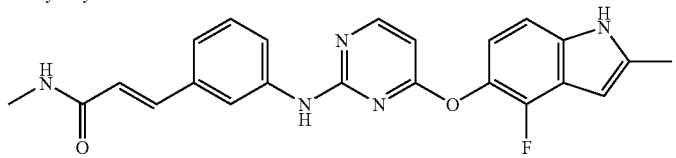 | (DMSO-d₆) 11.550 (s, 1 H), 9.791 (s, 1 H), 8.385 (d, J = 5.2, 1 H), 8.114 (d, J = 4.8, 1 H), 7.432 (d, J = 7.2, 2 H), 7.214 (d, J = 10, 1 H), 7.184 (d, J = 3.2, 1 H), 7.083 (d, J = 8, 2 H), 6.942 (m, J = 16, 1 H), 6.533 (d, J = 5.6, 1 H, 6.402 (d, J = 15.6), 6.253 (s, 1 H), 2.687 (d, J = 4.8, 3 H), 2.440 (s, 3 H). MS (m/e): 418.2 (M + 1) |
| 70 | 3-(3-(4-(4-fluoro-2-methyl-1H-indol-5-yloxy)pyrimidin-2-ylamino)phenyl)-N,N-dimethylpropanamide 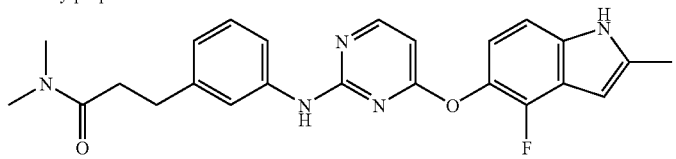 | (DMSO-d₆) 11.397 (s, 1 H), 9.420 (s, 1 H), 8.334 (d, J = 5.6, 1 H), 7.290 (s, 1 H), 7.241 (d, J = 7.2, 1 H), 7.152 (d, J = 8.8, 1 H), 6.919 (m, J = 15.2, 1 H), 6.803 (m, J = 15.6, 1 H), 6.652 (d, J = 6.8, 1 H), 6.451 (d, J = 5.6, 1 H), 6.218 (s, 1 H), 2.860 (s, 3 H), 2.795 (s, 3 H), 2.449 (m, J = 14.8, 2 H), 2.399 (s, 3 H), 2.338 (m, J = 14.8, 2 H). MS (m/e): 434.2 (M + 1) |
| 71 | N-methyl-3-(4-(2-methyl-1H-indol-5-ylamino)pyrimidin-2-ylamino)benzamide 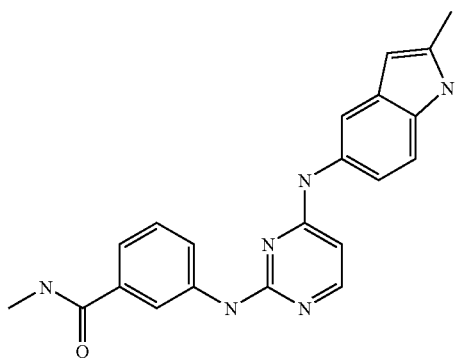 | MS (m/e): 372.4 (M) |
| 72 | N2-(2-fluorophenyl)-N4-(2-methyl-1H-indol-5-yl)pyrimidine-2,4-diamine 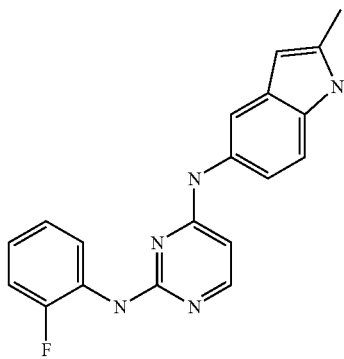 | MS (m/e): 350.1 (M + 1) |
| 73 | 3-(4-(2-methyl-1H-indol-5-ylamino)pyrimidin-2-ylamino)benzonitrile | MS (m/e): 341.2 (M + 1) |

| Compound | Name/Structure | 1H NMR (400 MHz, δ ppm)/MS |
|---|---|---|
| 74 | 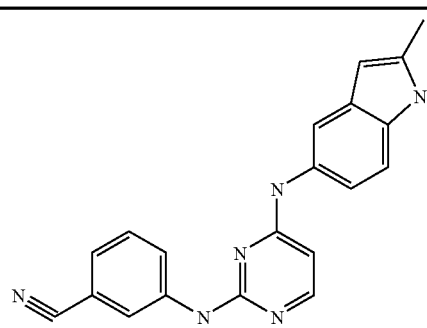N4-(2-methyl-1H-indol-5-yl)-N2-(3-(methylthio)phenyl)pyrimidine-2,4-diamine | MS (m/e): 362.3 (M + 1) |
| 75 | 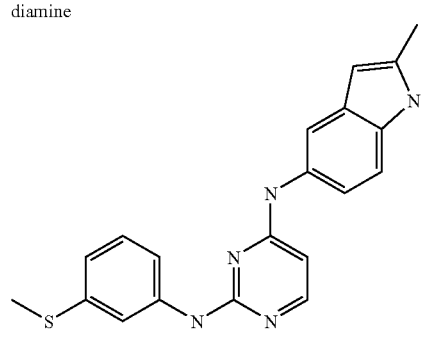N,N-dimethyl-3-(4-(2-methyl-1H-indol-5-ylamino)pyrimidin-2-ylamino)benzenesulfonamide | MS (m/e): 423.5 (M + 1) |
| 76 | 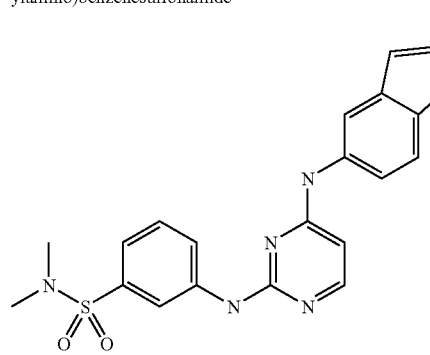N4-(2-methyl-1H-indol-5-yl)-N2-(3-(morpholinosulfonyl)phenyl)pyrimidine-2,4-diamine | MS (m/e): 465.4 (M + 1) |
| 77 | 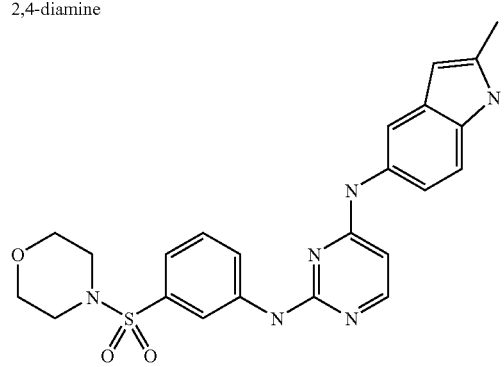N2-(3,4-dimethoxyphenyl)-N4-(2-methyl-1H-indol-5-yl)pyrimidine-2,4-diamine | MS (m/e): 376.3 (M + 1) |

| Compound | Name/Structure | ¹H NMR (400 MHz, δ ppm)/MS |
|---|---|---|
| | *(structure: 2-methyl-1H-indol-5-yl and 3,4-dimethoxyphenyl pyrimidine-2,4-diamine)* | |
| 78 | N2-(4-chlorophenyl)-N4-(2-methyl-1H-indol-5-yl)pyrimidine-2,4-diamine | MS (m/e): 350.3 (M + 1) |
| 79 | N2-(2,4-difluorophenyl)-N4-(2-methyl-1H-indol-5-yl)pyrimidine-2,4-diamine | MS (m/e): 352.2 (M + 1) |
| 80 | N2-(3-chloro-2-fluorophenyl)-N4-(2-methyl-1H-indol-5-yl)pyrimidine-2,4-diamine | MS (m/e): 368.3 (M + 1) |
| 81 | N2-(1H-indol-4-yl)-N4-(2-methyl-1H-indol-5-yl)pyrimidine-2,4-diamine | MS (m/e): 355.3 (M + 1) |

| Compound | Name/Structure | ¹H NMR (400 MHz, δ ppm)/MS |
|---|---|---|
| 82 | N2-(4-(3-(dimethylamino)propoxy)phenyl)-N4-(2-methyl-1H-indol-5-yl)pyrimidine-2,4-diamine | MS (m/e): 417.4 (M + 1) |
| 83 | 2-(4-(4-(2-methyl-1H-indol-5-ylamino)pyrimidin-2-ylamino)phenoxy)ethanol | MS (m/e): 376.3 (M + 1) |
| 84 | N2-(3-chloro-4-fluorophenyl)-N4-(2-methyl-1H-indol-5-yl)pyrimidine-2,4-diamine | MS (m/e): 368.3 (M + 1) |
| 85 | N2-(benzo[d][1,3]dioxol-5-yl)-N4-(2-methyl-1H-indol-5-yl)pyrimidine-2,4-diamine | MS (m/e): 360.3 (M + 1) |
| 86 | (1-(3-(4-(2-methyl-1H-indol-5-ylamino)pyrimidin-2-ylamino)benzyl)piperidin-4-yl)methanol | MS (m/e): 443.4 (M + 1) |
| 87 | N4-(2-methyl-1H-indol-5-yl)-N2-(3-(2-(4-(methylsulfonyl)piperazin-1-yl)ethoxy)phenyl)pyrimidine-2,4-diamine | MS (m/e): 521.2 (M) |
| 88 | 3-(4-(2-methyl-1H-indol-5-ylamino)pyrimidin-2-ylamino)-N-propylbenzenesulfonamide | MS (m/e): 437.3 (M + 1) |

| Compound | Name/Structure | ¹H NMR (400 MHz, δ ppm)/MS |
|---|---|---|
| | 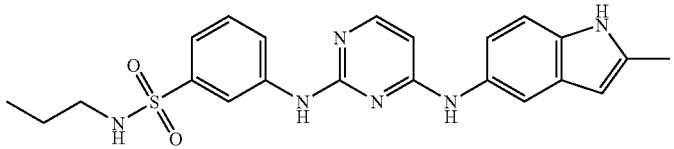 [SMILES: CCCNS(=O)(=O)c1cccc(Nc2nccc(Nc3ccc4[nH]c(C)cc4c3)n2)c1] | |
| 89 | N2-(2-chloro-4-fluorophenyl)-N4-(2-methyl-1H-indol-5-yl)pyrimidine-2,4-diamine<br>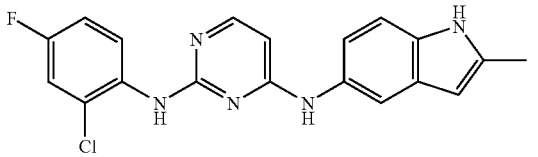 [SMILES: Cc1cc2cc(Nc3ccnc(Nc4ccc(F)cc4Cl)n3)ccc2[nH]1] | MS (m/e): 368.1 (M + 1) |
| 90 | 2-chloro-4-fluoro-5-(4-(2-methyl-1H-indol-5-ylamino)pyrimidin-2-ylamino)phenol<br>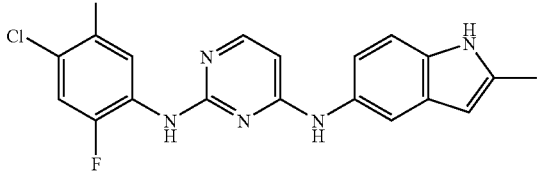 | MS (m/e): 384.3 (M + 1) |
| 91 | N2-(4-chloro-2-fluorophenyl)-N4-(2-methyl-1H-indol-5-yl)pyrimidine-2,4-diamine<br>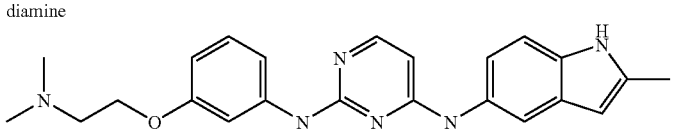 | MS (m/e): 368.3 (M + 1) |
| 92 | N2-(3-(2-(dimethylamino)ethoxy)phenyl)-N4-(2-methyl-1H-indol-5-yl)pyrimidine-2,4-diamine<br>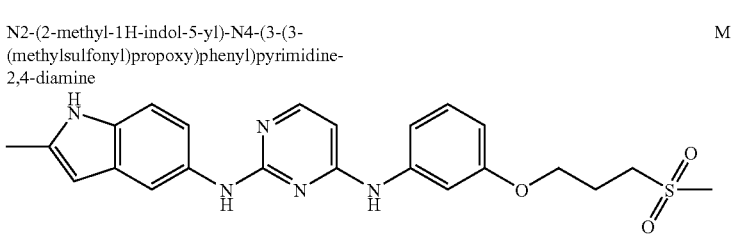 | MS (m/e): 403.4 (M + 1) |
| 93 | N2-(2-methyl-1H-indol-5-yl)-N4-(3-(3-(methylsulfonyl)propoxy)phenyl)pyrimidine-2,4-diamine<br>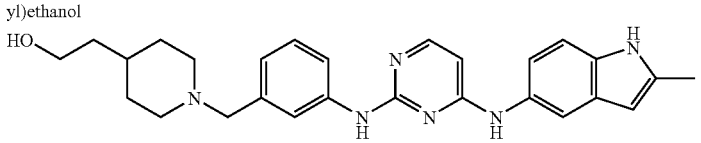 | MS (m/e): 452.3 (M + 1) |
| 94 | 2-(1-(3-(4-(2-methyl-1H-indol-5-ylamino)pyrimidin-2-ylamino)benzyl)piperidin-4-yl)ethanol | MS (m/e): 457.4 (M + 1) |

| Compound | Name/Structure | ¹H NMR (400 MHz, δ ppm)/MS |
|---|---|---|
| 95 | N4-(2-methyl-1H-indol-5-yl)-N2-(3-(piperidin-4-ylmethoxy)phenyl)pyrimidine-2,4-diamine | MS (m/e): 429.4 (M + 1) |
| 96 | N4-(2-methyl-1H-indol-5-yl)-N2-(3-(piperidin-3-yloxy)phenyl)pyrimidine-2,4-diamine | MS (m/e): 416.4 (M + 1) |
| 97 | 1-(3-(4-(2-methyl-1H-indol-5-ylamino)pyrimidin-2-ylamino)benzyl)piperidin-4-ol | MS (m/e): 429.4 (M + 1) |
| 98 | (S)-N4-(2-methyl-1H-indol-5-yl)-N2-(3-(pyrrolidin-3-yloxy)phenyl)pyrimidine-2,4-diamine | MS (m/e): 401.4 (M + 1) |
| 99 | (S)-N4-(2-methyl-1H-indol-5-yl)-N2-(3-(1-(methylsulfonyl)pyrrolidin-3-yloxy)phenyl)pyrimidine-2,4-diamine | MS (m/e): 479.5 (M + 1) |
| 100 | N4-(2-methyl-1H-indol-5-yl)-N2-(3-(piperidin-4-yloxy)phenyl)pyrimidine-2,4-diamine | MS (m/e): 415.5 (M + 1) |
| 101 | N4-(2-methyl-1H-indol-5-yl)-N2-(3-(3-(4-(methylsulfonyl)piperazin-1-yl)propoxy)phenyl)pyrimidine-2,4-diamine | MS (m/e): 536.6 (M + 1) |

| Compound | Name/Structure | ¹H NMR (400 MHz, δ ppm)/MS |
|---|---|---|
| | (structure: methylsulfonyl-piperazine-propoxy-phenyl-NH-pyrimidine-NH-2-methylindole) | |
| 102 | N4-(2-methyl-1H-indol-5-yl)-N2-(3-(3-morpholinopropoxy)phenyl) pyrimidine-2,4-diamine | MS (m/e): 459.6 (M + 1) |
| 103 | (R)-N4-(2-methyl-1H-indol-5-yl)-N2-(3-(1-(methylsulfonyl)pyrrolidin-3-yloxy)phenyl)pyrimidine-2,4-diamine | MS (m/e): 479.5 (M + 1) |
| 104 | (E)-N,N-dimethyl-3-(3-(4-(2-methyl-1H-indol-5-ylamino)pyrimidin-2-ylamino)phenyl)acrylamide | MS (m/e): 413.2 (M + 1) |
| 105 | 4-(4-fluoro-2-methyl-1H-indol-5-yl)-N-(3-(3-(thiomorpholino-1',1'-dioxide)propoxy)phenyl)pyrimidin-2-amine | MS (m/e): 507.5 (M + 1) |
| 106 | N4-(2-methyl-1H-indol-5-yl)-N2-(3-(2-(methylamino)ethoxy)phenyl)pyrimidine-2,4-diamine | MS (m/e): 389.5 (M + 1) |
| 107 | 4-(4-fluoro-2-methyl-1H-indol-5-yloxy)-N-(3-(3-(thiomorpholino-1'-oxide)propoxy) phenyl) pyrimidin-2-amine | MS (m/e): 491.5 (M + 1) |

| Compound | Name/Structure | ¹H NMR (400 MHz, δ ppm)/MS |
|---|---|---|
| | *[structure: 2-methylindole-NH-pyrimidine-NH-phenyl-O-propyl-thiomorpholine S-oxide]* | |
| 108 | N-(2-(3-(4-(2-methyl-1H-indol-5-ylamino)pyrimidin-2-ylamino)phenoxy)ethyl)methanesulfonamide | MS (m/e): 453.4 (M + 1) |
| | *[structure: methanesulfonamide-ethoxy-phenyl-NH-pyrimidine-NH-2-methylindole]* | |
| 109 | N4-(2-methyl-1H-indol-5-yl)-N2-(3-(3-thiomorpholinopropoxy)phenyl)pyrimidine-2,4-diamine | MS (m/e): 475.5 (M + 1) |
| | *[structure: 2-methylindole-NH-pyrimidine-NH-phenyl-O-propyl-thiomorpholine]* | |
| 110 | trifluoro-N-(4-(4-(2-methyl-1H-indol-5-ylamino)pyrimidin-2-ylamino)phenyl)methanesulfonamide | MS (m/e): 463.4 (M-i-1) |
| | *[structure: F3C-SO2-NH-phenyl-NH-pyrimidine-NH-2-methylindole]* | |
| 111 | N4-(2-methyl-1H-indol-5-yl)-N2-(3-(2-thiomorpholinoethoxy)phenyl)pyrimidine-2,4-diamine | MS (m/e): 461.4 (M + 1) |
| | *[structure: thiomorpholine-ethoxy-phenyl-NH-pyrimidine-NH-2-methylindole]* | |
| 112 | N4-(2-methyl-1H-indol-5-yl)-N2-(3-(2-pyrrolidinethoxy)phenyl)pyrimidine-2,4-diamine | MS (m/e): 429.4 (M + 1) |

| Compound | Name/Structure | ¹H NMR (400 MHz, δ ppm)/MS |
|---|---|---|
| | 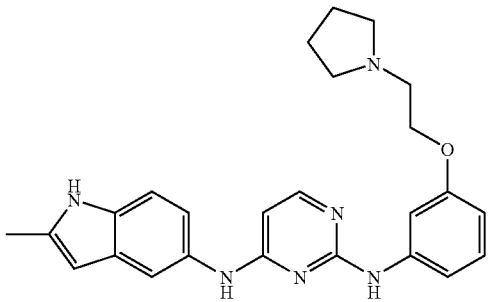 [SMILES: Cc1cc2cc(Nc3ccnc(Nc4cccc(OCCN5CCCC5)c4)n3)ccc2[nH]1] | |
| 113 | N4-(2-methyl-1H-indol-5-yl)-N2-(3-(2-morpholinoethylsulfonyl)phenyl)pyrimidine-2,4-diamine<br>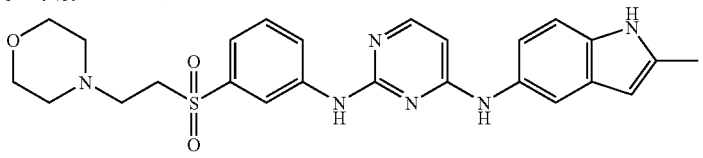 | MS (m/e): 493.1 (M + 1) |
| 114 | N4-(2-methyl-1H-indol-5-yl)-N2-(3-(2-(pyrrolidin-1-yl)ethylsulfonyl)phenyl)pyrimidine-2,4-diamine<br>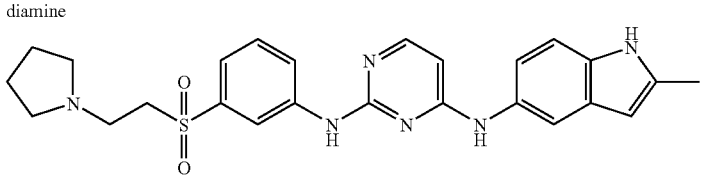 | MS (m/e): 477.1 (M + 1) |
| 115 | N4-(2-methyl-1H-indol-5-yl)-N2-(3-((4-(methylsulfonyl)piperazin-1-yl)methyl)phenyl)pyrimidine-2,4-diamine<br>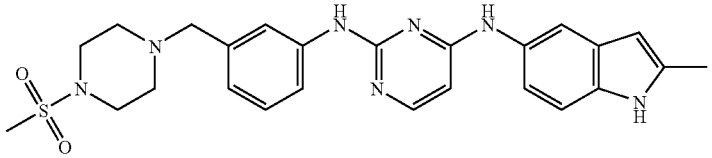 | MS (m/e): 492.4 (M + 1) |
| 116 | 2-(4-(3-(4-(2-methyl-1H-indol-5-ylamino)pyrimidin-2-ylamino)benzyl)piperazin-1-yl)ethanol<br>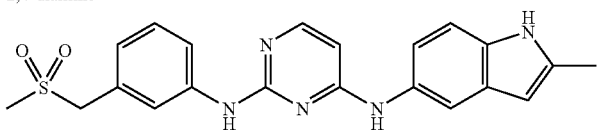 | MS (m/e): 458.5 (M + 1) |
| 117 | N4-(2-methyl-1H-indol-5-yl)-N2-(3-(methylsulfonylmethyl)phenyl)pyrimidine-2,4-diamine<br> | MS (m/e): 408.3 (M + 1) |
| 118 | N,N-dimethyl-3-(3-(4-(2-methyl-1H-indol-5-ylamino)pyrimidin-2-ylamino)phenyl)propanamide | MS (m/e): 415.5 (M + 1) |

| Compound | Name/Structure | ¹H NMR (400 MHz, δ ppm)/MS |
|---|---|---|
| | *[structure: 3-(dimethylamino)-3-oxopropyl phenyl linked via NH to pyrimidine linked via NH to 2-methyl-1H-indol-5-yl]* | |
| 119 | (E)-N-methyl-3-(3-(4-(2-methyl-1H-indol-5-ylamino)pyrimidin-2-ylamino)phenyl)acrylamide *[structure]* | MS (m/e): 399.2 (M + 1) |
| 120 | N4-(2-methyl-1H-indol-5-yl)-N2-(3-(tetrahydro-2H-pyran-4-yloxy)phenyl)pyrimidine-2,4-diamine *[structure]* | MS (m/e): 416.4 (M + 1) |
| 121 | N2-(3-(2-aminoethoxy)phenyl)-N4-(2-methyl-1H-indol-5-yl)pyrimidine-2,4-diamine *[structure]* | MS (m/e): 375.3 (M + 1) |
| 122 | N-(3-(4-(2-methyl-1H-indol-5-ylamino)pyrimidin-2-ylamino)benzyl)methanesulfonamide *[structure]* | MS (m/e): 423.4 (M + 1) |
| 123 | N-(2-hydroxyethyl)-3-(4-(2-methyl-1H-indol-5-ylamino)pyrimidin-2-ylamino)benzamide *[structure]* | MS (m/e): 403.2 (M + 1) |
| 124 | N-methyl-3-(3-(4-(2-methyl-1H-indol-5-ylamino)pyrimidin-2-ylamino)phenyl)propanamide | MS (m/e): 401.2 (M + 1) |

| Compound | Name/Structure | $^1$H NMR (400 MHz, δ ppm)/MS |
|---|---|---|
| | 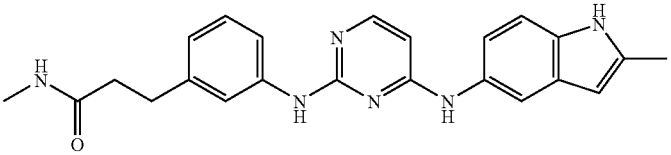 | |
| 125 | 3-(4-(2-methyl-1H-indol-5-ylamino)pyrimidin-2-ylamino)-N-(2-(methylamino)-2-oxoethyl)benzamide<br />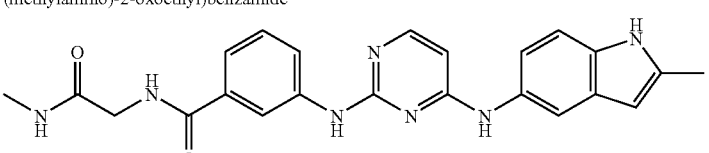 | MS (m/e): 430.2 (M + 1) |
| 126 | 3-(4-(2-methyl-1H-indol-5-ylamino)pyrimidin-2-ylamino)-N-(2-morpholinoethyl)benzamide<br />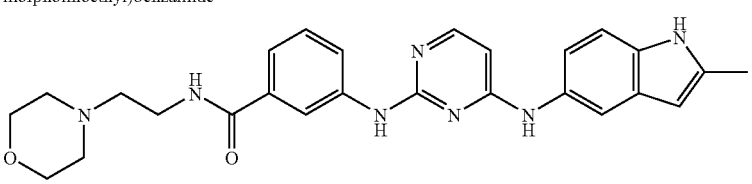 | MS (m/e): 472.3 (M + 1) |
| 127 | 3-(4-(2-methyl-1H-indol-5-ylamino)pyrimidin-2-ylamino)-N-(2-(piperidin-1-yl)ethyl)benzamide<br />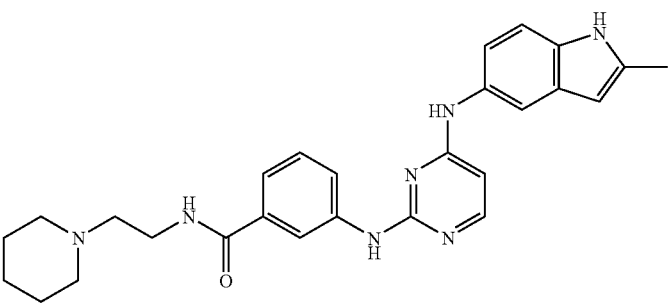 [SMILES: Cc1cc2cc(Nc3ccnc(Nc4cccc(C(=O)NCCN5CCCCC5)c4)n3)ccc2[nH]1] | MS (m/e): 470.1 (M + 1) |
| 128 | trifluoro-N-(3-(4-(2-methyl-1H-indol-5-ylamino)pyrimidin-2-yl amino)phenyl)methanesulfonamide<br />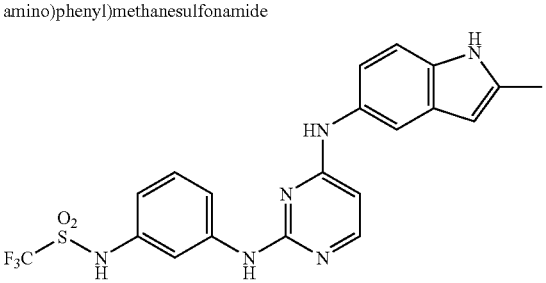 | MS (m/e): 463.0 (M + 1) |
| 129 | N-(2-methoxyethyl)-3-(4-(2-methyl-1H-indol-5-ylamino)pyrimidin-2-ylamino)benzamide | MS (m/e): 417.2 (M + 1) |

-continued

| Compound | Name/Structure | $^1$H NMR (400 MHz, δ ppm)/MS |
|---|---|---|
| 130 | N-(4-(4-(2-methyl-1H-indol-5-ylamino)pyrimidin-2-yl amino)phenyl)methanesulfonamide | MS (m/e): 409.1 (M + 1) |
| 131 | 2-(3-(4-(2-methyl-1H-indol-5-ylamino)pyrimidin-2-ylamino)phenyl)-N-(2-morpholinoethyl)acetamide | MS (m/e): 493.1 (M + 1) |
| 132 | N2-(6-methoxypyridin-3-yl)-N4-(2-methyl-1H-indol-5-yl)pyrimidine-2,4-diamine | MS (m/e): 347.4 (M + 1) |
| 133 | 2-methyl-N-(4-(2-methyl-1H-indol-5-yloxy)pyrimidin-2-yl)-1H-indol-5-amine | MS (m/e): 370.3 (M + 1) |
| 134 | N-(3-(3-(dimethylamino)propoxy)phenyl)-4-(2-methyl-1H-indol-5-yloxy)pyrimidin-2- | MS (m/e): 418.4 (M + 1) |

| Compound | Name/Structure | $^1$H NMR (400 MHz, δ ppm)/MS |
|---|---|---|
| | amine 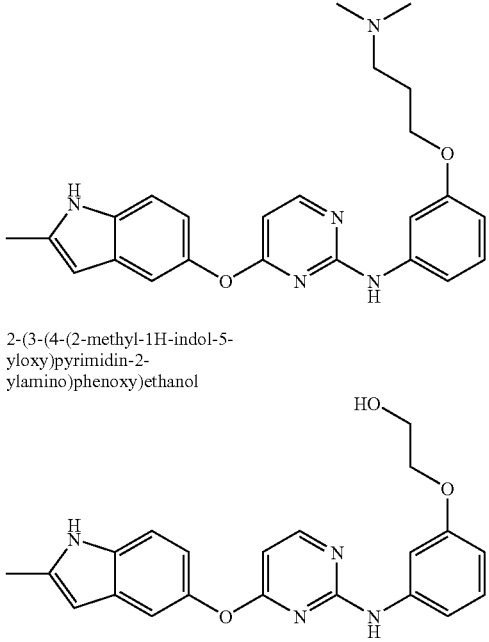 | |
| 135 | 2-(3-(4-(2-methyl-1H-indol-5-yloxy)pyrimidin-2-ylamino)phenoxy)ethanol 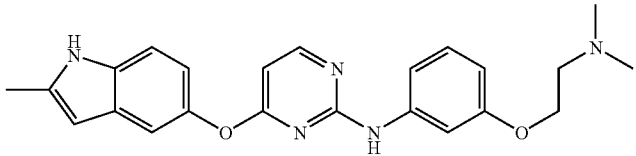 | MS (m/e): 377.4 (M + 1) |
| 136 | N-(3-(2-(dimethylamino)ethoxy)phenyl)-4-(2-methyl-1H-indol-5-yloxy)pyrimidin-2-amine 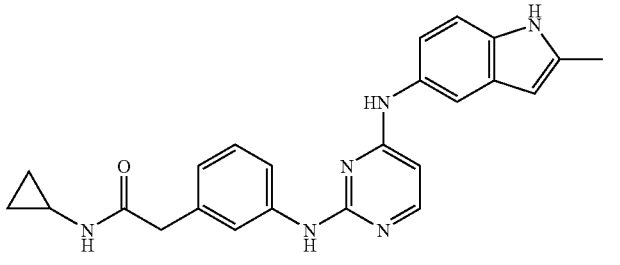 | MS (m/e): 404.4 (M + 1) |
| 137 | N-cyclopropyl-2-(3-(4-(2-methyl-1H-indol-5-yloxy)pyrimidin-2-ylamino)phenyl)acetamide 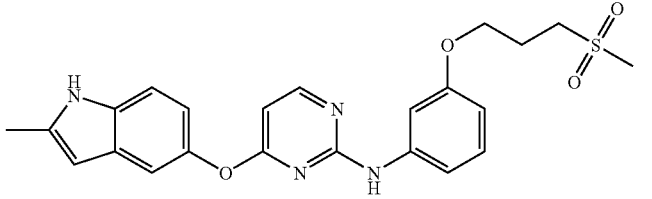 | MS (m/e): 414.4 (M + 1) |
| 138 | 4-(2-methyl-1H-indol-5-yloxy)-N-(3-(3-(methylsulfonyl)propoxy)phenyl)pyrimidin-2-amine  | MS (m/e): 453.4 (M + 1) |
| 139 | 4-(2-methyl-1H-indol-5-yloxy)-N-(3-(piperidin-4-ylmethoxy)phenyl)pyrimidin-2-amine | MS (m/e): 448.2 (M + 1) |

| Compound | Name/Structure | ¹H NMR (400 MHz, δ ppm)/MS |
|---|---|---|
| | 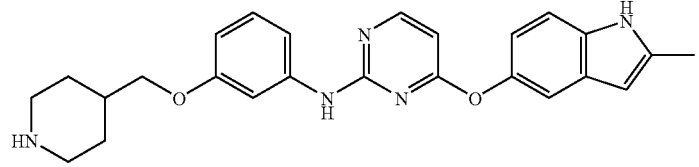 [SMILES: Cc1cc2cc(Oc3ccnc(Nc4cccc(OCC5CCNCC5)c4)n3)ccc2[nH]1] | |
| 140 | 4-(2-methyl-1H-indol-5-yloxy)-N-(3-(piperidin-3-yloxy)phenyl)pyrimidin-2-amine<br/>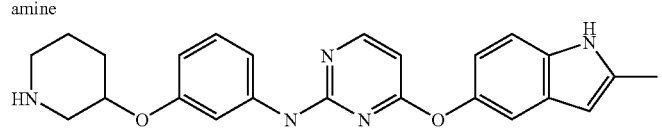 | MS (m/e): 416.2 (M + 1) |
| 141 | 4-(2-methyl-1H-indol-5-yloxy)-N-(3-(piperidin-4-yloxy)phenyl)pyrimidin-2-amine<br/>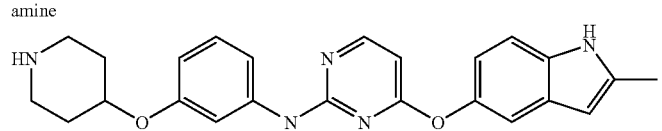 | MS (m/e): 416.4 (M + 1) |
| 142 | 4-(2-methyl-1H-indol-5-yloxy)-N-(3-(1-(methylsulfonyl)piperidin-4-yloxy)phenyl)pyrimidin-2-amine<br/>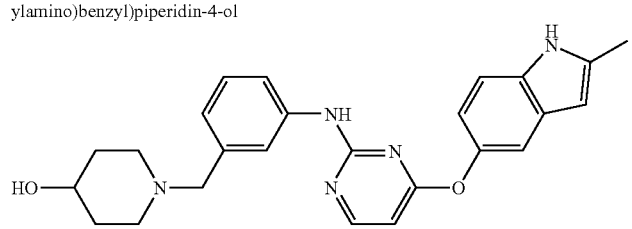 | MS (m/e): 494.5 (M + 1) |
| 143 | 1-(3-(4-(2-methyl-1H-indol-5-yloxy)pyrimidin-2-ylamino)benzyl)piperidin-4-ol<br/>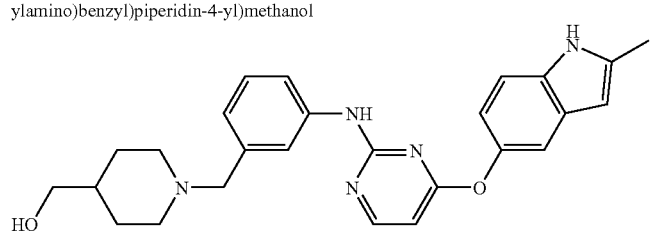 | MS (m/e): 430.4 (M + 1) |
| 144 | (1-(3-(4-(2-methyl-1H-indol-5-yloxy)pyrimidin-2-ylamino)benzyl)piperidin-4-yl)methanol<br/>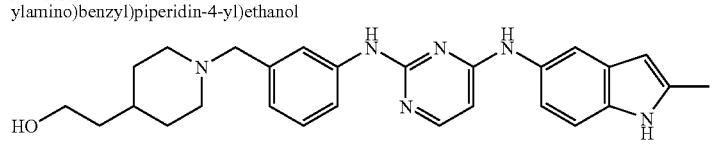 | MS (m/e): 444.4 (M + 1) |
| 145 | 2-(1-(3-(4-(2-methyl-1H-indol-5-yloxy)pylrimidin-2-ylamino)benzyl)piperidin-4-yl)ethanol | MS (m/e): 458.5 (M + 1) |

| Compound | Name/Structure | ¹H NMR (400 MHz, δ ppm)/MS |
|---|---|---|
| 146 | N-(3-(4-(2-methyl-1H-indol-5-yloxy)pyrimidin-2-ylamino)phenyl)methanesulfonamide | MS (m/e): 409.12 (M + 1) |
| 147 | (S)-4-(2-methyl-1H-indol-5-yloxy)-N-(3-(1-(methylsulfonyl)pyrrolidin-3-yloxy)phenyl)pyrimidin-2-amine | MS (m/e): 480.5 (M + 1) |
| 148 | (E)-N,N-dimethyl-3-(3-(4-(2-methyl-1H-indol-5-yloxy)pyrimidin-2-ylamino)phenyl)acrylamide | MS (m/e): 414.5 (M + 1) |
| 149 | 3-(3-(4-(2-methyl-1H-indol-5-yloxy)pyrimidin-2-ylamino) phenyl)-1-morpholinopropan-1-one | MS (m/e): 458.5 (M + 1) |
| 150 | N-(3-(2-methoxyethoxy)phenyl)-4-(2-methyl-1H-indol-5-yloxy)pyrimidin-2-amine | MS (m/e): 391.0 (M + 1) |
| 151 | 4-(2-methyl-1H-indol-5-yloxy)-N-(3-(morpholinosulfonyl)phenyl)pyrimidin-2-amine | MS (m/e): 465.1 (M + 1) |
| 152 | N-(2-(3-(4-(2-methyl-1H-indol-5-yloxy)pyrimidin-2-ylamino)phenoxy)ethyl)methanesulfonamide | MS (m/e): 454.2 (M + 1) |

| Compound | Name/Structure | $^1$H NMR (400 MHz, δ ppm)/MS |
|---|---|---|
| | 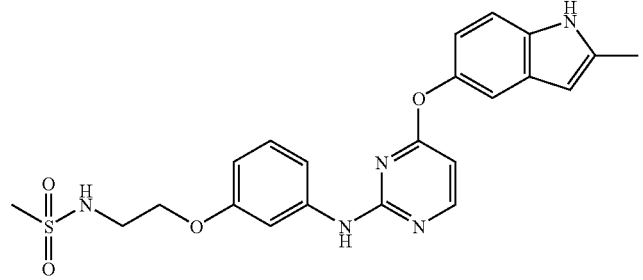 | |
| 153 | (R)-4-(2-methyl-1H-indol-5-yloxy)-N-(3-(1-(methylsulfonyl)pyrrolidin-3-yloxy)phenyl)pyrimidin-2-amine<br>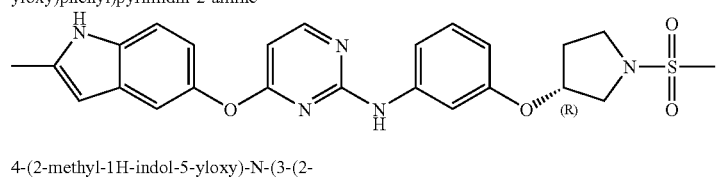 | MS (m/e): 480.5 (M + 1) |
| 154 | 4-(2-methyl-1H-indol-5-yloxy)-N-(3-(2-morpholinoethoxy)phenyl)pyrimidin-2-amine<br>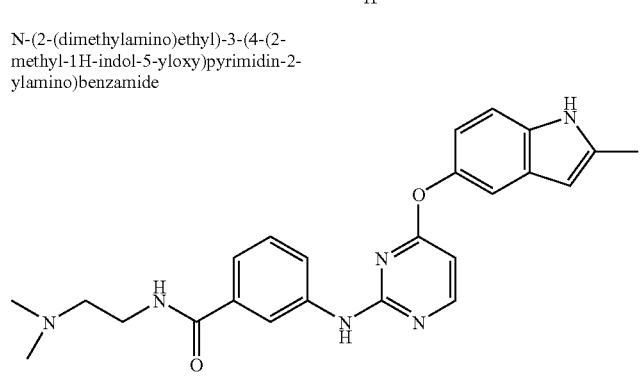 | MS (m/e): 446.4 (M + 1) |
| 155 | N-(2-(dimethylamino)ethyl)-3-(4-(2-methyl-1H-indol-5-yloxy)pyrimidin-2-ylamino)benzamide<br>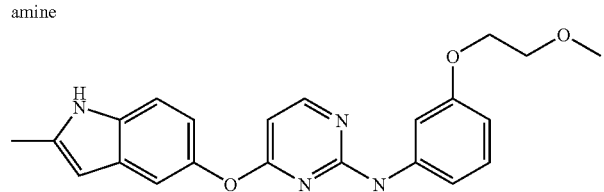 | MS (m/e): 431.4 (M + 1) |
| 156 | N-(3-(2-methoxyethoxy)phenyl)-4-(2-methyl-1H-indol-5-yloxy)pyrimidin-2-amine<br>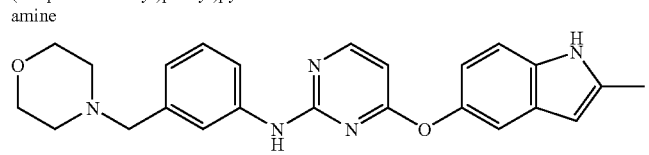 | MS (m/e): 391.3 (M + 1) |
| 157 | 4-(2-methyl-1H-indol-5-yloxy)-N-(3-(morpholinomethyl)phenyl)pyrimidin-2-amine<br>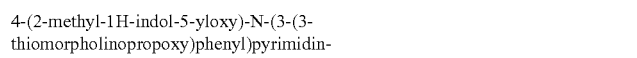 | MS (m/e): 416.4 (M + 1) |
| 158 | 4-(2-methyl-1H-indol-5-yloxy)-N-(3-(3-thiomorpholinopropoxy)phenyl)pyrimidin- | MS (m/e): 476.5 (M + 1) |

| Compound | Name/Structure | ¹H NMR (400 MHz, δ ppm)/MS |
|---|---|---|
| | 2-amine | |
| 159 | N-(3-(2-(dimethylamino)ethylsulfonyl)phenyl)-4-(2-methyl-1H-indol-5-yloxy)pyrimidin-2-amine | MS (m/e): 452.4 (M + 1) |
| 160 | 4-(2-methyl-1H-indol-5-yloxy)-N-(3-(2-morpholinoethylsulfonyl)phenyl)pyrimidin-2-amine | MS (m/e): 494.4 (M + 1) |
| 161 | 4-(2-methyl-1H-indol-5-yloxy)-N-(3-(2-(pyrrolidin-1-yl)ethylsulfonyl)phenyl)pyrimidin-2-amine | MS (m/e): 478.4 (M + 1) |
| 162 | 4-(2-methyl-1H-indol-5-yloxy)-N-(3-(2-thiomorpholinoethoxy)phenyl)pyrimidin-2-amine | MS (m/e): 462.4 (M + 1) |
| 163 | 4-(2-methyl-1H-indol-5-yloxy)-N-(3-(2-(pyrrolidin-1-yl)ethoxy)phenyl)pyrimidin-2-amine | MS (m/e): 430.3 (M + 1) |
| 164 | 4-(2-methyl-1H-indol-5-yloxy)-N-(3-((4-(methylsulfonyl)piperazin-1-yl)methyl)phenyl)pyrimidin-2-amine | MS (m/e): 493.5 (M + 1) |

| Compound | Name/Structure | ¹H NMR (400 MHz, δ ppm)/MS |
|---|---|---|
| | (structure: methanesulfonyl-piperazine-CH₂-phenyl-NH-pyrimidine-NH-2-methylindole) | |
| 165 | 2-(4-(3-(4-(2-methyl-1H-indol-5-yloxy)pyrimidin-2-ylamino)benzyl)piperazin-1-yl)ethanol | MS (m/e): 459.5 (M + 1) |
| 166 | 4-(2-methyl-1H-indol-5-yloxy)-N-(3-((tetrahydro-2H-pyran-4-yl)methoxy)phenyl)pyrimidin-2-amine | MS (m/e): 431.3 (M + 1) |
| 167 | 4-(2-methyl-1H-indol-5-yloxy)-N-(3-(methylsulfonylmethyl)phenyl)pyrimidin-2-amine | MS (m/e): 409.4 (M + 1) |
| 168 | tert-butyl 4-(2-(3-(4-(2-methyl-1H-indol-5-yloxy)pyrimidin-2-ylamino)phenoxy)ethyl)piperazine-1-carboxylate | MS (m/e): 545.4 (M + 1) |
| 169 | N,N-dimethyl-3-(3-(4-(2-methyl-1H-indol-5-yloxy)pyrimidin-2-ylamino))phenyl)propanamide | MS (m/e): 416.5 (M + 1) |
| 170 | (E)-N-methyl-3-(3-(4-(2-methyl-1H-indol-5-yloxy)pyrimidin-2-ylamino)phenyl)acrylamide | MS (m/e): 400.2 (M + 1) |
| 171 | 4-(2-methyl-1H-indol-5-yloxy)-N-(3-(tetrahydro-2H-pyran-4-yloxy)phenyl)pyrimidin-2- | MS (m/e): 416.18 (M + 1) |

| Compound | Name/Structure | $^1$H NMR (400 MHz, δ ppm)/MS |
|---|---|---|
| | amine<br>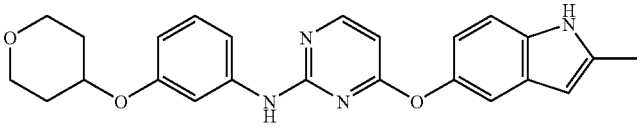 [SMILES: Cc1cc2cc(Oc3ccnc(Nc4cccc(OC5CCOCC5)c4)n3)ccc2[nH]1] | |
| 172 | N-(3-(2-aminoethoxy)phenyl)-4-(2-methyl-1H-indol-5-yloxy)pyrimidin-2-amine<br>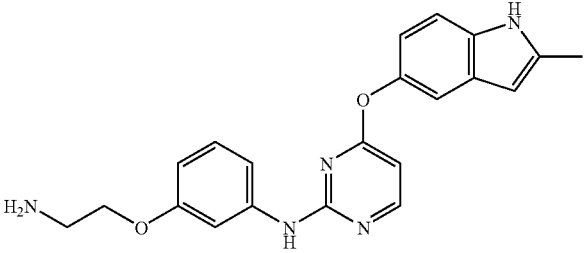 | MS (m/e): 376.3 (M + 1) |
| 173 | N-(3-(4-(2-methyl-1H-indol-5-yloxy)pyrimidin-2-ylamino)benzyl)methanesulfonamide<br>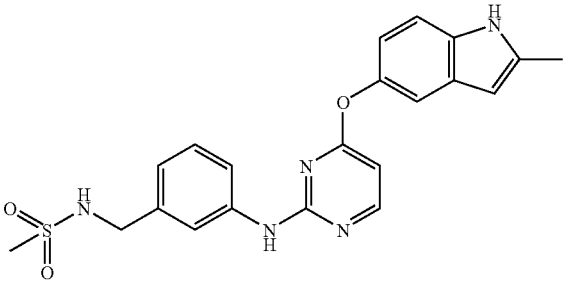 | MS (m/e): 424.4 (M + 1) |
| 174 | N-(2-hydroxyethyl)-3-(4-(2-methyl-1H-indol-5-yloxy)pyrimidin-2-ylamino)benzamide<br>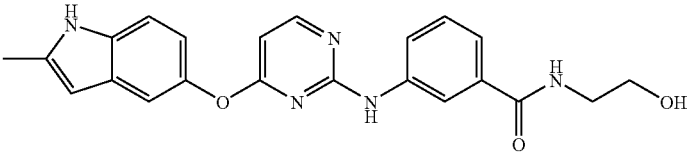 [SMILES: Cc1cc2cc(Oc3ccnc(Nc4cccc(C(=O)NCCO)c4)n3)ccc2[nH]1] | MS (m/e): 404.1 (M + 1) |
| 175 | 4-(2-methyl-1H-indol-5-yloxy)-N-(3-(2-(piperazin-1-yl)ethoxy)phenyl)pyrimidin-2-amine<br>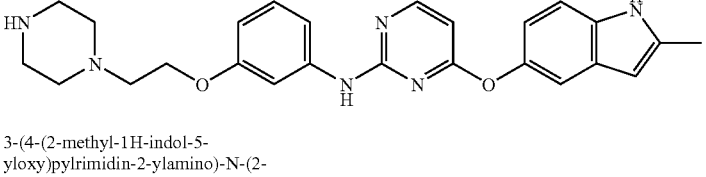 | MS (m/e): 444.5 (M) |
| 176 | 3-(4-(2-methyl-1H-indol-5-yloxy)pyrimidin-2-ylamino)-N-(2-(methylamino)-2-oxoethyl)benzamide<br>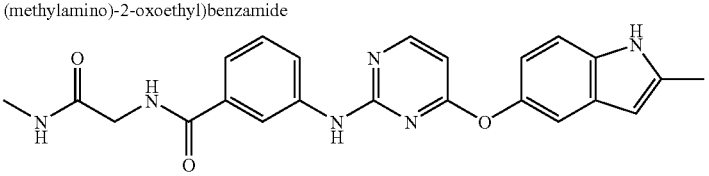 | MS (m/e): 431.2 (M + 1) |
| 177 | 3-(4-(2-methyl-1H-indol-5-yloxy)pyrimidin-2-ylamino)-N-(2-morpholinoethyl)benzamide | MS (m/e): 473.0 (M + 1) |

| Compound | Name/Structure | ¹H NMR (400 MHz, δ ppm)/MS |
|---|---|---|
| 178 | 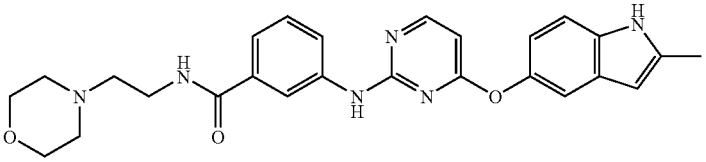 [SMILES: Cc1cc2cc(Oc3ccnc(Nc4cccc(C(=O)NCCN5CCOCC5)c4)n3)ccc2[nH]1]<br>3-(4-(2-methyl-1H-indol-5-yloxy)pyrimidin-2-ylamino)-N-(2-(piperidin-1-yl)ethyl)benzamide | MS (m/e): 471.4 (M + 1) |
| 179 | 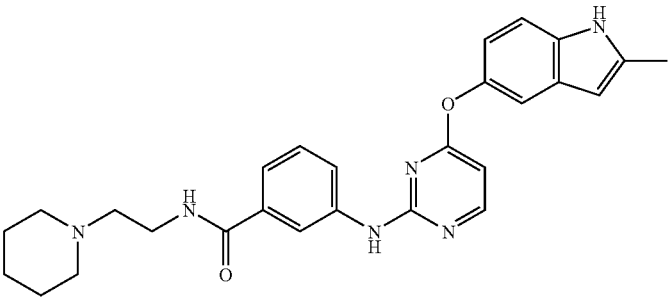<br>N-methyl-3-(3-(4-(2-methyl-1H-indol-5-yloxy)pyrimidin-2-ylamino))phenyl)propanamide | MS (m/e): 402.2 (M + 1) |
| 180 | 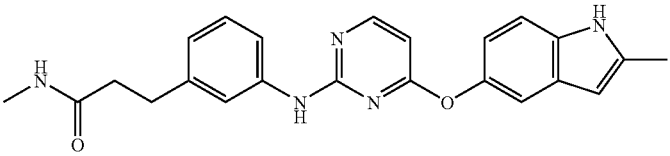<br>N-(2-methoxyethyl)-3-(4-(2-methyl-1H-indol-5-yloxy)pyrimidin-2-ylamino)benzamide | MS (m/e): 418.1 (M + 1) |
| 181 | 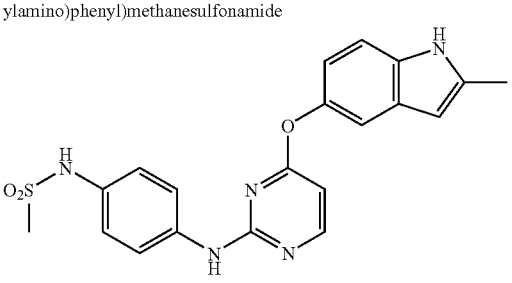<br>N-(4-(4-(2-methyl-1H-indol-5-yloxy)pyrimidin-2-ylamino)phenyl)methanesulfonamide | MS (m/e): 410.2 (M + 1) |
| 182 | <br>2-(3-(4-(2-methyl-1H-indol-5-yloxy)pyrimidin-2-ylamino)phenyl)-N-(2-morpholinoethyl)acetamide | MS (m/e): 487.1 (M + 1) |

| Compound | Name/Structure | $^1$H NMR (400 MHz, δ ppm)/MS |
|---|---|---|
| | 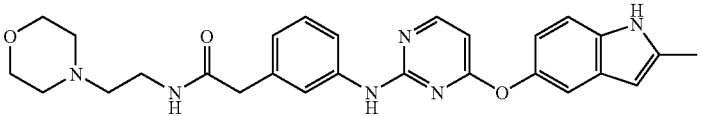 [SMILES: Cc1cc2cc(Oc3ccnc(Nc4cccc(CC(=O)NCCN5CCOCC5)c4)n3)ccc2[nH]1] | |
| 183 | 4-(2-methyl-1H-indol-5-yloxy)-N-(3-(2-(methylsulfonyl)ethoxy)phenyl)pyrimidin-2-amine<br />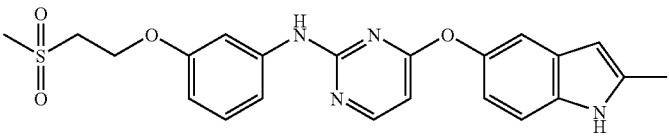 | MS (m/e): 439.2 (M + 1) |
| 184 | N-methyl(3-(4-(2-methyl-1H-indol-5-yloxy)pyrimidin-2-ylamino)phenyl)methanesulfonamide<br />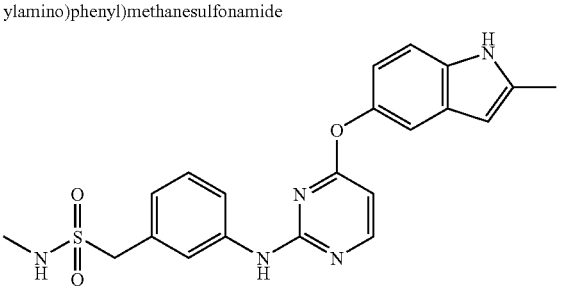 | MS (m/e): 424.4 (M + 1) |
| 185 | N-(6-methoxypyridin-3-yl)-4-(2-methyl-1H-indol-5-yloxy)pyrimidin-2-Amine<br />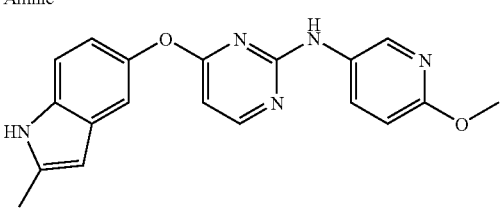 | MS (m/e): 348.2 (M + 1) |
| 186 | methyl 2-(4-(4-(4-fluoro-2-methyl-1H-indol-5-ylamino)pyrimidin-2-ylamino)phenyl)acetate<br />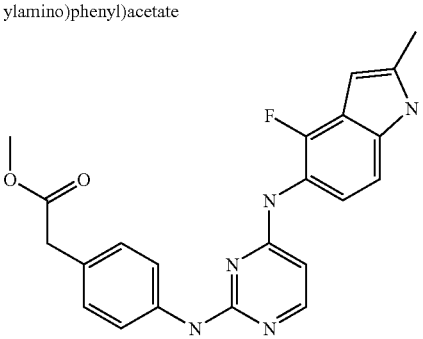 | MS (m/e): 406.2 (M + 1) |
| 187 | N4-(4-fluoro-2-methyl-1H-indol-5-yl)-N2-(2-methoxyphenyl)pyrimidine-2,4-diamine | MS (m/e): 364.2 (M + 1) |

| Compound | Name/Structure | ¹H NMR (400 MHz, δ ppm)/MS |
|---|---|---|
| | 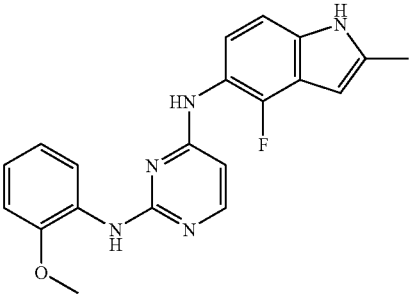 [SMILES: COc1ccccc1Nc1nccc(Nc2ccc3[nH]c(C)cc3c2F)n1] | |
| 188 | N2-(3-bromophenyl)-N4-(4-fluoro-2-methyl-1H-indol-5-yl)pyrimidine-2,4-diamine | MS (m/e): 412.3 (M + 1) |
| | 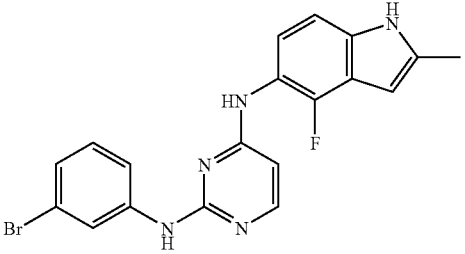 [SMILES: Cc1cc2c(F)c(Nc3ccnc(Nc4cccc(Br)c4)n3)ccc2[nH]1] | |
| 189 | N4-(4-fluoro-2-methyl-1H-indol-5-yl)-N2-(3-(methylsulfonyl)phenyl)pyrimidine-2,4-diamine | MS (m/e): 412.3 (M + 1) |
| | 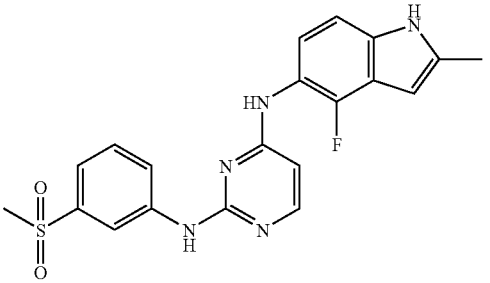 | |
| 190 | 3-(4-(4-fluoro-2-methyl-1H-indol-5-ylamino):pyrimidin-2-ylamino)benzonitrile | MS (m/e): 359.3 (M + 1) |
| | 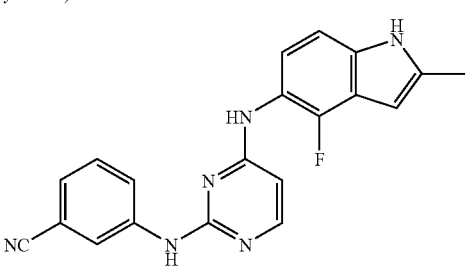 | |
| 191 | N2-(2-chloro-4-fluorophenyl)-N4-(4-fluoro-2-methyl-1H-indol-5-yl)pyrimidine-2,4-diamine | MS (m/e): 386.2 (M + 1) |

| Compound | Name/Structure | ¹H NMR (400 MHz, δ ppm)/MS |
|---|---|---|
| | 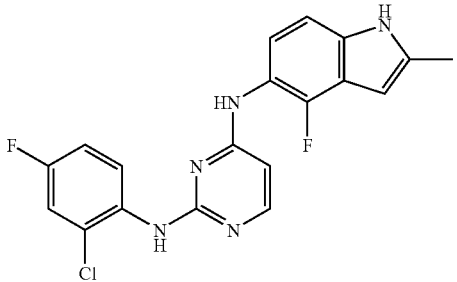 [SMILES: Cc1cc2c(F)c(Nc3ccnc(Nc4ccc(F)cc4Cl)n3)ccc2[nH]1] | |
| 192 | N-(3-(4-(4-fluoro-2-methyl-1H-indol-5-ylamino)pyrimidin-2-ylamino)phenyl)methanesulfonamide 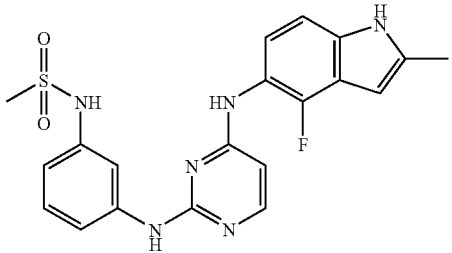 | MS (m/e): 427.3 (M + 1) |
| 193 | N2-(3,4-difluorophenyl)-N4-(4-fluoro-2-methyl-1H-indol-5-yl)pyrimidine-2,4-diamine 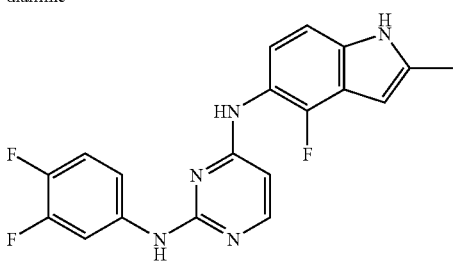 | MS (m/e): 370.2 (M + 1) |
| 194 | N4-(4-fluoro-2-methyl-1H-indol-5-yl)-N2-(3-(2-morpholinoethoxy)phenyl)pyrimidine-2,4-diamine 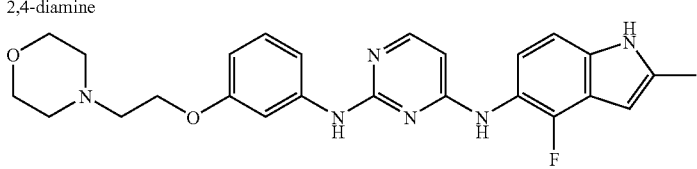 | MS (m/e): 463.4 (M + 1) |
| 195 | N4-(4-fluoro-2-methyl-1H-indol-5-yl)-N2-(3-(2-(4-(methylsulfonyl)piperazin-1-yl)ethoxy)phenyl)pyrimidine-2,4-diamine 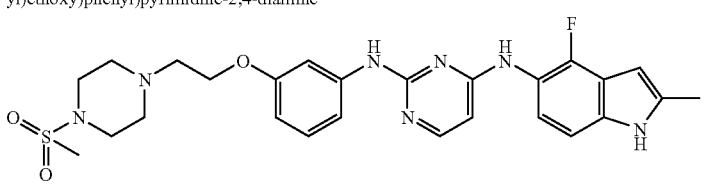 | MS (m/e): 540.3 (M + 1) |
| 196 | N4-(4-fluoro-2-methyl-1H-indol-5-yl)-N2-(2-(2-morpholinoethoxy)phenyl)pyrimidine-2,4-diamine | MS (m/e): 462.3 (M) |

-continued

| Compound | Name/Structure | $^1$H NMR (400 MHz, δ ppm)/MS |
|---|---|---|
| 197 | N2-(3-(3-(dimethylamino)propoxy)phenyl)-N4-(4-fluoro-2-methyl-1H-indol-5-yl)pyrimidine-2,4-diamine | MS (m/e): 435.4 (M + 1) |
| 198 | N-cyclopropyl-2-(3-(4-(4-fluoro-2-methyl-1H-indol-5-ylamino)pyrimidin-2-ylamino)phenyl)acetamide | MS (m/e): 431.4 (M + 1) |
| 199 | N-(2-(3-(4-(4-fluoro-2-methyl-1H-indol-5-ylamino)pyrimidin-2-yl amino)phenoxy)ethyl)methanesulfonamide | MS (m/e): 471.4 (M + 1) |
| 200 | 2-(2-(4-(4-fluoro-2-methyl-1H-indol-5-ylamino)pyrimidin-2-ylamino)phenoxy)ethanol | MS (m/e): 394.4 (M + 1) |

| Compound | Name/Structure | ¹H NMR (400 MHz, δ ppm)/MS |
|---|---|---|
| 201 | N2-(3-(2-(dimethylamino)ethoxy)phenyl)-N4-(4-fluoro-2-methyl-1H-indol-5-yl)pyrimidine-2,4-diamine | MS (m/e): 421.4 (M + 1) |
| 202 | (1-(3-(4-(4-fluoro-2-methyl-1H-indol-5-ylamino)pyrimidin-2-ylamino)benzyl)piperidin-4-yl)methanol | MS (m/e): 461.5 (M + 1) |
| 203 | 3-(4-(4-fluoro-2-methyl-1H-indol-5-ylamino)pyrimidin-2-ylamino)-N-methylbenzamide | MS (m/e): 391.3 (M + 1) |
| 204 | trifluoro-N-(3-(4-(4-fluoro-2-methyl-1H-indol-5-ylamino)pyrimidin-2-ylamino)phenyl)methanesulfonamide | MS (m/e): 481.3 (M + 1) |
| 205 | N4-(4-fluoro-2-methyl-1H-indol-5-yl)-N2-(3-(piperidin-4-ylmethoxy)phenyl)pyrimidine-2,4-diamine | MS (m/e): 446.22 (M + 1) |
| 206 | (E)-3-(3-(4-(4-fluoro-2-methyl-1H-indol-5-ylamino)pyrimidin-2-ylamino)phenyl)-1-morpholinoprop-2-en-1-one | MS (m/e): 473.5 (M + 1) |

-continued

| Compound | Name/Structure | ¹H NMR (400 MHz, δ ppm)/MS |
|---|---|---|
| | 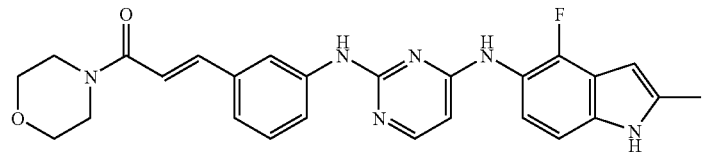 [SMILES: Cc1cc2c(F)c(Nc3ccnc(Nc4cccc(/C=C/C(=O)N5CCOCC5)c4)n3)ccc2[nH]1] | |
| 207 | trifluoro-N-(4-(4-(4-fluoro-2-methyl-1H-indol-5-ylamino)pyrimidin-2-ylamino)phenyl)methanesulfonamide | MS (m/e): 481.3 (M + 1) |
| | 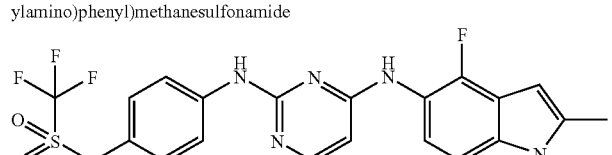 | |
| 208 | N-(5-(4-(4-fluoro-2-methyl-1H-indol-5-ylamino)pyrimidin-2-ylamino)pyridin-2-yl)acetamide | MS (m/e): 392.4 (M + 1) |
| | 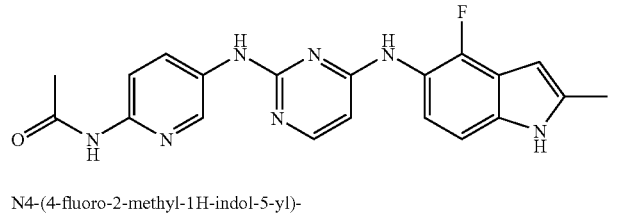 | |
| 209 | N4-(4-fluoro-2-methyl-1H-indol-5-yl)-N2-(3-(morpholinosulfonyl)phenyl)pyrimidine-2,4-Diamine | MS (m/e): 483.5 (M + 1) |
| | 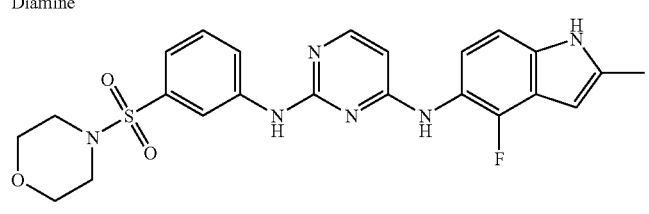 | |
| 210 | 3-(4-(4-fluoro-2-methyl-1H-indol-5-ylamino)pyrimidin-2-ylamino)-N-methylbenzenesulfonamide | MS (m/e): 427.1 (M + 1) |
| | 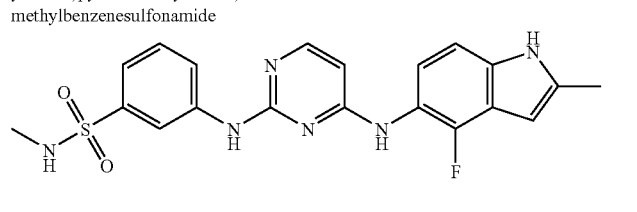 | |
| 211 | N4-(4-fluoro-2-methyl-1H-indol-5-yl)-N2-(3-(2-methoxyethoxy)phenyl)pyrimidine-2,4-diamine | MS (m/e): 408.4 (M + 1) |
| | 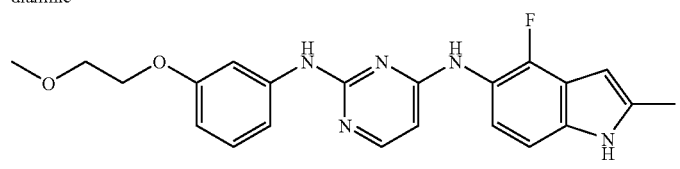 | |
| 212 | 4-(4-fluoro-2-methyl-1H-indol-5-yl)-N-(3-(3-(thiomorpholino-1',1'-dioxide)propoxy)phenyl)pyrimidin-2-amine | MS (m/e): 525.5 (M + 1) |

| Compound | Name/Structure | ¹H NMR (400 MHz, δ ppm)/MS |
|---|---|---|
| 213 | N-(2-(dimethylamino)ethyl)-3-(4-(4-fluoro-2-methyl-1H-indol-5-ylamino)pyrimidin-2-ylamino)benzamide | MS (m/e): 448.5 (M + 1) |
| 214 | N4-(4-fluoro-2-methyl-1H-indol-5-yl)-N2-(3-(2-(methylamino)ethoxy)phenyl)pyrimidine 2,4-diamine | MS (m/e): 407.5 (M + 1) |
| 215 | (E)-3-(3-(4-(4-fluoro-2-methyl-1H-indol-5-ylamino)pyrimidin-2-ylamino)phenyl)-1-morpholinoprop-2-en-1-one | MS (m/e): 473.1 (M + 1) |
| 216 | N4-(4-fluoro-2-methyl-1H-indol-5-yl)-N2-(3-(3-thiomorpholinopropoxy)phenyl)pyrimidine-2,4-diamine | MS (m/e): 493.5 (M + 1) |
| 217 | N4-(4-fluoro-2-methyl-1H-indol-5-yl)-N2-(3-(2-morpholino ethylsulfonyl)phenyl)pyrimidine-2,4-diamine | MS (m/e): 511.4 (M + 1) |

| Compound | Name/Structure | $^1$H NMR (400 MHz, δ ppm)/MS |
|---|---|---|
| | 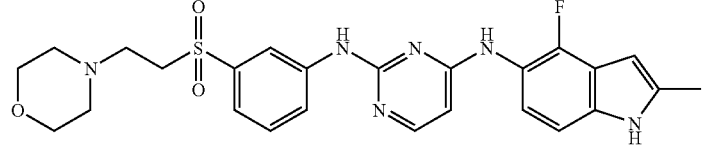 [SMILES: Cc1cc2c(F)c(Nc3ccnc(Nc4cccc(S(=O)(=O)CCN5CCOCC5)c4)n3)ccc2[nH]1] | |
| 218 | N4-(4-fluoro-2-methyl-1H-indol-5-yl)-N2-(3-(2-thiomorpholino ethoxy)phenyl)pyrimidine-2,4-diamine<br />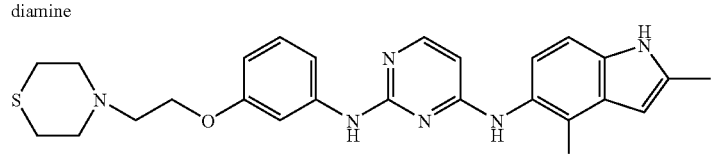 | MS (m/e): 479.4 (M + 1) |
| 219 | N4-(4-fluoro-2-methyl-1H-indol-5-yl)-N2-(3-(2-(pyrrolidin-1-yl)ethoxy)phenyl)pyrimidine-2,4-diamine<br />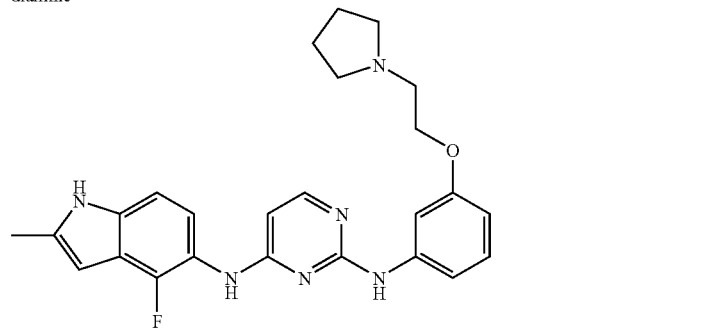 | MS (m/e): 447.4 (M + 1) |
| 220 | N4-(4-fluoro-2-methyl-1H-indol-5-yl)-N2-(3-((4-(methylsulfonyl)piperazin-1-yl)methyl)phenyl)pyrimidine-2,4-diamine<br />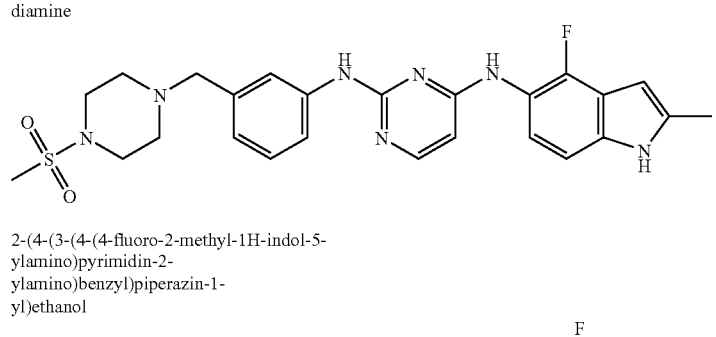 | MS (m/e): 510.4 (M + 1) |
| 221 | 2-(4-(3-(4-(4-fluoro-2-methyl-1H-indol-5-ylamino)pyrimidin-2-ylamino)benzyl)piperazin-1-yl)ethanol<br /> | MS (m/e): 474.7 (M − 1) |
| 222 | 3-(4-(4-fluoro-2-methyl-1H-indol-5-ylamino)pyrimidin-2-ylamino)phenylmethanesulfonate<br />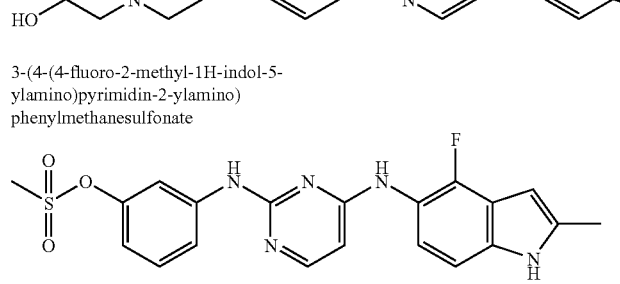 | MS (m/e): 428.4 (M + 1) |

| Compound | Name/Structure | ¹H NMR (400 MHz, δ ppm)/MS |
|---|---|---|
| 223 | N4-(4-fluoro-2-methyl-1H-indol-5-yl)-N2-(3-(methylsulfonylmethyl)phenyl)pyrimidine-2,4-diamine 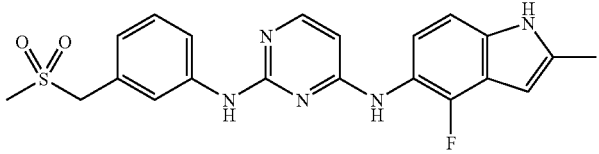 | MS (m/e): 426.4 (M + 1) |
| 224 | tert-butyl 4-(2-(3-(4-(2-methyl-1H-indol-5-ylamino)pyrimidin-2-yl amino)phenoxy)ethyl)piperazine-1-carboxylate 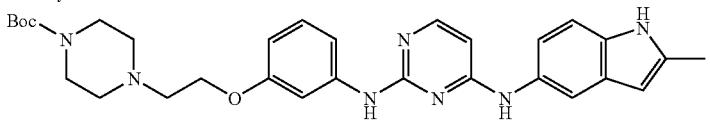 | MS (m/e): 544.4 (M + 1) |
| 225 | tert-butyl 4-(2-(3-(4-(4-fluoro-2-methyl-1H-indol-5-ylamino)pyrimidin-2-ylamino)phenoxy)ethyl)piperazine-1-carboxylate 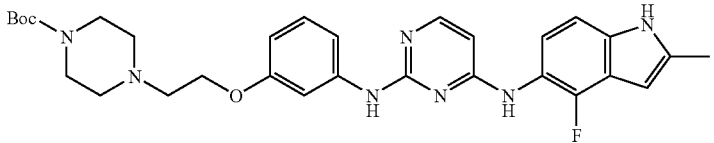 | MS (m/e): 562.3 (M + 1) |
| 226 | 3-(3-(4-(4-fluoro-2-methyl-1H-indol-5-ylamino)pyrimidin-2-ylamino))phenyl)-N,N-dimethylpropanamide 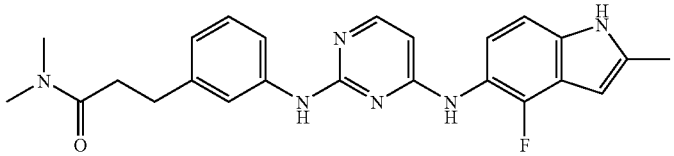 | MS (m/e): 433.4 (M + 1) |
| 227 | (E)-3-(3-(4-(4-fluoro-2-methyl-1H-indol-5-ylamino)pyrimidin-2-ylamino)phenyl)-N-methylacrylamide 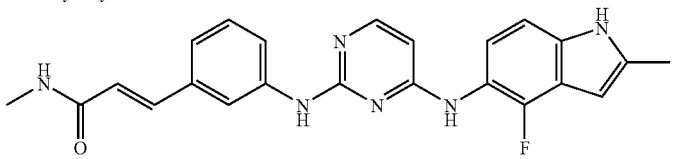 | MS (m/e): 417.2 (M + 1) |
| 228 | N4-(4-fluoro-2-methyl-1H-indol-5-yl)-N2-(3-((tetrahydro-2H-pyran-4-yl)methoxy)phenyl)pyrimidine-2,4-diamine 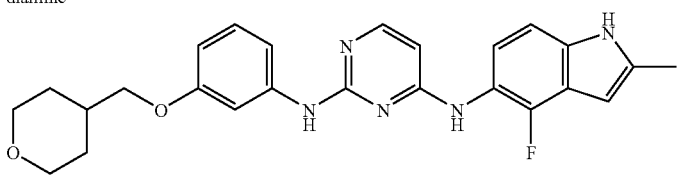 | MS (m/e): 448.4 (M + 1) |
| 229 | N2-(3-(2-aminoethoxy)phenyl)-N4-(4-fluoro-2-methyl-1H-indol-5-yl)pyrimidine-2,4-diamine | MS (m/e): 393.2 (M + 1) |

| Compound | Name/Structure | $^1$H NMR (400 MHz, δ ppm)/MS |
|---|---|---|
| 230 | 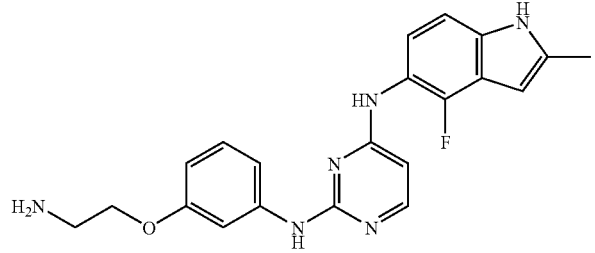<br>N-(3-(4-(4-fluoro-2-methyl-1H-indol-5-ylamino)pyrimidin-2-ylamino)benzyl)methanesulfanamide | MS (m/e): 441.4 (M + 1) |
| 231 | 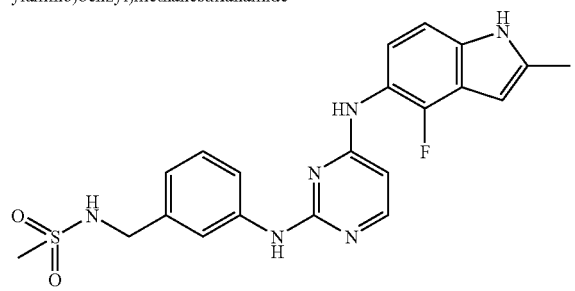<br>3-(4-(4-fluoro-2-methyl-1H-indol-5-ylamino)pyrimidin-2-ylamino)-N-(2-hydroxyethyl)benzamide | MS (m/e): 421.2 (M + 1) |
| 232 | 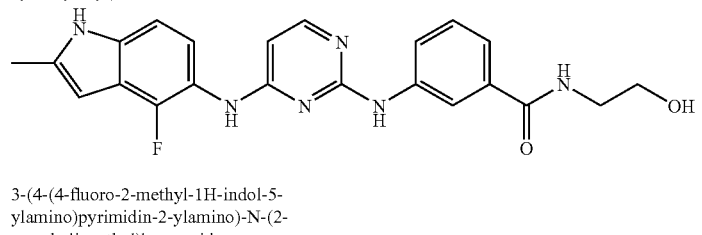<br>3-(4-(4-fluoro-2-methyl-1H-indol-5-ylamino)pyrimidin-2-ylamino)-N-(2-morpholinoethyl)benzamide | MS (m/e): 490.1 (M + 1) |
| 233 | 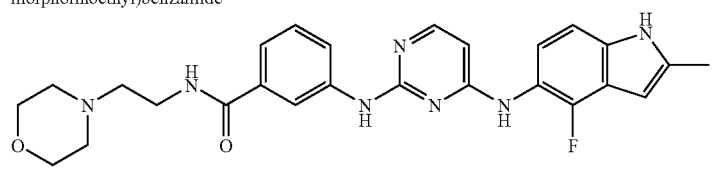<br>3-(4-(4-fluoro-2-methyl-1H-indol-5-ylamino)pyrimidin-2-ylamino)-N-(2-(piperidin-1-yl)ethyl)benzamide | MS (m/e): 488.4 (M + 1) |
| 234 | 3-(3-(4-(4-fluoro-2-methyl-1H-indol-5-ylamino)pyrimidin-2-ylamino)phenyl)-N-methylpropanamide | MS (m/e): 419.2 (M + 1) |

| Compound | Name/Structure | $^1$H NMR (400 MHz, δ ppm)/MS |
|---|---|---|
| | 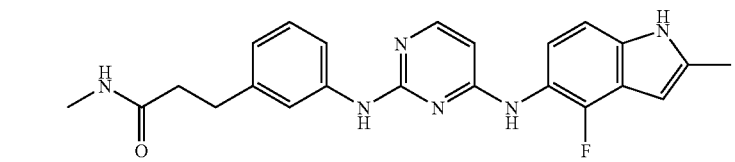 | |
| 235 | 3-(4-(4-fluoro-2-methyl-1H-indol-5-ylamino)pyrimidin-2-ylamino)-N-(2-methoxyethyl)benzamide | MS (m/e): 435.2 (M + 1) |
| | 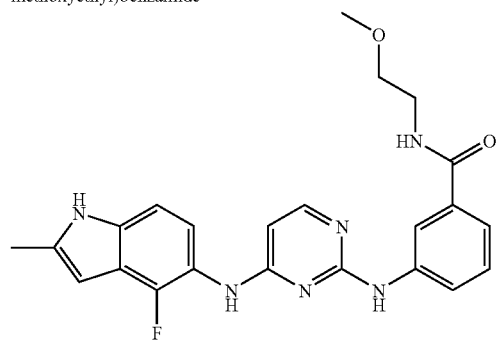 | |
| 236 | N-(4-(4-(4-fluoro-2-methyl-1H-indol-5-ylamino)pyrimidin-2-yl amino)phenyl)methanesulfonamide | MS (m/e): 427.2 (M + 1) |
| | 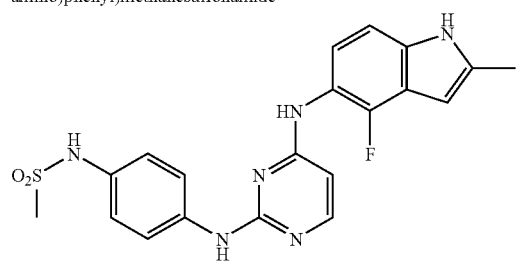 | |
| 237 | 2-(3-(4-(4-fluoro-2-methyl-1H-indol-5-ylamino)pyrimidin-2-ylamino)phenyl)-N-(2-morpholinoethyl)acetamide | MS (m/e): 504.1 (M + 1) |
| | 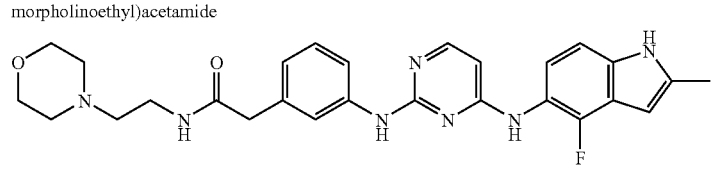 | |
| 238 | 3-(4-(4-fluoro-2-methyl-1H-indol-5-ylamino)pyrimidin-2-ylamino)-N-(2-(methylamino)-2-oxoethyl)benzamide | MS (m/e): 448.2 (M + 1) |
| | 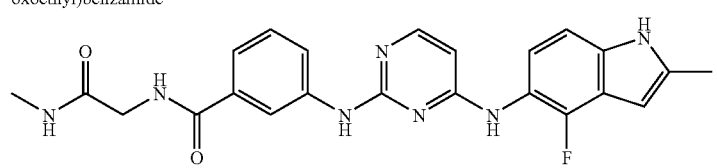 | |
| 239 | N4-(4-fluoro-2-methyl-1H-indol-5-yl)-N2-(3-(tetrahydro-2H-pyran-4-yloxy)phenyl)pyrimidine-2,4-diamine | MS (m/e): 434.4 (M + 1) |

-continued

| Compound | Name/Structure | ¹H NMR (400 MHz, δ ppm)/MS |
|---|---|---|
| | 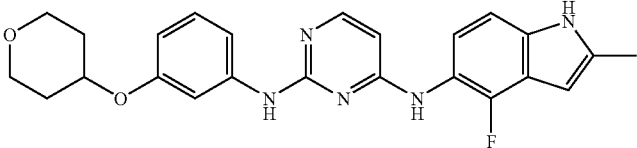 [SMILES: Cc1cc2c(F)c(Nc3ccnc(Nc4cccc(OC5CCOCC5)c4)n3)ccc2[nH]1] | |
| 240 | 1-(3-(4-(4-fluoro-2-methyl-1H-indol-ylamino)pyrimidin-2-ylamino)benzyl)sulphonyl-methylamine 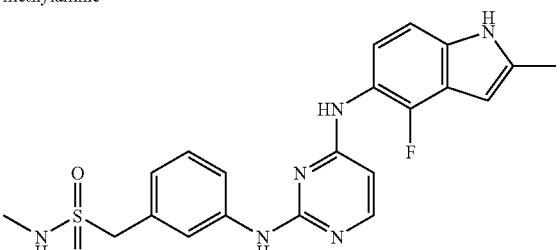 | MS (m/e): 441.4 (M + 1) |
| 241 | N4-(4-fluoro-2-methyl-1H-indol-5-yl)-N2-(6-methoxypyridin-3-yl)pyrimidine-2,4-diamine 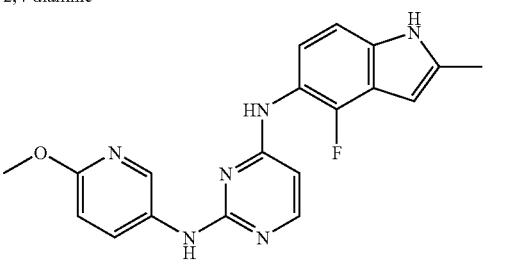 | MS (m/e): 365.4 (M + 1) |
| 242 | 4-(4-fluoro-2-methyl-1H-indol-5-yloxy)-N-(3-(2-morpholinoethoxy)phenyl)pyrimidin-2-amine 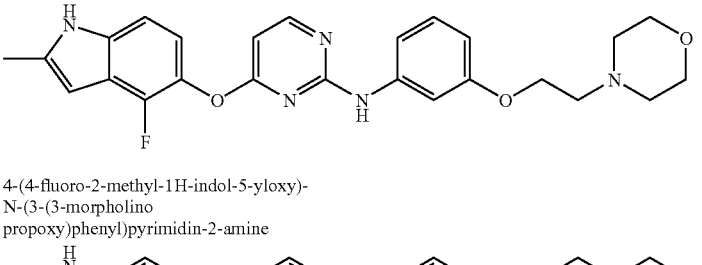 | MS (m/e): 464.4 (M + 1) |
| 243 | 4-(4-fluoro-2-methyl-1H-indol-5-yloxy)-N-(3-(3-morpholino propoxy)phenyl)pyrimidin-2-amine 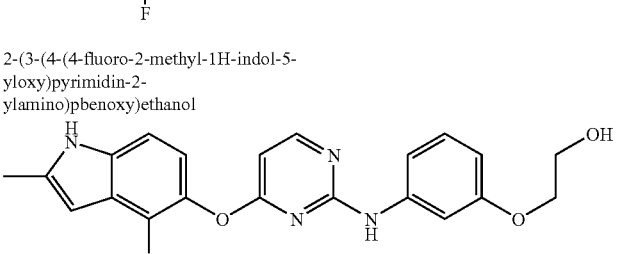 | MS (m/e): 478.4 (M + 1) |
| 244 | 2-(3-(4-(4-fluoro-2-methyl-1H-indol-5-yloxy)pyrimidin-2-ylamino)phenoxy)ethanol 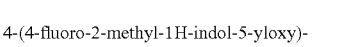 | MS (m/e): 395.4 (M + 1) |
| 245 | 4-(4-fluoro-2-methyl-1H-indol-5-yloxy)- | MS (m/e): 526.7 (M + 1) |

| Compound | Name/Structure | ¹H NMR (400 MHz, δ ppm)/MS |
|---|---|---|
| | N-(3-(3-(thiomorpholino-1',1'-dioxide)propoxy)phenyl)pyrimidin-2-amine | |
| 246 | (R)-4-(4-fluoro-2-methyl-1H-indol-5-yloxy)-N-(3-(pyrrolidin-3-yloxy)phenyl)pyrimidin-2-amine | MS (m/e): 420.5 (M + 1) |
| 247 | (S)-4-(4-fluoro-2-methyl-1H-indol-5-yloxy)-N-(3-(pyrrolidin-3-yloxy)phenyl)pyrimidin-2-amine | MS (m/e): 420.5 (M + 1) |
| 248 | 4-(4-fluoro-2-methyl-1H-indol-5-yloxy)-N-(3-(1-(methylsulfonyl)piperidin-4-yloxy)phenyl)pyrimidin-2-amine | MS (m/e): 512.4 (M + 1) |
| 249 | (R)-4-(4-fluoro-2-methyl-1H-indol-5-yloxy)-N-(3-(1-(methylsulfonyl)pyrrolidin-3-yloxy)phenyl)pyrimidin-2-amine | MS (m/e): 498.4 (M + 1) |
| 250 | N-(2-(dimethylamino)ethyl)-3-(4-(4-fluoro-2-methyl-1H-indol-5-yloxy)pyrimidin-2-ylamino)benzamide | MS (m/e): 448.5 (M + 1) |

| Compound | Name/Structure | $^1$H NMR (400 MHz, δ ppm)/MS |
|---|---|---|
| 251 | (1-(3-(4-(4-fluoro-2-methyl-1H-indol-5-yloxy)pyrimidin-2-ylamino)benzyl)piperidin-4-yl)methanol | MS (m/e): 462.4 (M + 1) |
| 252 | 2-(1-(3-(4-(4-fluoro-2-methyl-1H-indol-5-yloxy)pyrimidin-2-ylamino)benzyl)piperidin-4-yl)ethanol | MS (m/e): 476.5 (M + 1) |
| 253 | 4-(4-fluoro-2-methyl-1H-indol-5-yloxy)-N-(3-(2-(methylamino)ethoxy)phenyl)pyrimidin-2-amine | MS (m/e): 408.4 (M + 1) |
| 254 | (E)-3-(3-(4-(4-fluoro-2-methyl-1H-indol-5-yloxy)pyrimidin-2-ylamino)phenyl)-1-morpholinoprop-2-en-1-one | MS (m/e): 474.5 (M + 1) |
| 255 | 4-(4-fluoro-2-methyl-1H-indol-5-yloxy)-N-(3-(morpholinomethyl)phenyl)pyrimidin-2-amine | MS (m/e): 434.5 (M + 1) |
| 256 | (S)-4-(4-fluoro-2-methyl-1H-indol-5-yloxy)-N-(3-(1- | MS (m/e): 498.4 (M + 1) |

| Compound | Name/Structure | ¹H NMR (400 MHz, δ ppm)/MS |
|---|---|---|
| | (methylsulfonyl)pyrrolidin-3-yloxy)phenyl)pyrimidin-2-amine | |
| 257 | 3-(4-(4-fluoro-2-methyl-1H-indol-5-yloxy)pyrimidin-2-ylamino)-N-methylbenzamide | MS (m/e): 392.4 (M + 1) |
| 258 | N-(2-(3-(4-(4-fluoro-2-methyl-1H-indol-5-yloxy)pyrimidin-2-ylamino)phenoxy)ethyl)methanesulfonamide | MS (m/e): 472.4 (M +0 1) |
| 259 | trifluoro-N-(3-(4-(4-fluoro-2-methyl-1H-indol-5-yloxy)pyrimidin-2-yl amino)phenyl)methanesulfonamide | MS (m/e): 482.3 (M + 1) |
| 260 | 4-(4-fluoro-2-methyl-1H-indol-5-yloxy)-N-(3-(3-thiomorpholinopropoxy)phenyl)pyrimidin-2-amine | MS (m/e): 494.5 (M + 1) |
| 261 | 4-(4-fluoro-2-methyl-1H-indol-5-yloxy)-N-(3-(2-(pyrrolidin-1-yl)ethylsulfonyl)phenyl)pyrimidin-2-amine | MS (m/e): 496.4 (M + 1) |

-continued

| Compound | Name/Structure | ¹H NMR (400 MHz, δ ppm)/MS |
|---|---|---|
| 262 | 4-(4-fluoro-2-methyl-1H-indol-5-yloxy)-N-(3-(2-morpholinoethylsulfonyl)phenyl)pyrimidin-2-amine 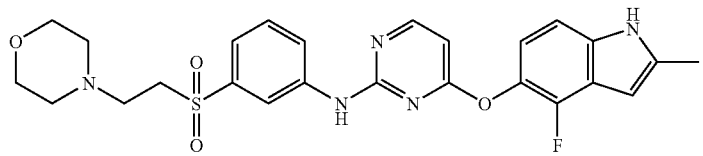 [SMILES: Cc1cc2c(F)c(Oc3ccnc(Nc4cccc(S(=O)(=O)CCN5CCOCC5)c4)n3)ccc2[nH]1] | MS (m/e): 512.4 (M + 1) |
| 263 | 4-(4-fluoro-2-methyl-1H-indol-5-yloxy)-N-(3-(2-thiomorpholinoethoxy)phenyl)pyrimidin-2-amine 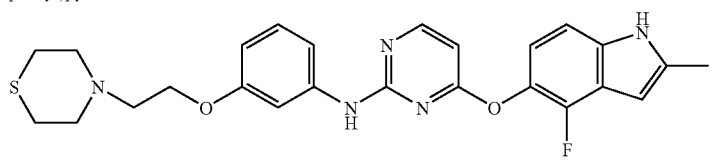 | MS (m/e): 480.4 (M + 1) |
| 264 | 4-(4-fluoro-2-methyl-1H-indol-5-yloxy)-N-(3-(2-(pyrrolidin-1-yl)ethoxy)phenyl)pyrimidin-2-amine 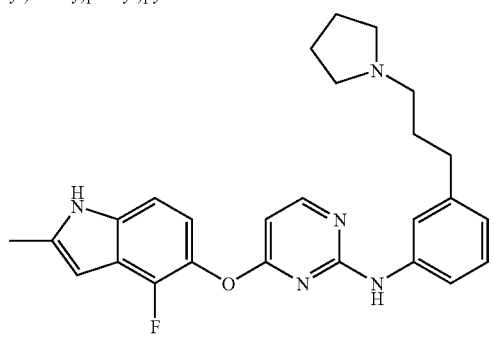 | MS (m/e): 448.4 (M + 1) |
| 265 | 4-(4-fluoro-2-methyl-1H-indol-5-yloxy)-N-(3-((4-(methylsulfonyl)piperazin-1-yl)methyl)phenyl)pyrimidin-2-amine 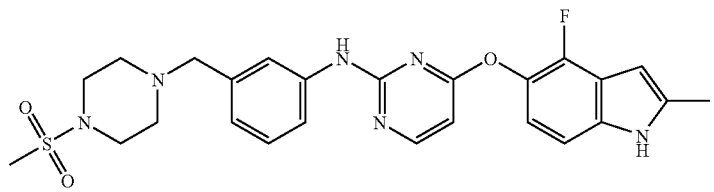 | MS (m/e): 511.4 (M + 1) |
| 266 | 2-(4-(3-(4-(4-fluoro-2-methyl-1H-indol-5-yloxy)pyrimidin-2-ylamino)benzyl)piperazin-1-yl)ethanol 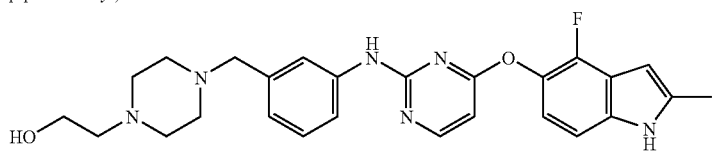 | MS (m/e): 477.5 (M + 1) |
| 267 | 4-(4-fluoro-2-methyl-1H-indol-5-yloxy)-N-(3-((tetrahydro-2H-pyran-4-yl)methoxy)phenyl) pyrimidin-2-amine | MS (m/e): 449.4 (M + 1) |

| Compound | Name/Structure | $^1$H NMR (400 MHz, δ ppm)/MS |
|---|---|---|
| 268 | trifluoro-N-(4-(4-(4-fluoro-2-methyl-1H-indol-5-yloxy)pyrimidin-2-ylamino)phenyl)methanesulfonamide 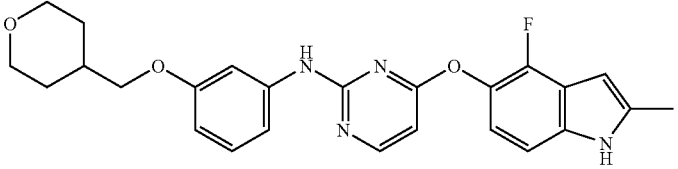 | MS (m/e): 482.3 (M + 1) |
| 269 | tert-butyl 4-(2-(3-(4-(4-fluoro-2-methyl-1H-indol-5-yloxy)pyrimidin-2-ylamino)phenoxy)ethyl)piperazine-1-carboxylate 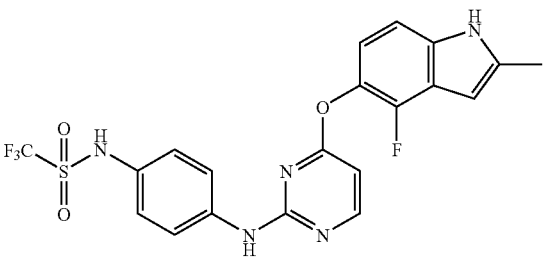 | MS (m/e): 563.4 (M + 1) |
| 270 | 4-(4-fluoro-2-methyl-1H-indol-5-yloxy)-N-(3-(tetrahydro-2H-pyran-4-yloxy)phenyl)pyrimidin-2-amine 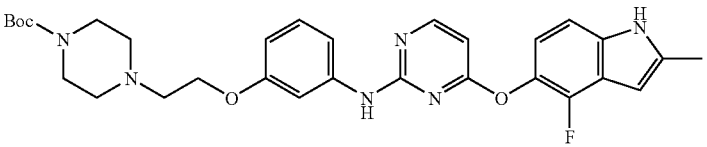 | MS (m/e): 435.4 (M + 1) |
| 271 | N-(3-(2-aminoethoxy)phenyl)-4-(4-fluoro-2-methyl-1H-indol-5-yloxy)pyrimidin-2-amine 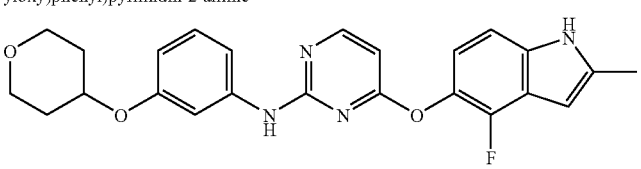 | MS (m/e): 394.4 (M + 1) |
| 272 | N-(3-(4-(4-fluoro-2-methyl-1H-indol-5-yloxy)pyrimidin-2-ylamino)benzyl)methanesulfonamide | MS (m/e): 442.4 (M + 1) |

| Compound | Name/Structure | ¹H NMR (400 MHz, δ ppm)/MS |
|---|---|---|
| | 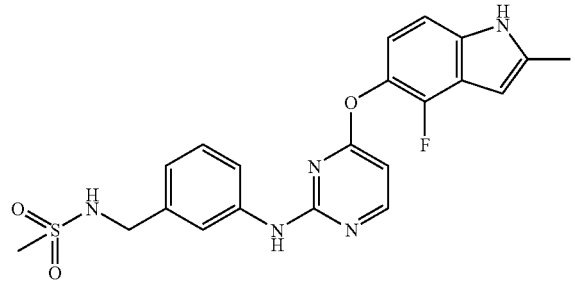 [SMILES: Cc1cc2c(F)c(Oc3ccnc(Nc4cccc(CNS(C)(=O)=O)c4)n3)ccc2[nH]1] | |
| 273 | 3-(4-(4-fluoro-2-methyl-1H-indol-5-yloxy)pyrimidin-2-ylamino)-N-(2 hydroxyethyl)benzamide<br>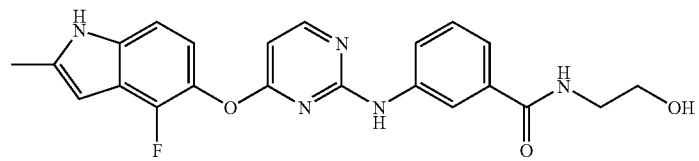 [SMILES: Cc1cc2c(F)c(Oc3ccnc(Nc4cccc(C(=O)NCCO)c4)n3)ccc2[nH]1] | MS (m/e): 422.1 (M + 1) |
| 274 | 3-(4-(4-fluoro-2-methyl-1H-indol-5-yloxy)pyrimidin-2-ylamino)-N-(2-(methylamino)-2-oxoethyl)benzamide<br>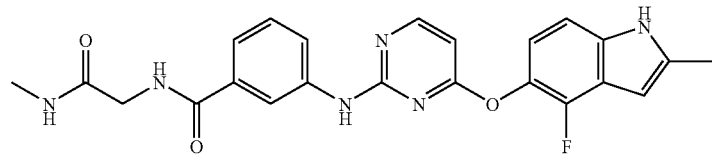 | MS (m/e): 449.5 (M + 1) |
| 275 | 3-(4-(4-fluoro-2-methyl-1H-indol-5-yloxy)pyrimidin-2-ylamino)-N-(2-morpholinoethyl)benzamide<br>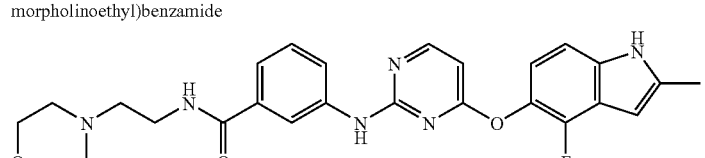 | MS (m/e): 491.1 (M + 1) |
| 276 | N-(3-(4-(4-fluoro-2-methyl-1H-indol-5-yloxy)pyrimidin-2-yl amino)phenyl)methanesulfonamide<br>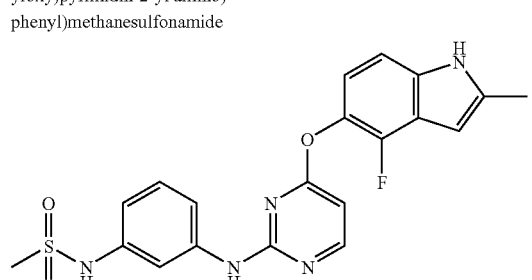 | MS (m/e): 428.1 (M + 1) |
| 277 | 3-(4-(4-fluoro-2-methyt-1H-indol-5-yloxy)pylrimidin-2-ylamino)-N-(2-(piperidin-1-yl)ethyl)benzamide | MS (m/e): 489.1 (M + 1) |

| Compound | Name/Structure | $^1$H NMR (400 MHz, δ ppm)/MS |
|---|---|---|
| 278 | 3-(3-(4-(4-fluoro-2-methyl-1H-indol-5-yloxy)pyrimidin-2-ylamino)phenyl)-N-methylpropanamide 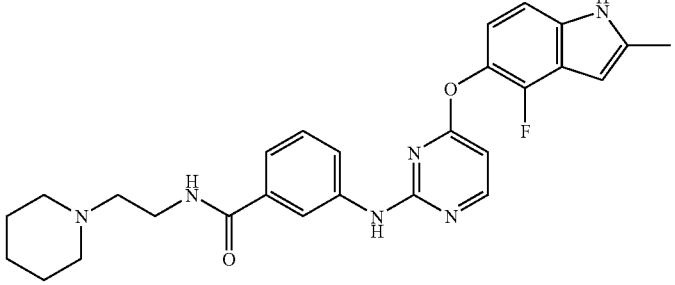 | MS (m/e): 420.2 (M + 1) |
| 279 | 3-(4-(4-fluoro-2-methyl-1H-indol-5-yloxy)pyrimidin-2-ylamino)-N-(2-methoxyethyl)benzamide 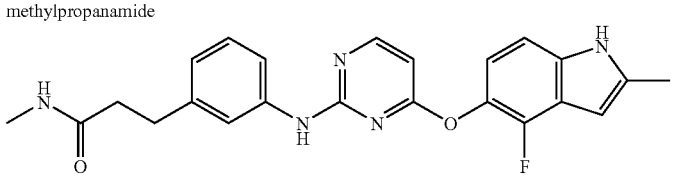 | MS (m/e): 436.1 (M + 1) |
| 280 | N-(4-(4-(4-fluoro-2-methyl-1H-indol-5-yloxy)pyrimidin-2-yl amino)phenyl)methanesulfonamide 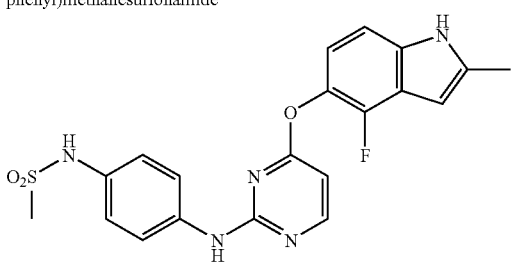 | MS (m/e): 428.1 (M + 1) |
| 281 | 2-(3-(4-(4-fluoro-2-methyl-1H-indol-5-yloxy)pyrimidin-2-ylamino)phenyl)-N-(2-morpholinoethyl)acetamide 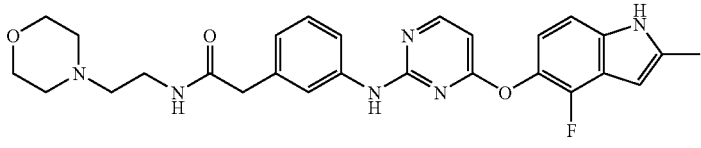 [SMILES: Cc1cc2c(F)c(Oc3ccnc(Nc4cccc(CC(=O)NCCN5CCOCC5)c4)n3)ccc2[nH]1] | MS (m/e): 505.1 (M + 1) |
| 282 | 4-(4-fluoro-2-methyl-1H-indol-5-yloxy)-N-(3-(2-(methylsulfonyl)ethoxy)phenyl)pyrimidin-2-amine | MS (m/e): 457.2 (M + 1) |

| Compound | Name/Structure | $^1$H NMR (400 MHz, δ ppm)/MS |
|---|---|---|
| 283 | 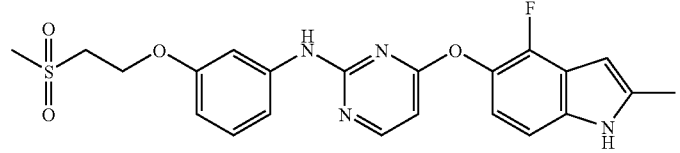<br>4-(4-fluoro-2-methyl-1H-indol-5-yloxy)<br>N-(6-methoxypyridin-3-yl)pyrimidin-2-amine | MS (m/e): 366.4 (M + 1) |
| | 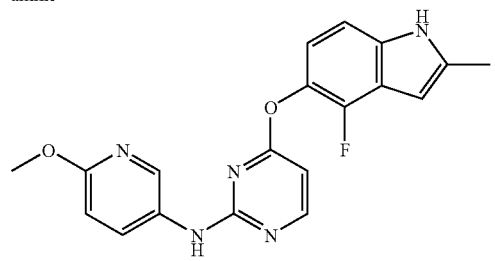 | |

Example 284

Synthesis of 3-(4-(2-methyl-1H-indol-5-ylamino)pyrimidin-2-yl amino)phenol (Compound 284)

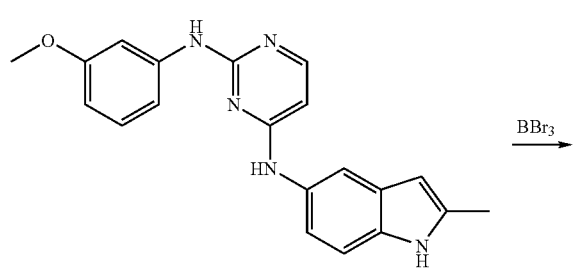

A solution of N2-(3-methoxylphenyl)-N4-(2-methyl-1H-indol-5-yl)pyrimidine-2,4-diamine (0.1 mmol) in 5 ml CH$_2$Cl$_2$ was placed in an ice bath. To this was added BBr$_3$ (0.5 mmol). The reaction mixture was stirred overnight at room temperature, then poured into ice water, and extracted with ethyl acetate. The organic layer was washed sequentially with water and brine, dried over anhydrous Na$_2$SO$_4$, and concentrated. The residue was purified by column chromatography to provide the desired product in a yield of 83%.

$^1$H NMR (DMSO-d$_6$, 400 MHz): δ 10.501 (s, 1H), 9.115 (s, 1H), 8.956 (s, 1H), 8.868 (s, 1H), 7.908 (d, J=6 Hz, 1H), 7.716 (s, 1H), 7.271 (d, J=8 Hz, 1H), 7.210 (d, J=8.4 Hz, 1H), 7.114 (d, J=8 Hz, 1H), 6.968 (t, J=8 Hz, 1H), 6.322 (dd, J=8, 1.6 Hz, 1H), 6.097 (m, 2H), 2.377 (s, 3H); MS (m/e): 331.4 (M+1).

Examples 285-295

Syntheses of Compounds 285-295

Compounds, 285-295 were each synthesized in a manner similar to that described Example 284.

| compound | Name | $^1$NMR (CD$_3$OD, 400 MHz)/MS |
|---|---|---|
| 285 | 4-(5-(4-(2-methyl-1H-indol-5-ylamino)pyrimidin-2-ylamino)-1H-pyrazol-3-yl)phenol | 7.863 (d, J = 6.0 Hz, 1H), 7.286 (d, J = 8.8 Hz, 1H), 6.830 (br, 2H), 6.125-6.080 (m, 4H), 5.558-5.527 (m, 2H), 2.415 (s, 3H); MS (m/e): 411.8 (M + 1). |

| compound | Name | $^1$NMR (CD$_3$OD, 400 MHz)/MS |
|---|---|---|
| | 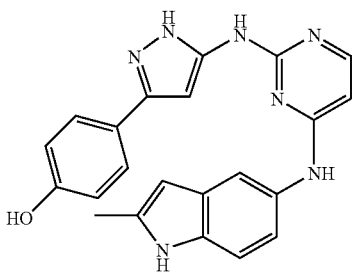 [SMILES: Cc1cc2cc(Nc3ccnc(Nc4cc(-c5ccc(O)cc5)n[nH]4)n3)ccc2[nH]1] | |
| 286 | 2-(4-(2-methyl-1H-indol-5-ylamino)pyrimidin-2-ylamino)phenol 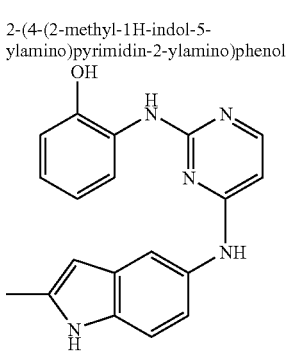 | 7.791 (d, J = 6.0 Hz, 2H), 7.584 (s, 1H), 7.047 (d, J = 8.8 Hz, 1H), 7.063 (d, J = 7.6 Hz, 1H), 6.974 (t, J = 7.6 Hz, 1H), 6.882 (d, J = 8.0 Hz, 1H), 6.794 (t, J = 8.0 Hz, 1H), 6.164 (d, J = 6.0 Hz, 1H), 6.124 (s, 1H), 2.027 (s, 3H); MS (m/e): 332.2 (M + 1). |
| 287 | 4-(4-(2-methyl-1H-indol-5-ylamino)pyrimidin-2-ylamino)phenol 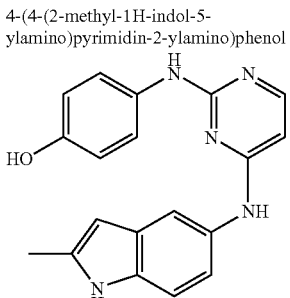 | 10.573 (s, 1H), 9.162 (s, 1H), 9.007 (s, 1H), 8.985 (s, 1H), 7.952 (d, J = 5.6 Hz, 1H), 7.766 (s, 1H), 7.301 (d, J = 8 Hz, 1H), 7.262 (d, J = 8 Hz, 1H), 7.123 (d, J = 8 Hz, 1H), 7.011 (m, 1H), 6.332 (dd, J = 8, 1.6 Hz, 1H), 6.103 (m, 2H), 2.391 (s, 3H); MS (m/e): 331.4 (M + 1) |
| 289 | 4-(4-(2-methyl-1H-indol-5-yloxy)pyrimidin-2-ylamino)phenol 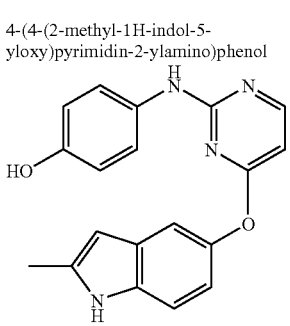 | 8.133 (d, J = 6.0 Hz, 1H), 7.324 (d, J = 8.4 Hz, 1H), 7.225-7.183 (m, 3H), 6.819 (dd, J= 8.8 Hz, J= 2.4 Hz, 1H), 6.533 (s, 1H), 6.530 (s, 1H), 6.213 (d, J = 5.6 Hz, 1H), 6.172 (s, 1H), 2.428 (s, 3H); MS (m/e): 374.3 (M + 1). |
| 290 | 3-(4-(2-methyl-1H-indol-5-yloxy)pyrimidin-2-ylamino)phenol 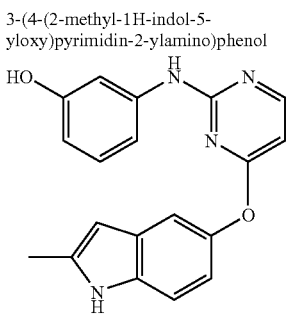 | 8.179 (d, J = 6.0 Hz, 1H), 7.333 (d, J = 8.8 Hz, 1H), 7.193 (s, 1H), 7.095 (s, 1H), 6.953 (d, J = 7.2 Hz, 1H), 6902 (t, J=8.0 Hz, 1H), 6.831 (d, J = 8.8 Hz, 1H), 6.387 (d, J = 7.6 Hz, 1H), 6.244 (d, J = 6.0 Hz, 1H), 6.171 (s, 1H), 3.332 (s, 3H), 2.454 (s, 3H); MS (m/e): 333.2 (M + 1). |
| 291 | 2-(4-(4-fluioro-2-methyl-1H-indol-5-ylamino)pyrimidin-2-ylamino)phenol OH | 11.249 (s, 1H), 8.943 (d, J = 4.8 Hz, 1H), 7.920 (d, J = 5.6 Hz, 1H), 7.867 (m, J = 6.4 Hz, 2H), 7.128 (d, J = 8.0 Hz, 1H), 7.078 (t, J = 8.4-6.8 Hz, 1H), 6.797 (s, |

Example 296

Synthesis of N-(2-methoxypyrimidin-4-yl)-N-(2-methyl-1H-indol-5-yl)pyrimidine-2,4-diamine (Compound 296)

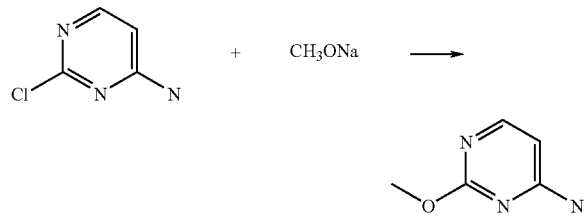

The solution of 2-chloropyrimidin-4-amine (1 mmol) and sodium methoxide (1.5 mmol) in 10 ml methanol was refluxed for 2 h, after removing of solvent, the residue was dissolved in CH$_2$Cl$_2$ and washed with water, dried over anhydrous NaSO4, concentrated in vacuo to give 2-methoxypyrimidin-4-amine.

-continued

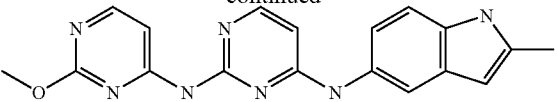

compound 296

To a solution of 2-methoxypyrimidin-4-amine (0.1 mmol) and N-(2-chloropyrimidin-4-yl)-2-methyl-1H-indol-5-amine (0.1 mmol) in 3 ml dioxide, CsCO$_3$ (0.2 mmol), Pd(OAc)$_2$(10 mmol %) and Xantphos (10 mmol %) were added. The mixture was stirred under microwave irradiation at 200° C. for 40 mins. After cooling the solution was filtered and the filtrate was concentrated in vacuo, the residue was purified by column chromatography(C-18) to give N-(2-methoxypyrimidin-4-yl)-N-(2-methyl-1H-indol-5-yl)pyrimidine-2,4-diamine (yield 48%).

$^1$H NMR (DMSO-d6, 400 MHz): 10.839 (s, 1H), 9.718 (s, 1H), 9.281 (s, 1H), 8.162 (d, J=6.0 Hz, 1H), 8.032 (m, 2H), 7.693 (s, 1H), 7.251 (d, J=8.8 Hz, 1H), 7.099 (d, J=7.2 Hz, 1H), 6.300 (d, J=6.0 Hz, 1H), 6.107 (s, 1H), 3.863 (s, 3H), 2.383 (s, 3H); MS (m/e): 348.2 (M+1)

Examples 297-299

Syntheses of Compounds 297-299

Compounds 297-299 were each synthesized in a manner similar to that described in Example 296.

| compound | Name | $^1$H NMR (DMSO-d$_6$, 400 MHz)/MS |
|---|---|---|
| 297 | N-(2-methoxypyridin-4-yl)-N-(2-methyl-1H-indol-5-yl)pyrimidine-2,4-diamine | 10.837 (s, 1H), 9.421 (s, 1H), 9.144 (s, 1H), 7.978 (d, J = 6.0 Hz, 1H), 7.838 (d, J = 6.0 Hz, 1H), 7.606 (s, 1H), 7.333-7.303 (m, 2H), 7.249 (d, J = 8.4 Hz, 1H), 7.084 (d, J = 8.0 Hz, 1H), 6.205 (d, J = 5.6 Hz, 1H), 6.088 (s, 1H), 3.775 (s, 3H), 2.382 (s, 3H); MS (m/e): 347.2 (M + 1) |
| 298 | N-(2-methoxypyridin-4-yl)-N-(2-methyl-1H-indol-5-yl)pyrimidine-2,4-diamine | 11.258 (s, 1 H), 10.400 (br, 1H), 9.036 (s, 1H), 8.829 (s, 1H), 8.509 (s, 1H), 8.048 (d, J = 8.4 Hz, 1H), 7.911 (d, J = 5.6 Hz, 1H), 7.007-7.122 (m, 2H), 6.743 (dd, J = 8.4 Hz, 1.6 Hz, 1H), 6.194 (s, 1H), 6.012 (br, 1H), 3.166 (s, 3H), 2.397 (s, 3H); MS (m/e): 428.1 (M + 1) |
| 299 | N-(5-(4-(2-methyl-1H-indol-5-yloxy)pyrimidin-2-ylamino)pyridin-2-yl)methanesulfonamide | MS (m/e): 411.4 (M + 1) |

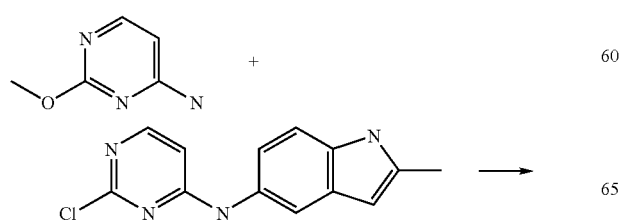

Example 300

Synthesis of N-(2-(4-fluorophenoxy)pyrimidin-4-yl)-2-methyl-1H-indol-5-amine (Compound 300)

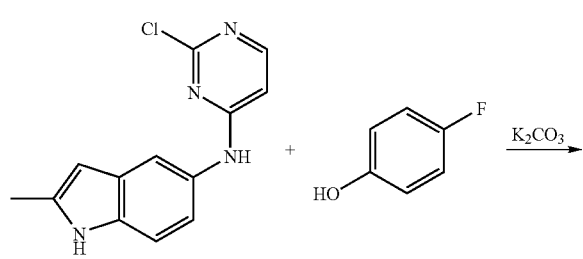

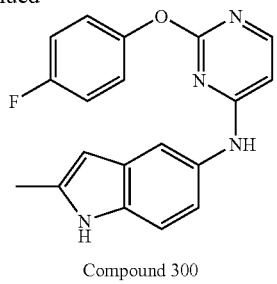

Compound 300

N-(2-chloropyrimidin-4-yl)-2-methyl-1H-indol-5-amine (0.1 mmol) and p-fluorophenol (0.1 mmol) were dissolved in 0.5 ml DMF. To this was added $K_2CO_3$ (0.2 mmol). After stirred at 60° C. for 5 h, the reaction mixture was diluted with water and extracted with ethyl acetate. The organic layer was washed with water and brine sequentially, dried by anhydrous $Na_2SO_4$, and concentrated. The resulting oil residue was purified by column chromatography to provide compound 300 in a yield of 76%.

$^1$H NMR (DMSO-d6, 400 MHz): δ 10.802 (s, 1H), 9.491 (s, 1H), 7.990 (d, J=5.4 Hz 1H), 7.495 (s, 1H), 7.295 (m, J=8.4-3.6 Hz, 4H), 7.236 (d, J=5.4 Hz 1H), 7.133 (d, J=5.6 Hz, 1H), 6.486 (d, J=5.6 Hz, 1H), 5.902 (s, 1H), 2.402 (s, 3H); MS (m/e): 335.1 (M+1).

Example 301-303

Syntheses of Compounds 301-303

Compounds 301-303 were prepared in a similar manner to that described in Example 300.

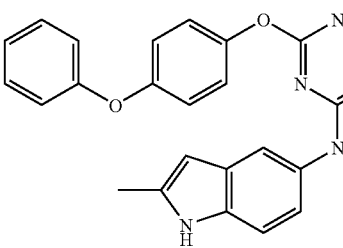

| Compound | Name | $^1$H NMR (CD$_3$OD, 400 MHz)/MS |
|---|---|---|
| 301 | 2-methyl-N-(2-(4-phenoxyphenoxy)pyrimidin-4-yl)-1H-indol-5-amine | 11.190 (s, 1H), 9.046 (s, 1H), 7.959 (s, 1H), 7.931 (d, J = 6.0 Hz, 1H), 7.681 (d, J = 7.2 Hz, 2H), 7.361 (t, J = 8.0-7.6 Hz, 2H), 7.114 (m, J = 8.4-7.2 Hz, 3H), 6.903 (d, J = 8.0 Hz, 2H), 6.755 (d, J = 7.2 Hz, 2H), 6.179 (s, 1H), 6.024 (s, 1H), 2.338 (s, 3H); MS (m/e): 409.2 (M + 1) |
| 302 | N2-cyclopropyl-N4-(2-methyl-1H-indol-5-yl)pyrimidine-2,4-diamine | 7.739 (d, J = 6.4 Hz, 1H), 7.593 (s, 1H), 7.252 (d, J = 7.6 Hz, 1H), 7.119 (d, J = 8.0 Hz, 1H), 6.009 (s, 1H), 6.016 (d, J = 6.0 Hz, 1H), 2.425 (s, 3H), 0.784 (m, J = 5.2-2.4, 2H), 0.626 (m, J = 2.0-0.8 Hz, 3H), 0.547 (m, J = 2.0-1.2 Hz, 3H). MS (m/e): 280.2 (M + 1) |
| 303 | N2-cyclohexyl-N4-(2-methyl-1H-indol-5-yl)pyrimidine-2,4-diamine | MS (m/e): 322.3 (M + 1) |

| Compound Name | $^1$H NMR (CD$_3$OD, 400 MHz)/MS |
|---|---|
| 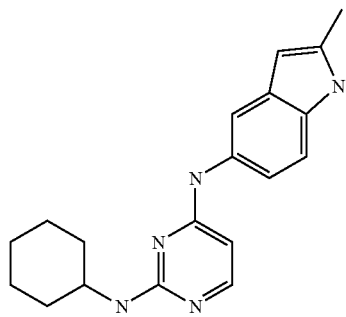 [SMILES: Cc1cc2cc(Nc3ccnc(NC4CCCCC4)n3)ccc2[nH]1] | |

Example 304

Synthesis of 5-(2-(3-methoxyphenoxy)pyrimidin-4-yloxy)-2-methyl-1H-indole (Compound 304)

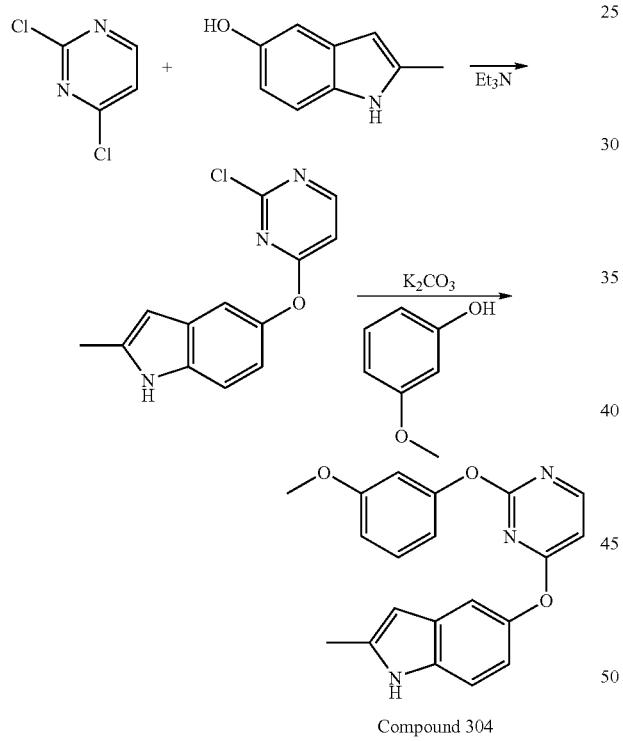

Compound 304

To a solution of 2,4-dichloropyrimidine (1 mmol) and 5-hydroxy-2-methylindole (1 mmol) in 5 ml EtOH was added Et$_3$N (1 mmol). The reaction mixture was refluxed for 5 h. After removal of the solvent in vacuo and addition of H$_2$O, the mixture was extracted with EtOAc. The organic layers were combined, washed with a saturated NaCl aqueous solution, dried over anhydrous Na$_2$SO$_4$, and concentrated in vacuo. The resulting oil residue was purified by column chromatography to give 5-(2-chloropyrimidin-4-yloxy)-2-methyl-1H-indole in a yield of 75%.

5-(2-Chloropyrimidin-4-yloxy)-2-methyl-1H-indole (0.1 mmol) and m-methoxyphenol (0.1 mmol) were dissolved in 0.5 ml DMF. K$_2$CO$_3$ (0.2 mmol) was then added. After the reaction mixture was stirred at 60° C. for 5 h, it was diluted with water and extracted with ethyl acetate. The organic layer was washed with water and brine sequentially, dried over anhydrous Na$_2$SO$_4$, and concentrated. The crude product was purified by column chromatography to provide compound 304 in a yield of 76%.

$^1$H NMR (CD$_3$OD, 400 MHz): δ 8.303 (d, J=5.6 Hz, 1H), 8.084 (s, 1H), 7.305-7.262 (m, 3H), 6.908 (dd, J=8.8 Hz, J=2.4 Hz, 1H), 6.816-6.764 (m, 3H), 6.463 (d, J=5.6 Hz, 1H), 6.226 (s, 1H), 3.780 (s, 3H), 2.465 (s, 3H); MS (m/e): 346.5 (M−1).

Example 305

Synthesis of 3-(4-(2-methyl-1H-indol-5-ylamino)pyrimidin-2-ylamino)benzonitrile (Compound 305)

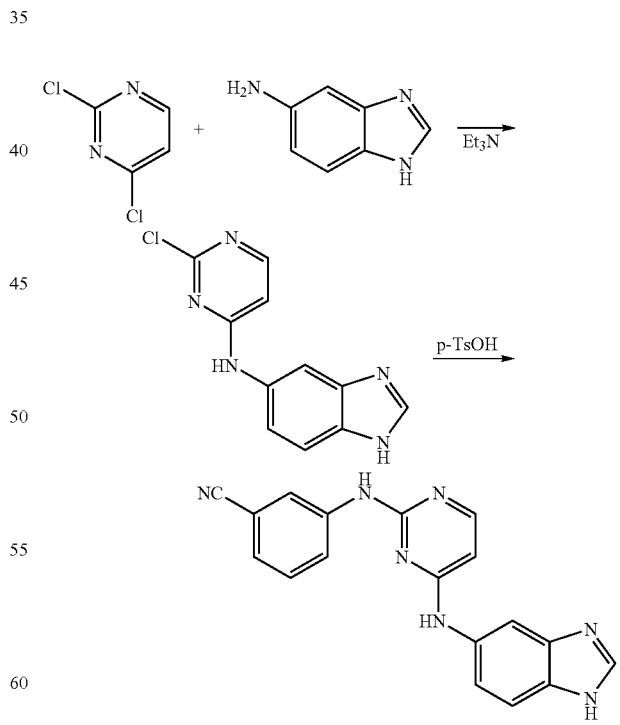

Compound 305

To a solution of 2,4-dichloropyrimidine (1 mmol) and 5-Aminobenzimidazole (1 mmol) in 5 ml EtOH, was added Et$_3$N (1 mmol). The reaction mixture was refluxed for 5 hours. After removal of the solvent in vacuo and addition of H₂O, the mixture was extracted with EtOAc. The organic layers were combined, washed with a saturated NaCl aqueous solution, dried over anhydrous Na₂SO₄, and concentrated in vacuo. The residue was purified by column chromatography to give N-(2-chloropyrimidin-4-yl)-1H-benzo[d]imidazol-5-amine in a yield of 80%.

N-(2-chloropyrimidin-4-yl)-1H-benzo[d]imidazol-5-amine (0.1 mmol), 3-aminobenzonitrile (0.1 mmol), and p-TsOH monohydrate (0.2 mmol) were dissolved in 0.5 ml DMF. After the reaction mixture was stirred at 60° C. for 5 h, it was diluted with water and extracted with ethyl acetate. The organic layer was washed with water and brine sequentially, dried over anhydrous Na₂SO₄, and concentrated. The resulted oil was purified by column chromatography to provide compound 305 in a yield of 76%.

¹H NMR (CD₃OD, 400 MHz): δ 8.178 (s, 1H), 7.942 (d, J=6.4 Hz, 2H), 7.825 (br, 1H), 7.633-7.603 (m, 2H), 7.469 (dd, J=8.8 Hz, 5 Hz, 1H), 7.212 (t, J=8.4 Hz, 1H), 7.075 (d, J=8.0 Hz, 1H), 6.254 (d, J=6.0 Hz, 1H), 3.345 (s, 1H); MS: 327.2 (M+1).

Example 306

Synthesis of N2-(3-methoxyphenyl)-N4-(2-methyl-benzo[d]oxazol-6-yl)pyrimidine-2,4-diamine (Compound 306)

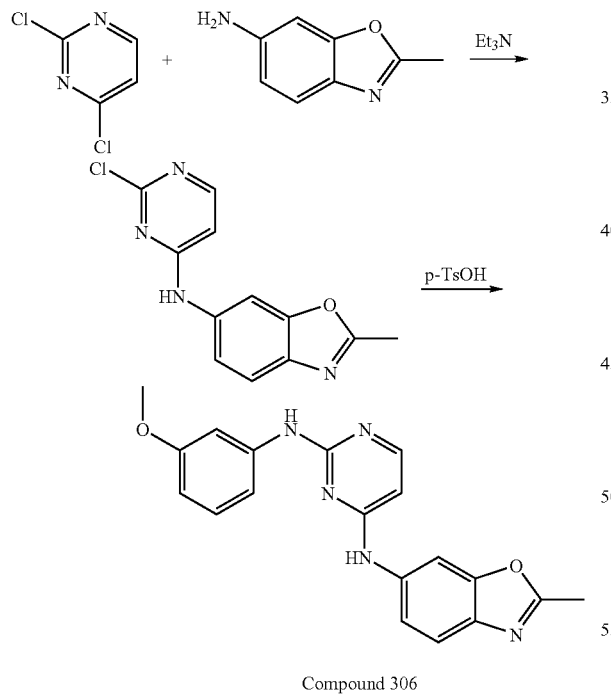

Compound 306

To a solution of 2,4-dichloropyrimidine (1 mmol) and 2-methyl-1,3-benzoxazol-5-amine (1 mmol) in 5 ml EtOH was added Et₃N (1 mmol). The reaction mixture was refluxed for 5 h. After removal of the solvent in vacuo and addition of H₂O, the mixture was extracted with EtOAc. The organic layers were combined, washed with a saturated NaCl aqueous solution, dried over anhydrous Na₂SO₄, and concentrated in vacuo. The residue was purified by column chromatography to give N-(2-chloro pyrimidin-4-yl)-2-methylbenzo[d]oxazol-6-amine in a yield of 73%.

N-(2-chloropyrimidin-4-yl)-2-methylbenzo[d]oxazol-6-amine (0.1 mmol), 3-methoxyaniline (0.1 mmol), and p-TsOH monohydrate (0.2 mmol) were dissolved in 0.5 ml DMF. After the reaction mixture was stirred at 60° C. for 5 h, it was diluted with water and extracted with ethyl acetate. The organic layer was washed with water and brine sequentially, dried over anhydrous Na₂SO₄, and concentrated. The resulting oil residue was purified by column chromatography to provide compound 306 in a yield of 82%.

¹H NMR (DMSO-d6, 400 MHz): δ 9.431 (s, 1H), 9.158 (s, 1H), 8.136 (s, 1H), 8.022 (d, J=5.6 Hz, 1H), 7.566 (d, J=8.8 Hz, 1H), 7.517 (d, J=8.8 Hz, 1H), 7.418 (s, 1H), 7.367 (d, J=8.0 Hz 1H), 7.126 (t, J=8.4 Hz, 1H), 6.490 (m, 1H), 6.224 (d, J=5.2 Hz, 1H), 3.674 (s, 3H), 2.609 (s, 3H); MS (m/e): 348.3 (M+1).

Example 307

Synthesis of N2-(3-ethynylphenyl)-N4-(2-methyl-benzo[d]oxazol-6-yl)pyrimidine-2,4-diamine (Compound 307)

Compound 307 was synthesized in a similar manner to that described in Example 306.

¹H NMR (DMSO-d6, 400 MHz): δ 9.566 (d, J=5.2 Hz, 1H), 9.309 (s, 1H), 8.099 (s, 1H), 8.038 (d, J=6.0 Hz, 1H), 7.917 (s, 1H), 7.805 (d, J=8.4 Hz, 1H), 7.574 (m, 2H), 7.231 (m, 1H), 6.996 (d, J=7.6 Hz, 1H), 7.278 (d, J=5.6 Hz, 1H), 4.059 (s, 1H), 2.608 (s, 3H); MS (m/e): 342.2 (M+1).

Example 308

Synthesis of N2-(3-ethynylphenyl)-N4-(1H-indazol-6-yl)pyrimidine-2,4-diamine (Compound 308)

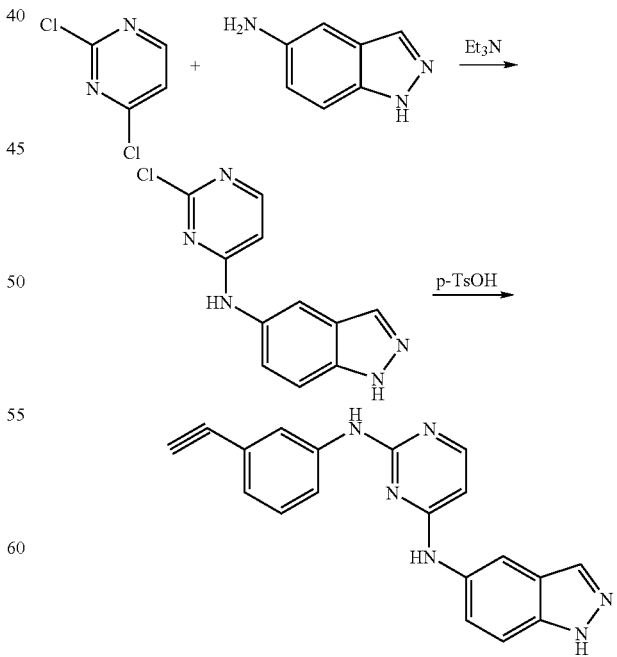

Compound 308

To a solution of 2,4-dichloropyrimidine (1 mmol) and 5-aminoindazole (1 mmol) dissolved in 5 ml EtOH was added Et₃N (1 mmol). The reaction mixture was refluxed for 5 h. After removal of the solvent in vacuo and addition of H₂O, the mixture was extracted with EtOAc. The organic layers were combined, washed with a saturated NaCl aqueous solution, dried over anhydrous Na₂SO₄, and concentrated in vacuo. The resulted oil was purified by column chromatography to give N-(2-chloropyrimidin-4-yl)-1H-indazol-5-amine in a yield of 80%.

N-(2-chloropyrimidin-4-yl)-1H-indazol-5-amine (0.1 mmol), 3-ethynylaniline (0.1 mmol), and p-TsOH (0.2 mmol, monohydrate) were dissolved in 0.5 ml DMF. After the reaction mixture was stirred at 60° C. for 5 h, it was diluted with water and extracted with ethyl acetate. The organic layer was washed with water and brine sequentially, dried over anhydrous Na₂SO₄, and concentrated. The residue was purified by column chromatography to provide compound 308 in a yield of 74%.

¹H NMR (DMSO-d₆, 400 MHz): δ 12.966 (brs, 1H), 9.344 (brs, 1H), 9.234 (brs, 1H), 8.145 (s, 1H), 8.005 (m, 2H), 7.893 (s, 1H), 7.795 (d, 1H), 7.527 (d, J=8.8 Hz, 1H), 7.471 (d, J=8.8 Hz, 1H), 7.212 (t, 1H), 7.021 (d, 1H), 6.626 (d, 1H), 4.037 (s, 1H); MS (m/e): 327.2 (M+1).

Example 309

Synthesis of N2-(3-methoxylphenyl)-N4-(2-methyl-1H-indol-5-yl)pyrimidine-2,4-diamine (Compound 309)

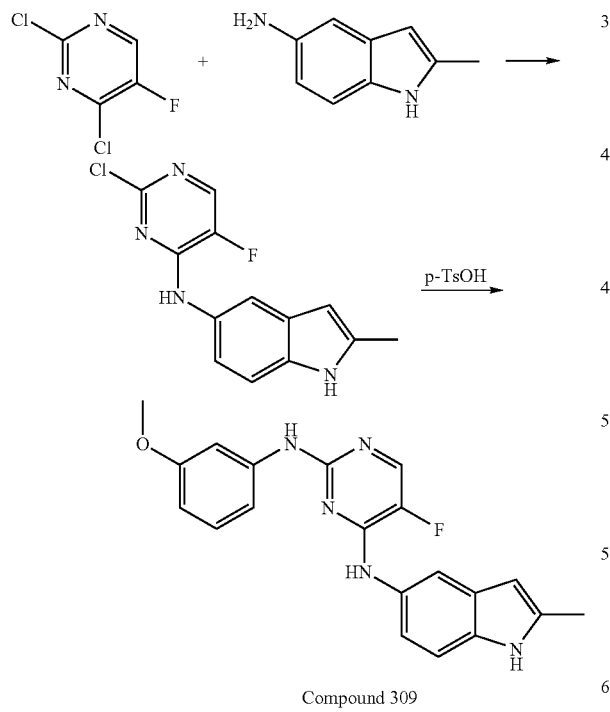

Compound 309

2,4-Dichloro-5-fluoropyrimidine (1 mmol) and 5-amino-2-methylindole (1.5 mmol) were dissolved in 3 ml CH₃OH and 9 ml H₂O. After the reaction mixture was stirred at room temperature for 1 h, it was diluted with H₂O, acidified with 2N HCl, and sonicated. The reaction mixture was then filtered, washed with H₂O and dried to give N-(2-chloro-5-fluoropyrimidin-4-yl)-2-methyl-1H-indol-5-amine in a yield of 78%.

N-(2-chloro-5-fluoropyrimidin-4-yl)-2-methyl-1H-indol-5-amine (0.1 mmol), m-methoxyaniline (0.1 mmol), p-TsOH monohydrate (0.2 mmol) were dissolved in 0.5 ml DMF. After the reaction mixture was stirred at 60° C. for 5 h, it was diluted with water and extracted with ethyl acetate. The organic layer was washed with water and brine sequentially, dried over anhydrous Na₂SO₄, and concentrated. The residue was purified by column chromatography to provide compound 309 in a yield of 60%.

¹H NMR (CD₃OD, 400 MHz, δ ppm): 7.854 (d, J=4.0 Hz, 1H), 7.703 (d, J=1.6, 1H), 7.248 (s, 2H), 7.177 (br, 2H), 7.054 (t, J=4.2 Hz, 2H), 6.942 (s, 2H), 3.506 (s, 3H), 2.235 (s, 3H); MS (m/e): 364.2 (M+1).

Example 310

Synthesis of 2-(3-methoxyphenylamino)-4-(2-methyl-1H-indol-5-ylamino)pyrimidine-5-carbonitrile (Compound 310)

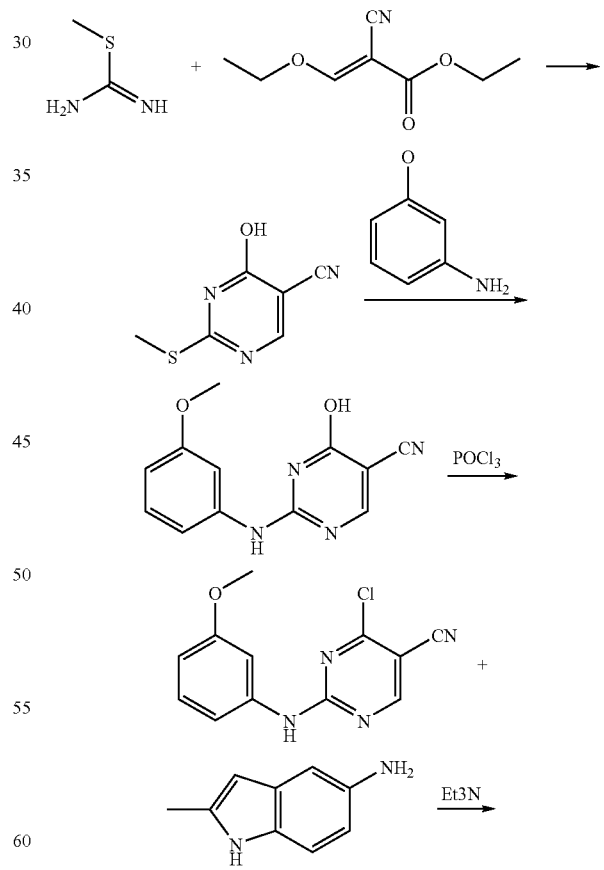

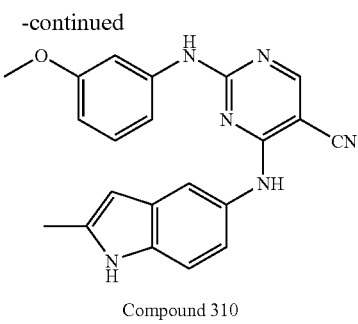

Compound 310

2-Methyl-2-thiopseudourea (5 mmol) and ethyl ethoxymethylenecyanoacetate (5 mmol) were dissolved in 20 ml EtOH. To this was added $K_2CO_3$ (10 mmol). After the mixture was refluxed for 48 h, it was cooled to room temperature and filtered. The solvent was concentrated in vacuo and purified by column chromatography to give 4-hydroxy-2-(methylthio) pyrimidine-5-carbonitrile in a yield of 65%.

4-Hydroxy-2-(methylthio) pyrimidine-5-carbonitrile (3 mmol) and m-anisidine (3 mmol) in pentan-1-ol was refluxed for 40 h under nitrogen. The reaction mixture was concentrated in vacuo. The residue was washed with water and dried to afford 4-hydroxy-2-(3-methoxyphenylamino)pyrimidine-5-carbonitrile.

To a solution of 4-hydroxy-2-(3-methoxyphenylamino)pyrimidine-5-carbonitrile in $POCl_3$ was added DMF 0.5 ml. The solution was refluxed for 3 h. The reaction mixture was cooled to room temperature and poured into ice-water. The solution was adjusted to pH=8-9 by aqueous sodium carbonate solution and extracted with dichloromethane. The combined organic layers were washed with brine, dried over anhydrous $Na_2SO_4$, concentrated in vacuo to afford 4-chloro-2-(3-methoxyphenylamino)pyrimidine-5-carbonitrile.

4-Chloro-2-(3-methoxyphenylamino)pyrimidine-5-carbonitrile was converted to compound 310 in a similar manner to that described in Example 1.

$^1$H NMR (DMSO-d6, 400 MHz): δ 10.925 (s, 1H), 9.710 (d, J=11.2 Hz, 1H), 0.349 (d, J=10.4 Hz, 1H), 8.441 (s, 1H), 7.474 (s, 1H), 7.252 (s, 1H), 7.223 (d, J=6.8 Hz, 1H), 7.187 (s, 1H), 7.062 (m, J=1H), 6.923 (d, J=2.0 Hz, 1H), 6.485 (t, 1H); 6.098 (s, 1H), 3.453 (s, 3H), 2.387 (s, 3H); MS (m/e): 371.2 (M+1).

Example 311-317

Syntheses of Compounds 311-317

Compounds 311-317 were prepared in a similar manner to that described in Example 310.

| compound | Name/Structure | $^1$H NMR(DMSO-$d_6$,400 Hz)/MS |
|---|---|---|
| 311 | 4-(2-methyl-1H-indol-5-ylamino)-2-(3-(3-morpholinopropoxy)phenylamino)pyrimidine-5-carbonitrile | 11.184 (s, 1H), 10.745 (s, 1H), 9.492 (s, 1H), 8.396 (s, 1H), 7.322 (s, 1H), 7.292 (d, J = 7.2, 1H), 7.147 (m, 1H), 6.919 (m, 1H), 6.815 (d, J = 8.8, 1H), 6.416 (d, J = 7.2, 1H), 6.261 (t, J = 4.8, 1H), 6.129 (s, 1H), 3.447 (m, 2H), 3.547 (m, 4H), 2.398 (s, 3H), 2.337 (m, 6H), 1.747 (m, 2H). MS (m/e): 484.2 (M + 1) |
| 312 | 4-(2-methyl-1H-indol-5-yloxy)-2-(3-(3-morpholinopropoxy)phenylamino)pyrimidine-5-carbonitrile | MS (m/e): 485.3 (M + 1) |
| 313 | 4-(2-methyl-1H-indol-5-ylamino)-2-(3-(2-morpholinoethoxy)phenylamino)pyrimidine-5-carbonitrile | MS (m/e): 470.5 (M + 1) |

| compound | Name/Structure | $^1$H NMR(DMSO-$d_6$,400 Hz)/MS |
|---|---|---|
| 314 | 4-(4-fluoro-2-methyl-1H-indol-5-ylamino)-2-(3-(trifluoromethyl)phenylamino)-pyrimidine-5-carbonitrile | MS (m/e): 427.2 (M + 1) |
| 315 | 2-(3,4-dimethoxyphenylamino)-4-(2-methyl-1H-indol-5-ylamino)pyrimidines carbonitrile | MS (m/e): 401.4 (M + 1) |
| 316 | 4-(4-fluoro-2-methyl-1H-indol-s-ylamino)-2-(3-(2-morpholinoethoxy)phenylamino)pyrimidine-5-carbonitrile | MS (m/e): 488.5 (M + 1) |
| 317 | 2-(5-cyano-2-(3,4-dimethoxyphenylamino) pyrimidin-4-ylamino)benzamide | MS (m/e): 391.1 (M + 1) |

Example 318

KDR, Kinase Activity Assay Using Z'-Lyte Kinase Assay Kit

Inhibition of kinase activity of a recombinant KDR catalytic domain (Invitrogen, Carlsbad, Calif., U.S.A., Cat. PV3660) was determined using Z'-LYTE™ Tyr1 Peptide assay kit (Invitrogen, Cat. PV3190) in a black 384-well plate (Thermo labsystems, Cambridge, U.K., Cat. 7805). The assay was performed according to the procedures recommended by the manufacturer.

Briefly, a test compound (10 mM stock in DMSO) was diluted to 1:4 with distilled water containing 8% DMSO. The solution was placed in a test well and three control wells (C1, C2, and C3) at 2.5 μl/well. Coumarin-fluorescein double-labeled peptide substrate was mixed with the KDR catalytic domain ("kinase"). 5 μl of the kinase/peptide mixture was added to each of the test, C1, and C2 wells, but not C3 (Final concentration: 0.3 μg/ml of Kinase, 2 μM of peptide). 5 μl of Phosphor-Tyr1 peptide was added to the C3 well. 2.5 μl of 40 μM ATP was added to the test well and C2 well and 2.5 μl of 1.33× kinase buffer (1× buffer: 50 mM HEPES, pH7.5, 0.01% Brij-35, 5 mM MgCl$_2$, 5 mM MnCl$_2$, and 1 mM EGTA) was added to the C1 and C3 wells. The plate was briefly spun at 1000 rpm to settle all solution down to the bottom of the wells and then sealed and shaken at 250 rpm and 25° C. for 1 hour.

A development reagent was diluted to 1:128 according to the recommendation of the manufacturer. 5 μl of the diluted development reagent was added to each well. The plate was spun at 1000 rpm to settle all solution down to the wells, and then sealed and shaken at 250 rpm and 25° C. for 1 hour.

5 μl of a stop reagent was added to each well. The plate was spun at 1000 rpm to settle all solution down to the wells, and then sealed at 250 rpm and 25° C. for 2 minutes. Emission of the solution at each well was measured by a Victor™3 microplate reader at Excitation 400 nm/Emission 445 nm and 520 nm. The emission ratio and phosphorylation ("Phos.") percentage were calculated by the following equations:

$$\text{Emission Ratio} = \frac{\text{Coumarin Emission (445 nm)}}{\text{Fluorescein Emission (520 nm)}}$$

% Phosphorylation=

$$1 - \frac{(\text{Emission Ratio} \times F_{100\%}) - C_{100\%}}{(C_{0\%} - C_{100\%}) + [\text{Emission Ratio} \times (F100\% - F0\%)]}$$

where:

$C_{100\%}$=Average Coumarin emission signal of the 100% Phos. Control $C_{0\%}$=Average Coumarin emission signal of the 0% Phos. Control
$F_{100\%}$=Average Fluorescein emission signal of the 100% Phos. Control
$F_{0\%}$=Average Fluorescein emission signal of the 0% Phos. Control The inhibition ratio was calculated as follows:

Inhibition %=(Phos. in C2 well−Phos. in test well)/(Phos. in C2 well)×100%

The result showed that all of the tested compounds inhibited the activity of KDR. The $IC_{50}$ values ranged from 0.001 to 10 μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention can be made and used to practice this invention. Thus, other embodiments are also within the claims.

What is claimed is:
1. A compound of the following formula:

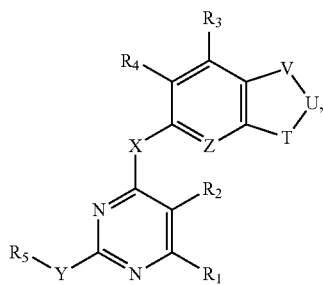

and/or a pharmaceutically acceptable salt thereof, in which
each of X and Y, independently, is O, S, or NR, wherein R is H, alkyl, alkenyl, alkynyl, aryl, cycloalkyl, heterocycloalkyl, heteroaryl, alkylcarbonyl, alkoxycarbonyl, aminocarbonyl, or aminosulfonyl;
Z is CR', wherein R' is H, halo, nitro, cyano, hydroxyl, alkoxy, aryloxy, alkyl, alkenyl, alkynyl, aryl, cycloalkyl, or heterocycloalkyl;
V, U, and T together represent

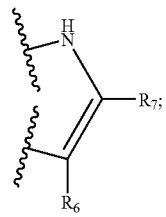

each of $R_1$, $R_2$, $R_3$, $R_4$, and $R_6$, independently, is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl;
$R_5$ is alkyl, cycloalkyl, heterocycloalkyl, aryl or heteroaryl; and
$R_7$ is alkyl.

2. The compound of claim 1, and/or pharmaceutically acceptable salt thereof, wherein X is O.
3. The compound of claim 2, and/or pharmaceutically acceptable salt thereof, wherein Y is NH.
4. The compound of claim 3, and/or pharmaceutically acceptable salt thereof, wherein R' is H, halo, or alkyl.
5. The compound of claim 4, and/or pharmaceutically acceptable salt thereof, wherein $R_6$ is H and $R_7$ is methyl.
6. The compound of claim 5, and/or pharmaceutically acceptable salt thereof, wherein $R_5$ is aryl or heteroaryl, optionally substituted with halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, sulfonyl, carbonylamino, sulfonylamino, aminocarbonyl, or aminosulfonyl.
7. The compound of claim 1, and/or pharmaceutically acceptable salt thereof, wherein R' is H, halo, or alkyl.
8. The compound of claim 7, and/or pharmaceutically acceptable salt thereof, wherein $R_6$ is H and $R_7$ is methyl.
9. The compound of claim 1, and/or pharmaceutically acceptable salt thereof, wherein $R_5$ is aryl or heteroaryl, optionally substituted with halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, sulfonyl, carbonylamino, sulfonylamino, aminocarbonyl, or aminosulfonyl.
10. The compound of claim 1, and/or pharmaceutically acceptable salt thereof, wherein Y is NH.
11. The compound of claim 1, and/or pharmaceutically acceptable salt thereof, wherein the compound is selected from

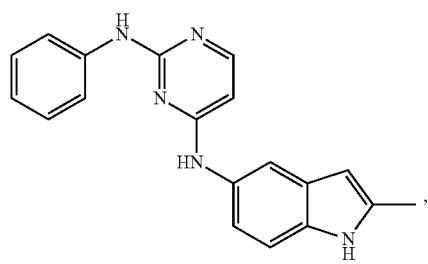

Compound 1

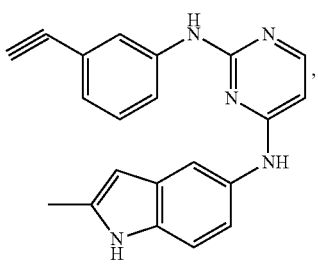

Compound 2

-continued
Compound 3
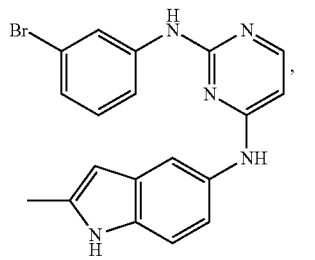
Compound 4
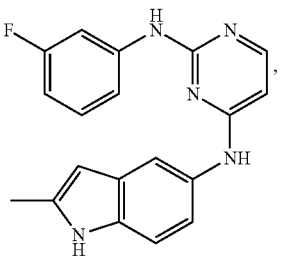
Compound 5
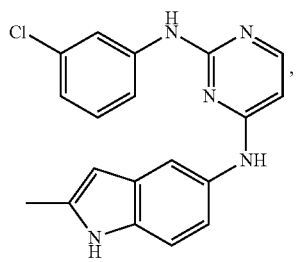
Compound 6
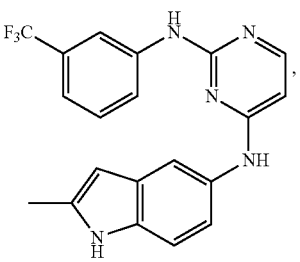
Compound 7
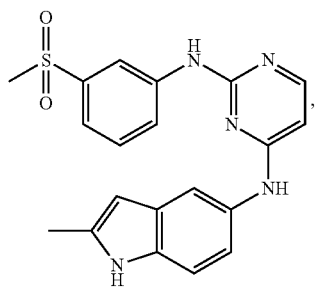
Compound 8
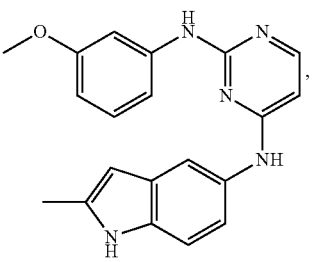
Compound 9
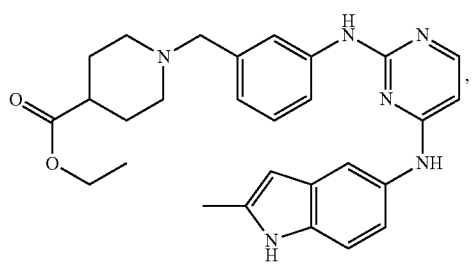
Compound 10
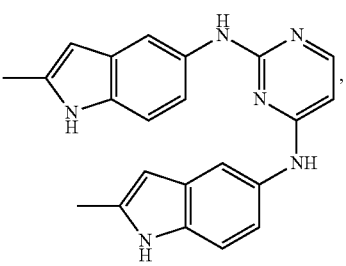
Compound 11
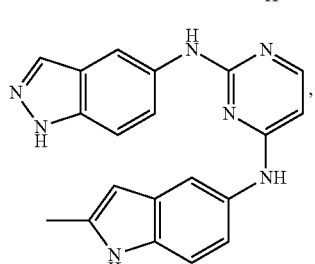
Compound 12
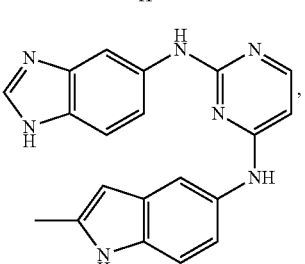
Compound 13
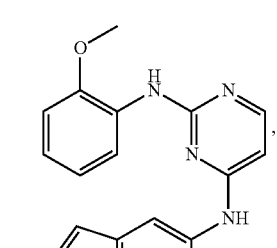
Compound 14
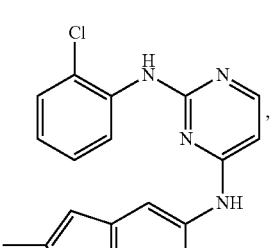

12. A pharmaceutical composition, comprising a compound of claim 1, and/or a pharmaceutically acceptable salt thereof, and a pharmaceutically acceptable carrier thereof.

* * * * *